United States Patent
Johansen et al.

(10) Patent No.: US 6,593,133 B1
(45) Date of Patent: Jul. 15, 2003

(54) NEUROTROPHIC FACTORS

(75) Inventors: Teit E. Johansen, Horsholm (DK); Nikolaj Blom, Copenhagen (DK); Claus Hansen, Holbaek (DK)

(73) Assignee: NsGENE A/S, Ballerup (DK)

(*) Notice: Subject to any disclaimer, the term of this patent is extended or adjusted under 35 U.S.C. 154(b) by 0 days.

(21) Appl. No.: 09/347,613

(22) Filed: Jul. 2, 1999

Related U.S. Application Data

(60) Provisional application No. 60/092,229, filed on Jul. 9, 1998, provisional application No. 60/097,774, filed on Aug. 25, 1998, and provisional application No. 60/103,908, filed on Oct. 3, 1998.

(30) Foreign Application Priority Data

| Jul. 19, 1998 | (DK) | 1998 00904 |
| Aug. 19, 1998 | (DK) | 1998 01048 |
| Oct. 6, 1998 | (DK) | 1998 01265 |

(51) Int. Cl.$^7$ .......... C12P 21/06; C12N 15/00; C12N 5/00; C12N 15/63; C12N 1/12; C12N 15/74; C07H 21/02; C07H 21/04; C07K 1/00

(52) U.S. Cl. ............ 435/325; 435/69.1; 435/320.1; 435/252.1; 435/252.3; 435/471; 435/455; 435/91.1; 435/91.3; 536/23.1; 536/23.5; 530/350; 530/351

(58) Field of Search .................. 536/23.1, 23.5; 435/91.1, 91.3, 69.1, 320.1, 325, 455, 252.1, 471, 252.3; 514/44; 424/93.2; 530/350, 351

(56) References Cited

U.S. PATENT DOCUMENTS

| 4,883,666 A | 11/1989 | Sabel et al. .................. 424/422 |
| 5,084,350 A | 1/1992 | Chang et al. ............. 428/402.2 |
| 5,284,761 A | 2/1994 | Aebischer et al. .......... 435/182 |
| 5,496,804 A | 3/1996 | Reed et al. .................... 514/12 |
| 5,618,531 A | 4/1997 | Cherksey .................... 424/93.7 |
| 5,733,729 A | 3/1998 | Lipshutz et al. ............... 435/6 |
| 5,754,524 A | 5/1998 | Wark .......................... 364/497 |
| 5,795,716 A | 8/1998 | Chee et al. ..................... 435/6 |
| 5,800,992 A | 9/1998 | Fodor et al. .................... 435/6 |
| 5,834,029 A | 11/1998 | Bellamkonda et al. ...... 424/570 |
| 5,916,555 A | 6/1999 | Lee et al. .................. 424/93.5 |

FOREIGN PATENT DOCUMENTS

| WO | WO 93/06116 | 4/1993 |
| WO | WO 97/08196 | 3/1997 |
| WO | WO 98/32869 | 7/1998 |
| WO | WO 00/04050 | 1/2000 |

OTHER PUBLICATIONS

Masure et al., *Enovin, a member of the glial cell–line–derived neurotrophic factor (GDNF) family with growth promoting activity on neuronal cells.* Eur. J. Biochem. 266: 892–902 (1999).

Sauer and Oertel, 1994. Progressive degeneration of nigrostriatal dopamine neurons following intrstriatal terminal lesions with 6–hydroxydopamine: a combined retrograde tracing and immunocytochemical study in the rat. *Neuroscience* 59: 401–415.

Baloh, et al., 1998. Artemin, a novel member of the GDNF ligand family, suports peripheral and central neurons and signals through the GRFα3–RET receptor complex. *Neuron* 21: 1291–1302.

Milbrandt, et al., 1998. Persephin, a novel neurotrophic factor related to GDNF and neurturin. . *Neuron* 20: 245–253.

Airaksinen, et al., 1999. GDNF family neurotrophic factor signaling: Four masters, one servant?.*Mol. Cell. Neurosci.* 13: 313–325.

Atschul, et al., 1997. Gapped BLAST and PSI–BLAST: a new generation of protein database search programs. *Nucl. Acids Res.* 25: 3389–3402.

Thompson, et al., 1997. The ClustalX windows interface: flexible strategies for multiple sequence alignment aided by quality analysis tools. *Nuc. Acids Res.* 25 : 4876–4882.

Eigenbrot and Gerber, 1997. X–ray strucutre of glial cell–derived neurotrophic factor at 1.9 A resolution and implications for receptor binding. *Nat. Struct. Biol.* 4: 435–438.

Lorenz, et al., 1996. Heteromultimeric CLC chloride channels with novel properties. *Proc. Natl. Acad. Sci. USA* 93: 13362–13366.

Borodovsky, et al., 1995. Detection of new genes in a bacterial genome using Markov models for three gene classes. *Nucl. Acids Res.* 23: 3554–3562.

Finsen, et al., 1992. Somatostatin and neuropeptide Y in organotypic slice cultures of the rat hippocampus: an immunocytochemical and in situ hybridization study. *Neurosci.* 47:105–113.

Slooth and Gramsbergen, 1995. Detection of salicylate and its hydroxylated adducts 2,3– and 2,5–dihydroxybenzoic acids as possible indices for in vivo hydroxyl radical formation in combination with catechol– and indoleamines and their metabolites in cerebrospinal fluid and brain tissue. *J. Neurosci. Meth.* 60: 141–149.

Daopin, et al., 1993. Crystal structure of TGF–β2 refined at 1.8 A resolution. *Proteins* 17: 176–192.

Sanicola, et al., 1997. Glial cell line–derived neurotrophic factor–dependent RET activation can be mediated by two different cell–surface accesory proteins. *Proc. Natl. Acad Sci USA* 94: 6238–6243.

Stoppini, et al., 1991. A simple method for organotypic cultures of nervous tissue. *J. Neurosci. Methods* 37: 173–182.

(List continued on next page.)

Primary Examiner—Jeffrey Fredman
Assistant Examiner—Sumesh Kaushal
(74) *Attorney, Agent, or Firm*—Mintz, Levin, Cohn, Ferris, Glovsky and Popeo, P.C.; Ivor R. Elrifi; Scott D. Miller

(57) ABSTRACT

The invention relates to neublastin neurotrophic factor polypeptides, nucleic acids encoding neublastin polypeptides, and antibodies that bind specifically to neublastin polypeptides, as well as methods of making and methods of using the same.

22 Claims, 16 Drawing Sheets

OTHER PUBLICATIONS

Zufferey, et al., 1997. Multiply attenuated lentiviral vector achieves efficient gene delivery in vivo. *Nat. Biotechnol.* 1997 15: 871–875.

von Schwedler, et al., 1993. Vif is crucial for human immunodeficiency virus type 1 proviral DNA synthesis in infected cells. *J. Virol.* 67: 4945–4955.

Robertson and Manson, *The GDNF–RET signalling in partnership*, Trends Genet. 13: 1–3 (1997).

Lapchak, *Therapeutic potentials for glial cell line–derived neurotrophic factor (GDNF) based upon pharmacological activities in the CNS*, Rev. Neurosci. 7: 165–176 (1997).

Unsicker, *GDNF: a cytokine at the interface of TGF–betas and neurotrophins*, Cell Tissue Res. 286: 175–178 (1996).

Lapchak, et al., *Pharmacological characterization of glial cell line–derived neurotrophic factor (GDNF): implications for GDNF as a therapeutic molecule for treating neurodegenerative diseases*, Cell Tissue Res. 286: 179–189 (1996).

Nucleotide Sequence Database EMBL Entry AA844072, Accession No. AA844072.

Massagué, et al., 1994. The TGF–β family and its composite receptor, *Trends Cell Biol.* 4: 172–178.

McDonald & Hendrickson, 1993. A structural superfamily of growth factors containing a cystine knot motif, *Cell* 73: 421–424.

Lin, et al., 1993. GDNF: A glial cell line–derived neurotrophic factor for midbrain dopaminergic neurons, *Science* 260: 1130–1132.

Verma et al., Gene therapy–promises, problems and prospects, 1997, Nature, pp. 239–242.*

Varmus, Gene therapy: Not ready for prime time, 1996, Nature Medicine, vol. 2, pp. 7–8.*

Rosenblad et al., In vivo protection of nigral dopamine neurons by lentiviral gene transfer of the novel GDNF–family member neublastin/artemin, 2000, Molecular and Cellular Neuroscience, vol. 15, pp. 199–214.*

Rosenberg et al., Gene therapist, heal thyself, 2000, Science, vol. 287, p. 1751.*

Verma, Gene therapy: Beyond 2000,2000, Molecular Therapy, vol. 6, pp. 493.*

Friedmann, Principles for human gene therapy studies, 2000, Science, vol. 287, pp.2163–2164.*

Anderson, Human gene therapy, 1998, Nature, vol. 392, pp. 25–30.*

During et al., Towards gene therapy for the cetral nervous system, 1998, Molecular Medicine, vol. 11, pp. 485–493.*

AC005051, Waterston, 1998.*

AF0G7197, Li, 1998.*

AAN40033, Gray et al., 1992.*

* cited by examiner

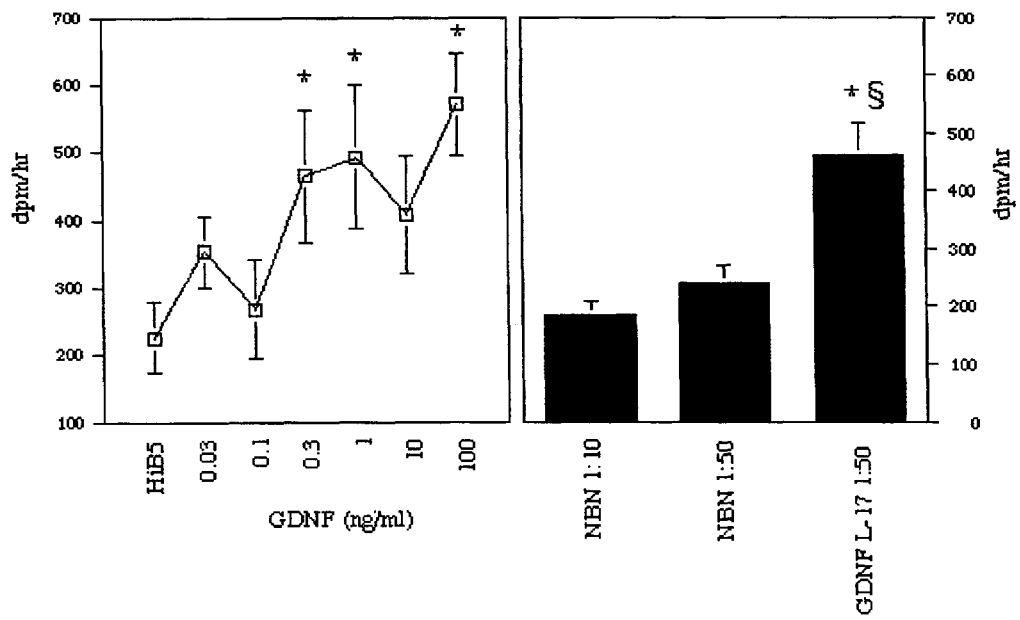
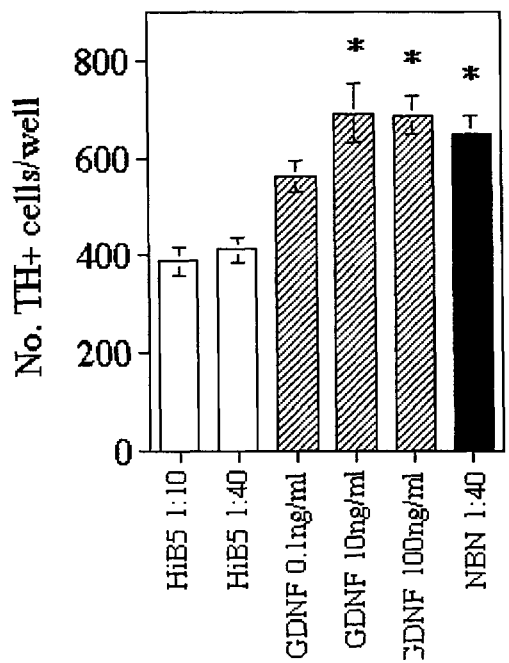
Figs. 4A, 4B and 4C

Alignment of Neublastin primers used in Rapid-Screen with homologous regions in other GDNF ligands

```
5'-C CTG GCC AGC CTA CTG GG-3'        SEQ ID No 17
   G CTG GCC CGG CTG CAG GG           persephin
   G CTG CGA CGA CTG CGC CA           neurturin
   A TTG AAA AAC TTA TCC AG           GDNF 5'-AA GGA GAC CGC     TTC GTA GCG-3'  SEQ ID No 18
   TA GGC CAC GTC     GGT GTA GCG     persephin
   AA GGA CAC CTC GTC CTC GTA GGC     neurturin
   AA CGA CAG GTC ATC ATC AAA GGC     GDNF
``` conserved nucleotides shown in bold

Fig. 8

1. Control medium stained with R30 anti-peptide antibody
2. Neublastin containing conditioned medium stained with R30 anti-peptide antibody
3. Control medium stained with R31 anti-peptide antibody
4. Neublastin containing conditioned medium stained with R31 anti-peptide antibody Extraction of neublastin by affinity-binding on RETL3-Ig
Lane 1: bound from CHO control conditioned media
Lane 2: bound from neublastin overexpressing CHO conditioned media

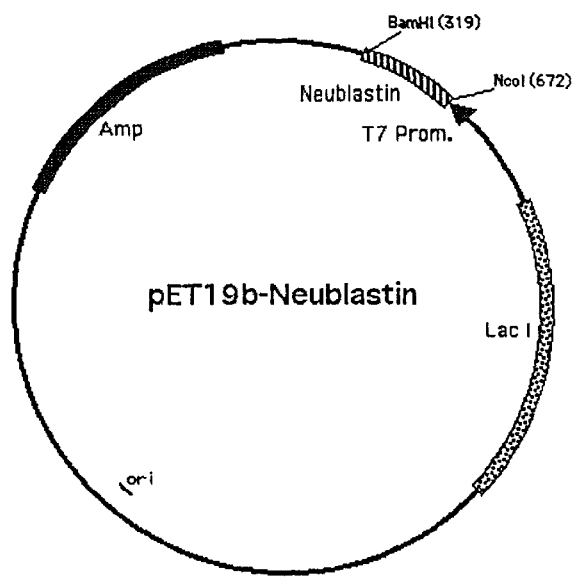

Neublastin Syngene

```
         NcoI (318)
316  TACCATGGCT GGAGGACCGG GATCTCGTGC TCGTGCAGCA GGAGCACGTG GCTGTCGTCT
     ATGGTACCGA CCTCCTGGCC CTAGAGCACG AGCACGTCGT CCTCGTGCAC CGACAGCAGA
     1▶ M  A   G  G  P    G  S  R  A  R  A  A   G  A  R    G  C  R  L

376  GCGTTCTCAA CTAGTGCCGG TGCGTGCACT CGGACTGGGA CACCGTTCCG ACGAACTAGT
     CGCAAGAGTT GATCACGGCC ACGCACGTGA GCCTGACCCT GTGGCAAGGC TGCTTGATCA
     19▶ R  S  Q   L  V  P   V  R  A  L   G  L  G   H  R  S   D  E  L  V

436  ACGTTTTCGT TTTTGTTCAG GATCTTGTCG TCGTGCACGT TCTCCGCATG ATCTATCTCT
     TGCAAAAGCA AAAACAAGTC CTAGAACAGC AGCACGTGCA AGAGGCGTAC TAGATAGAGA
     39▶ R  F  R   F  C  S   G  S  C  R   R  A  R   S  P  H   D  L  S  L

496  AGCATCTCTA CTAGGAGCCG GAGCACTAAG ACCGCCGCCG GGATCTAGAC CTGTATCTCA
     TCGTAGAGAT GATCCTCGGC CTCGTGATTC TGGCGGCGGC CCTAGATCTG GACATAGAGT
     59▶ A  S  L   L  G  A   G  A  L  R   P  P  P   G  S  R   P  V  S  Q

556  ACCTTGTTGT AGACCTACTA GATACGAAGC AGTATCTTTC ATGGACGTAA ACTCTACATG
     TGGAACAACA TCTGGATGAT CTATGCTTCG TCATAGAAAG TACCTGCATT TGAGATGTAC
     79▶ P  C  C   R  P  T   R  Y  E  A   V  S  F   M  D  V   N  S  T  W

BamHI (671)
616  GAGAACCGTA GATAGACTAT CTGCAACCGC ATGTGGCTGT CTAGGATGAT AAATAGGGATC
     CTCTTGGCAT CTATCTGATA GACGTTGGCG TACACCGACA GATCCTACTA TTTATCCCTAG
     99▶ R  T  V   D  R  L   S  A  T  A   C  G  C    L  G  •  •  •

676  CGGCT
     GCCGA
```

Fig. 14

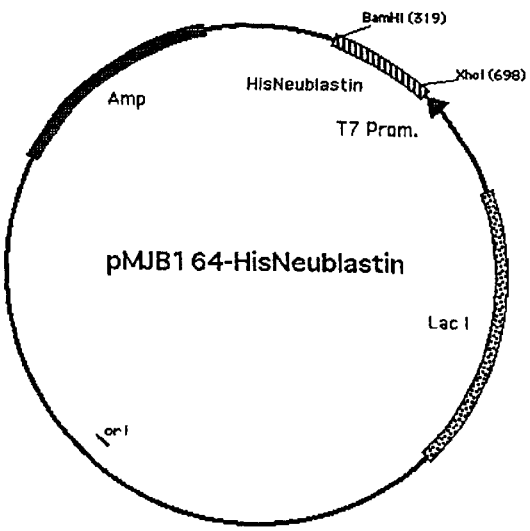

HisNeublastin

```
                                                              XhoI (340)
301  TACCATGGGC CATCATCATC ATCATCATCA TCATCATCAC TCGAGCGGCC ATATCGACGA
     ATGGTACCCG GTAGTAGTAG TAGTAGTAGT AGTAGTAGTG AGCTCGCCGG TATAGCTGCT
  1▶  M  G  H  H  H  H  H  H  H  H  H  S  S  G  H  I  D  D

361  CGACGACAAG GCTGGAGGAC CGGGATCTCG TGCTCGTGCA GCAGGAGCAC GTGGCTGTCG
     GCTGCTGTTC CGACCTCCTG GCCCTAGAGC ACGAGCACGT CGTCCTCGTG CACCGACAGC
 19▶  D  D  K  A  G  G  P  G  S  R  A  R  A  A  G  A  R  G  C  R

421  TCTGCGTTCT CAACTAGTGC CGGTGCGTGC ACTCGGACTG GGACACCGTT CCGACGAACT
     AGACGCAAGA GTTGATCACG GCCACGCACG TGAGCCTGAC CCTGTGGCAA GGCTGCTTGA
 39▶  L  R  S  Q  L  V  P  V  R  A  L  G  L  G  H  R  S  D  E  L

481  AGTACGTTTT CGTTTTTGTT CAGGATCTTG TCGTCGTGCA CGTTCTCCGC ATGATCTATC
     TCATGCAAAA GCAAAAACAA GTCCTAGAAC AGCAGCACGT GCAAGAGGCG TACTAGATAG
 59▶  V  R  F  R  F  C  S  G  S  C  R  R  A  R  S  P  H  D  L  S

541  TCTAGCATCT CTACTAGGAG CCGGAGCACT AAGACCGCCG CCGGGATCTA GACCTGTATC
     AGATCGTAGA GATGATCCTC GGCCTCGTGA TTCTGGCGGC GGCCCTAGAT CTGGACATAG
 79▶  L  A  S  L  L  G  A  G  A  L  R  P  P  P  G  S  R  P  V  S

601  TCAACCTTGT TGTAGACCTA CTAGATACGA AGCAGTATCT TTCATGGACG TAAACTCTAC
     AGTTGGAACA ACATCTGGAT GATCTATGCT TCGTCATAGA AAGTACCTGC ATTTGAGATG
 99▶  Q  P  C  R  P  T  R  Y  E  A  V  S  F  M  D  V  N  S  T

BamHI (719)
661  ATGGAGAACC GTAGATAGAC TATCTGCAAC CGCATGTGGC TGTCTAGGAT GATAATAGGG
     TACCTCTTGG CATCTATCTG ATAGACGTTG GCGTACACCG ACAGATCCTA CTATTATCCC
119▶  W  R  T  V  D  R  L  S  A  T  A  C  G  C  L  G  •  •

721  ATCCGGCTGC TAACAAAGCC CG
     TAGGCCGACG ATTGTTTCGG GC
```

Fig. 15

NEUROTROPHIC FACTORS

This application claims benefit of U.S. Serial No. 60/092,229, filed Jul. 9, 1998; U.S. Serial No. 60/097,774, filed Aug. 25, 1998, and U.S. Serial No. 60/103,908, filed Oct. 3, 1998. It also claim benefit of Danish patent application 1998 00904, filed Jul. 6, 1998; Danish patent application 1998 01048, filed Aug. 19, 1998 and Danish patent application 1998 01265, filed Oct. 6, 1998.

FIELD OF THE INVENTION

The invention relates to neurotrophic factor polypeptides, nucleic acids encoding neurotrophic factor polypeptides, and antibodies that bind specifically to neurotrophic factors.

BACKGROUND

Neurotrophic factors are naturally-occurring proteins which promote survival, maintain phenotypic differentiation, prevent degeneration, and enhance the activity of neuronal cells and tissues. Neurotrophic factors are isolated from neural tissue and from non-neural tissue that is innervated by the nervous system, and have been classified into functionally and structurally related groups, also referred to as families, superfamilies,or subfamilies. Among the neurotrophic factor superfamilies are the fibroblast growth factor, neurotrophin, and transforming growth factor- β (TGF-β) superfamilies. Individual species of neurotrophic factors are distinguished by their physical structure, their interaction with their composite receptors, and their affects on various types of nerve cells. Classified within the TGF-β superfamily (Massague, et al,. 1994, *Trends in Cell Biology*, 4:172–178) are the glial cell line-derived neurotrophic factor ligands ("GDNF"; WO 93/06116, incorporated herein by reference), which include GDNF, persephin ("PSP"; Milbrandt et al., 1998, *Neuron* 20:245–253, incorporated herein by reference) and neurturin ("NTN"; WO 97/08196, incorporated herein by reference). The ligands of the GDNF subfamily have in common their ability to induce signalling through the RET receptor tyrosine kinase. These three ligands of the GDNF subfamily differ in their relative affinities for a family of neurotrophic receptors, the GFRα receptors.

Due to the affects of neurotrophic factors on neuronal tissue, there remains a need to identify and characterise additional neurotrophic factors for diagnosing and treating disorders of the nervous system.

SUMMARY OF THE INVENTION

This invention relates to a novel neurotrophic factor herein called "neublastin," or "NBN." Neublastin is classified within the GDNF subfamily because it shares regions of homology with other GDNF ligands (see Tables 3 and 4, infra) and because of its ability to interact with RET (see, e.g., Airaksinen et al., Mol. Cell. Neuroscience, 13, pp. 313–325 (1999)), neublastin is a novel and unique neurotrophic factor. Unlike other GDNF ligands, neublastin exhibits high affinity for the GFRα3-RET receptor complex and unique subregions in its amino acid sequence.

A "neublastin polypeptide," as used herein, is a polypeptide which possesses neurotrophic activity (e.g., as described in Examples 6, 7, 8, and 9) and includes those polypeptides which have an amino acid sequence that has at least 70% homology to the human "neublastin" polypeptides set forth in $AA_{-95}$–$AA_{105}$ of SEQ. ID. NO. 2, $AA_1$–$AA_{105}$ of SEQ. ID. NO. 2, $AA_{-97}$–$AA_{140}$ of SEQ. ID. NO. 4, $AA_{-41}$–$AA_{140}$ of SEQ. ID. NO. 4 ("pro"), $AA_1$–$AA_{140}$ of SEQ. ID. NO. 4, $AA_{-80}$–$AA_{140}$ of SEQ. ID. NO. 9 ("wild type" prepro), $AA_{-41}$–$AA_{140}$ of SEQ. ID. NO. 9 (pro), $AA_1$–$AA_{140}$ of SEQ. ID. NO. 5 (mature 140AA), $AA_1$–$AA_{116}$ of SEQ. ID. NO. 6 (mature 116AA), $AA_1$–$AA_{113}$ of SEQ. ID. NO. 7 (mature 113AA), $AA_1$–$AA_{140}$ of SEQ. ID. NO. 10 (mature 140AA), $AA_1$–$AA_{116}$ of SEQ. ID. NO. 11 (mature 116AA), $AA_1$–$AA_{113}$ of SEQ. ID. NO. 12 (mature 113AA), and variants and derivatives thereof. In addition, this invention contemplates those polypeptides which have an amino acid sequence that has at least 70% homology to the murine "neublastin" polypeptides set forth in $AA_1$–$AA_{224}$ of SEQ. ID. NO. 16.

Preferably, the C-terminal sequence of the above identified neublastin polypeptides has an amino acid sequence as set forth in $AA_{72}$–$AA_{105}$ of SEQ. ID. NO. 2 (i.e., $AA_{107}$–$AA_{140}$ of SEQ. ID. NO. 9), more preferably $AA_{41}$–$AA_{105}$ of SEQ. ID. NO. 2 (i.e., $AA_{76}$–$AA_{140}$ of SEQ. ID. NO. 9), or the amino acid sequence set forth in $AA_{191}$–$AA_{224}$ of SEQ. ID. NO. 16.

Also, it is preferable that the neublastin polypeptide retain the 7 conserved Cys residues that are characteristic of the GDNF family and of the TGF-beta super family.

Preferably, the neublastin polypeptide has an amino acid sequence greater than 85% homology, most preferably greater than 95% homology, to the foregoing sequences (i.e., $AA_{-95}$–$AA_{105}$ of SEQ. ID. NO. 2, $AA_1$–$AA_{105}$ of SEQ. ID. NO. 2, $AA_{-97}$–$AA_{140}$ of SEQ. ID. NO. 4, $AA_1$–$AA_{140}$ of SEQ. ID. NO. 4, $AA_{-41}$–$AA_{140}$ of SEQ. ID. NO. 4, $AA_{80}$–$AA_{140}$ of SEQ. ID. NO. 9 ("wild type" prepro), $AA_{-41}$–$AA_{140}$ of SEQ. ID. NO. 9 (pro), $AA_1$–$AA_{140}$ of SEQ. ID. NO. 5 (mature 140AA), $AA_1$–$AA_{116}$ of SEQ. ID. NO. 6 (mature 116AA), $AA_1$–$AA_{113}$ of SEQ. ID. NO. 7 (mature 113AA), $AA_1$–$AA_{140}$ of SEQ. ID. NO. 10 (mature 140AA), $AA_1$–$AA_{116}$ of SEQ. ID. NO. 11 (mature 116AA), $AA_1$–$AA_{113}$ of SEQ. ID. NO. 12 (mature 113AA)), and $AA_1$–$AA_{224}$ of SEQ. ID. NO. 16.

A "neublastin nucleic acid," as used herein, is a polynucleotide which codes for a neublastin polypeptide. Accordingly, an isolated neublastin nucleic acid is a polynucleotide molecule having an open reading frame of nucleotide codons that, were it to be exposed to the appropriate components required for translation, would encode, or code for, a neublastin polypeptide. Neublastin nucleic acids of the invention may be RNA or DNA, e.g., genomic DNA, or DNA which is complementary to and/or transcribed from, a neublastin mRNA ("cDNA"). Thus, a neublastin nucleic acid of the invention further includes polynucleotide molecules which hybridize with specificity, under high stringency hybridization conditions, to a polynucleotide that codes for a neublastin polypeptide. This invention also relates to nucleic acid primers that are useful in identifying, isolating and amplifying polynucleotides that encode neublastin polypeptides, or fragments thereof. In certain embodiments of the invention, certain of these primers are neublastin-specific probes useful for hybridization to a neublastin nucleic acid, but not to nucleic acids coding for the other members of the GDNF family. By "specific", "specificity", or "specifically", is meant an ability to hybridize with neublastin nucleic acid and inability to hybridize with non-neublastin nucleic acids, including an inability to hybridize to nucleic acids that code uniquely for the GDNF ligands (e.g., GDNF, persephin, and neurturin).

In another embodiment, a neublastin nucleic acid of the invention is one that is identified as being complementary to a polynucleotide that codes for a neublastin polypeptide, either by having a complementary nucleic acid sequence or demonstrating that it hybridizes with specificity at high stringency hybridization conditions to a polynucleotide that codes for neublastin. Particular neublastin nucleic acids include, without limitation, the nucleic acid sequences shown herein and designated SEQ ID NO: 1, SEQ ID NO: 3, SEQ ID NO: 8, SEQ ID NO: 13, SEQ ID NO: 14, SEQ ID NO: 15, SEQ ID NO: 29 and SEQ ID NO: 30 as well as primers SEQ ID NOS: 17–28, 31 and 32. A neublastin nucleic acid of the invention further includes a unique subregion, or fragment, of a neublastin nucleic acid, including without limitation the nucleic acid fragments shown in FIG. 8.

The neublastin nucleic acids of the invention may be used to express a neublastin polypeptide, e.g., by expressing a neublastin polypeptide in vitro, or by administering a neublastin nucleic acid to an animal for in vivo expression. Neublastin nucleic acids may be included within a nucleic acid vector, e.g., an expression vector or a cloning vector. A neublastin nucleic acid may, but need not of necessity, be maintained, reproduced, transferred, or expressed as part of a nucleic acid vector. A recombinant expression vector containing a neublastin polynucleotide sequence can be introduced into and/or maintained within a cell. Cells hosting a neublastin vector may be prokaryotic. Alternatively, a neublastin nucleic acid can be introduced into a eukaryotic cell, e.g., a eukaryotic cell that contains the appropriate apparati for posttranslational processing of a polypeptide into a mature protein, and/or the appropriate apparati for secreting a polypeptide into the extracellular environment of the cell.

The invention further features a neublastin neurotrophic factor, "neublastin." Neublastin may be in the form of a polypeptide, or may be a multimer of two or more neublastin polypeptides, e.g., a neublastin dimer. Neublastin polypeptides are associated as multimers by intermolecular structural associations known to those skilled in the art, including without limitation cysteine-cysteine interaction, sulfhydryl bonds, and noncovalent interactions. Particular neublastin polypeptides include, without limitation, an amino acid sequence disclosed herein and designated SEQ ID NO: 2; SEQ ID NO: 4; SEQ ID NO: 5; SEQ ID NO: 6; SEQ ID NO: 7; SEQ ID NO: 9; SEQ ID NO: 10; SEQ ID NO: 11, SEQ ID NO: 12 and SEQ ID NO: 16.

A neublastin polypeptide of the invention is useful for treating a defect in a neuron, including without limitation lesioned neurons and traumatized neurons. Peripheral nerves that experience trauma include, but are not limited to, nerves of the medulla or of the spinal cord. Neublastin polypeptides are useful in the treatment of neurodegenerative disease, e.g., cerebral ischemic neuronal damage; neuropathy, e.g., peripheral neuropathy, Alzheimer's disease, Huntington's disease, Parkinson's disease, amyotrophic lateral sclerosis (ALS). Neublastin polypeptides are further contemplated for use in the treatment of impaired memory, e.g., memory impairment associated with dementia.

BRIEF DESCRIPTION OF THE DRAWINGS

FIG. 4 is a graphical illustration of the effect of neublastin on the survival of cultured rat embryonic, dopaminergic, ventral mesencephalic neurons and ChAT activity in cholinergic cranial nerve motor neurons in serum-free medium. In particular, FIG. 4A is an illustration of the dose-response curve for recombinant GDNF on ChAT activity (dpm/hour). FIG. 4B is an illustration of ChAT activity (dpm/hour) using diluted conditioned medium from either neublastin producing or GDNF-producing cells. FIG. 4C is an illustration of the number of tyrosine hydroxylase immunoreactive cells per well.

FIG. 5 is an illustration of the effect of neublastin secreted from HiB5pUbi1zNBN22 cells on the function and survival of slice cultures of pig embryonic dopaminergic ventral mesencephalic neurons co-cultured with either HiB5pUbi1zNBN22 cells (neublastin) or HiB5 cells (control).

FIG. 8 is an illustration of neublastin specific primers used to identify the cDNA clone encoding the human neublastin polypeptide that hybridize to nucleic acids that encode neublastin polypeptides, but do not hybridize to nucleic acids encoding the other known GDNF family members (i.e., GDNF (SEQ ID NOS: 40 and 43), Persephin (SEQ ID NOS: 38 and 41)and neurturin(SEQ ID NOS: 39 and 42.

FIG. 14 is a plasmid map of pET19b-Neublastin, along with the sequence of the synthetic gene for Neublastin SEQ ID NO: 29.

FIG. 15 is a plasmid map of pMJB 164-HisNeublastin, along with the sequence of the synthetic gene for HisNeublastin SEQ ID NO: 30.

DETAILED DISCLOSURE OF THE INVENTION

Figure 1:
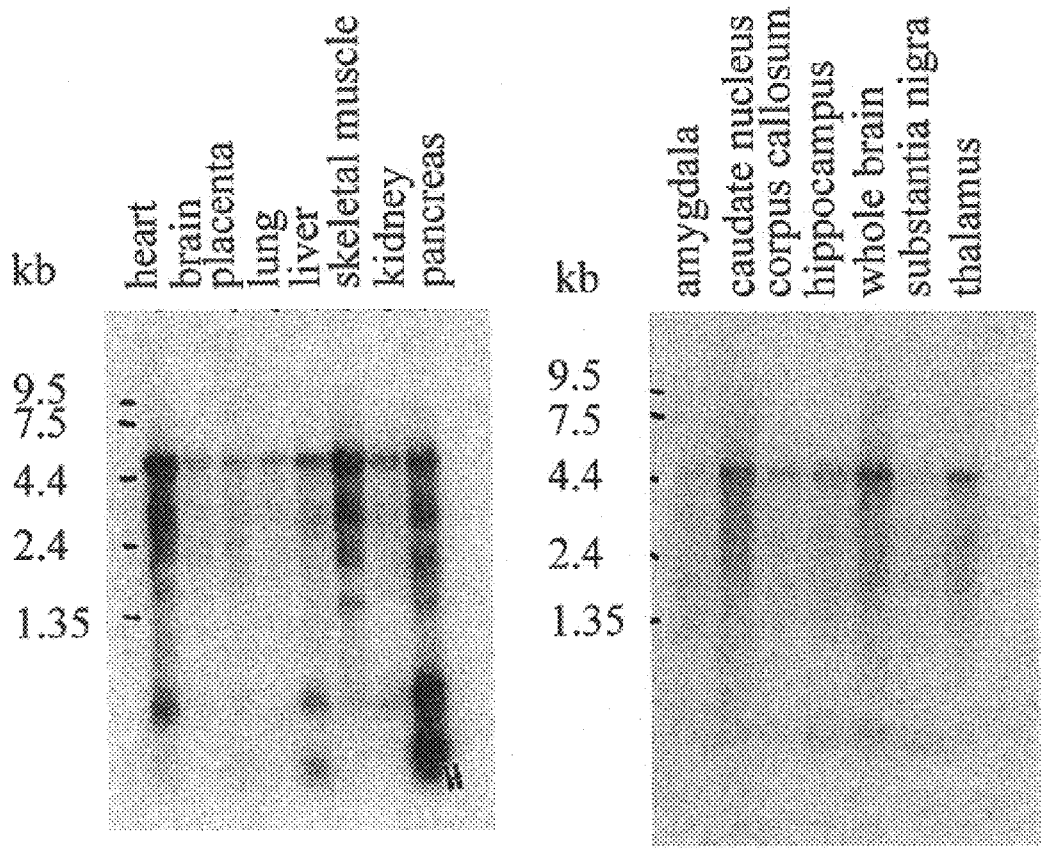
FIG. 1 is a photographic image of two northern blots probed with $^{32}$P-labelled neublastin cDNA, comparing relative levels of expression of the neublastin gene in various human adult tissue types (left blot) and in various regions of the adult human brain (right blot).

Applicant have identified a nucleic acid that encodes a novel neurotrophic factor which is referred to herein as "neublastin," or "NBN." Neublastin is a member of the glial cell line-derived neurotrophic factor (GDNF) sub-class of the transforming growth factor-β (TGF-β) super-family of neurotrophic factors.

The cDNA encoding neublastin was originally identified as follows. Using the TBLASTN 1.4.11 algorithm (Atschul et al., *Nucl. Acids Res.*, 25, pp. 3389–3402 (1997)) and human persephin as query (GenBank Acc. No. AF040962), a 290 bp fragment was initially identified in High-Throughput Genomic Sequence (HGTS) of two human bacterial artificial chromosomes (BAC) with GenBank entries AC005038 and AC005051. AC005038 consists of approximately 190,000 bp of 5 contigs of unordered sequences and AC005051 consists of approximately 132,000 bp of 12 contigs of unordered sequences. The 290 bp fragment identified in the two BAC clones proved to have regions that were homologous, but not identical, to a coding region of the cDNA of the neurotrophic factor, human persephin.

From this 290 bp sequence two Neublastin-specific PCR primers were synthesised (Top Stand Primer [SEQ ID NO. 17] and Bottom Strand Primer [SEQ ID NO. 18]). Screening of human fetal brain cDNA library was performed. The initial screening comprised 96-well PCR-based screening with the two PCR primers [SEQ ID NOS. 17 and 18] of a cDNA library "Master Plate" from 500,000 cDNA clones containing approximately 5,000 clones/well. A second PCR-based screen was performed on a human fetal brain cDNA library "Sub-Plate" containing *E. coli* glycerol stock with approximately 5,000 clones/well.

A 102 bp fragment [SEQ ID NO. 13] was identified in the PCR-based screenings of both the Master Plate and Sub Plate. A positive cDNA clone (possessing the 102 bp fragment) was selected, plated on two LB/antibiotic-containing plates, and grown overnight. From these plates, a total of 96 bacterial colonies were selected and individually placed in the wells of a new, 96-well PCR plate containing both PCR primers [SEQ ID NOS. 17 and 18] and the requisite PCR amplification reagents. PCR amplification was then performed and the 96 individual PCR reactions were analyzed by 2% agarose gel electrophoresis. The positive colony with the clone containing the 102 bp fragment was then identified. Plasmid DNA was obtained from the positive colony containing the 102 bp fragment and sequenced. Subsequent sequencing analysis revealed the presence of a full-length cDNA of 861 bp [SEQ ID NO. 8]. The Open Reading Frame (ORF) of 663 bp, or coding region (CDS), identified in SEQ ID NO. 8, encodes the pre-pro-polypeptide (designated "pre-pro-Neublastin") and is shown in SEQ ID NO: 9. Based on SEQ ID NO: 9, three variants of Neublastin polypeptides were identified. These variants include:

(i) the 140 AA polypeptide designated herein as NBN140, which possesses the amino acid sequence designated as SEQ ID NO: 10;

(ii) the 116 AA polypeptide designated herein as NBN116, which possesses the amino acid sequence designated as SEQ ID NO: 11; and (iii) the 113 AA polypeptide designated herein as NBN113, which possesses the amino acid sequence designated as SEQ ID NO: 12.

The entire cDNA sequence containing 782 bp 5' untranslated DNA, 663 bp encoding DNA, and 447 3' untranslated (totalling 1992 bp) has been submitted to GenBank under the Accession Number AF 120274.

The genomic Neublastin-encoding sequence was identified as follows:

With the goal of cloning the genomic neublastin-encoding sequence, an additional set of primers were prepared. In particular, Primer Pair No. 1 comprised [sense=SEQ ID NO:23 and antisense SEQ ID NO:24] and Primer Pair No. 2 comprised [sense=SEQ ID NO:25 and antisense SEQ ID NO:26].

Using Primer Pair No. 2, a 887 bp DNA fragment was amplified by PCR from a preparation of human genomic DNA, and cloned into the pCRII vector (Invitrogen) and transformed into *E. coli*. The resulting plasmid was sequenced and a 861 bp putative cDNA sequence (encoding a protein named neublastin herein) was predicted (as set forth in SEQ.ID.NO.3). Similarly, using Primer Pair No. 1, an 870 bp DNA fragment was obtained by PCR of human genomic DNA. An additional 42 bp region at the 3'-terminus of the Open Reading Frame (ORF) was found in this fragment, in comparison to the 887 bp sequence. The genomic structure of the neublastin gene was predicted by comparing it to the sequences of nucleic acids of other neurotrophic factors, by mapping exon-intron boundaries. This analysis demonstrated that the neublastin gene has at least two exons separated by a 70 bp intron.

This sequence was also used to screen GenBank for neublastin EST sequences. Three were identified with GenBank entries AA844072, AA931637 and AA533512, indicating that neublastin nucleic acids are transcribed into mRNA.

Comparison of the entire cDNA sequence obtained (AF 120274) and the genomic sequence present in GenBank entries AC005038 and AC005051 revealed that the neublastin gene consists of at least five exons (including three coding) separated by four introns (see, e.g., FIG. 8). Together, the exons have a predicted amino acid sequence of a full-length Neublastin polypeptide. It should also be noted that the 887 bp fragment was found to contain the complete coding region of pro-neublastin. The predicted cDNA [SEQ ID NO: 3] contains an Open Reading Frame (ORF) encoding pro-neublastin (181 amino acid residues) which showed homology to the three known human proteins—Persephin, Neurturin, and GDNF.

Neublastin Nucleic Acids of the Invention

In another aspect the invention provides polynucleotides capable of expressing the polypeptides of the invention. The polynucleotides of the invention include DNA, cDNA and RNA sequences, as well as anti-sense sequences, and include naturally occurring, synthetic, and intentionally manipulatedpolynucleotides. The polynucleotides of the invention also include sequences that are degenerate as a result of the genetic code, but which code on expression for a neublastin polypeptide.

As defined herein, the term "polynucleotide" refers to a polymeric form of nucleotides of at least 10 bases in length, preferably at least 15 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes recombinant DNA which is incorporated into an expression vector, into an autonomously replicating plasmid or virus, or into the genomic DNA of a prokaryote or eukaryote, or which exists as a separate molecule, e.g. a cDNA, independent from other sequences.

The polynucleotides of the invention also include allelic variants and "mutated polynucleotides" having a nucleotide sequence that differs from the nucleotide sequences presented herein at one or more nucleotide positions.

In a preferred embodiment, the polynucleotide of the invention has a nucleic acid (DNA) sequence capable of hybridizing with the polynucleotide sequence presented as SEQ ID NO: 1, the polynucleotide sequence presented as SEQ ID NO: 3, the polynucleotide sequence presented as SEQ ID NO: 8, or the polynucleotide sequence presented as SEQ ID NO: 15, its complementary strand, or a sub-sequence hereof under at least medium, medium/high, or high stringency conditions, as described in more detail below.

In another preferred embodiment, the isolated polynucleotide of the invention has a nucleic acid (DNA) sequence that is at least 70%, preferably at least 80%, more preferred at least 90%, most preferred at least 95% homologous to the polynucleotide sequence presented as SEQ ID NO: 1, the polynucleotide sequence presented as SEQ ID NO: 3, the polynucleotide sequence presented as SEQ ID NO: 8, or the polynucleotide sequence presented as SEQ ID NO: 15.

In its most preferred embodiment, the polynucleotide has the DNA sequence presented as SEQ ID NO: 1, the DNA sequence presented as SEQ ID NO: 3, the DNA sequence presented as SEQ ID NO: 8, or the polynucleotide sequence presented as SEQ ID NO: 15.

This invention also provides novel primers and DNA sequences for identifying, isolating and amplifying neublastin polynucleotides which code on expression for neublastin polypeptides or fragments thereof. Such primers include the polynucleotides set forth in SEQ.ID.NOS. 17–28, and 31–32. In addition, this invention provides neublastin DNA sequences generated from those primers, including those set forth in SEQ.ID.NOS. 13 and 14. Further, this invention provides DNA sequences from 3' or 5' untranslated regions ("UTR") in genomic DNA that flank neublastin exons; such sequences are useful in identifying, isolating and amplifying neublastin polynucleotides which code on expression for neublastin polypeptides or fragments thereof.

3' UTR sequences of this invention include the sequences set forth in:

nucleotides 721–865 of SEQ.ID.NO. 1,
nucleotides 718–861 of SEQ.ID.NO. 3,
nucleotides 718–861 of SEQ.ID.NO. 8,
nucleotides 1647–2136 of SEQ.ID.NO. 15, and
contiguous sequences of between 10–25 nucleotides derived from (i.e., falling within) the foregoing sequences (which are useful, e.g., as primers).

5' UTR sequences of this invention include the sequences set forth in:

nucleotides 1–10 of SEQ.ID.NO. 1,
nucleotides 1–57 of SEQ.ID.NO. 8,
nucleotides 1–974 of SEQ.ID.NO. 15, and contiguous sequences of between 10–25 nucleotides derived from (i.e., falling within) the foregoing sequences (which are useful, e.g., as primers).

The polynucleotides of the invention may preferably be obtained by cloning procedures, e.g. as described in "Current Protocols in Molecular Biology" [John Wiley & Sons, Inc.]. In a preferred embodiment, the polynucleotide is cloned from, or produced on the basis of human genomic DNA or a cDNA library of the human brain.

Homology of DNA sequences

The DNA sequence homology referred to above may be determined as the degree of identity between two sequences indicating a derivation of the first sequence from the second. The homology may suitably be determined by means of computer programs known in the art, such as GAP provided in the GCG program package [Needleman, S. B. and Wunsch C. D., *Journal of Molecular Biology* 1970 48 443–453]. Using GAP with the following settings for DNA sequence comparison: GAP creation penalty of 5.0 and GAP extension penalty of 0.3, the coding region of the analogous DNA sequences referred to above exhibits a degree of identity preferably of at least 70%, more preferably at least 80%, more preferably at least 90%, more preferably at least 95%, with the CDS (encoding) part of the DNA sequence shown in SEQ ID No. 1, or the CDS (encoding) part of the DNA sequence shown in SEQ ID No. 3, or the CDS (encoding) part of the DNA sequence shown in SEQ ID No. 8, the CDS (encoding) part of the DNA sequence shown in SEQ.ID.NO. 15.

The term "sequence identity" refers to the degree to which two polynucleotide sequences are identical on a nucleotide-by-nucleotide basis over a particular region of comparison. The term "percentage of sequence identity" is calculated by comparing two optimally aligned sequences over that region of comparison, determining the number of positions at which the identical nucleic acid base (e.g., A, T, C, G, U, or I) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Hybridization Protocol

The polynucleotides of the invention are such which have a nucleic acid sequence capable of hybridizing with the polynucleotide sequence presented as SEQ ID NO: 1, the polynucleotide sequence presented as SEQ ID NO: 3, or the polynucleotide sequence presented as SEQ ID NO: 8, or the polynucleotide sequence presented as SEQ ID NO: 15, or their complementary strand, or a sub-sequence hereof under at least medium, medium/high, or high stringency conditions, as described in more detail below.

Suitable experimental conditions for determining hybridization between a nucleotide probe and a homologous DNA or RNA sequence, involves pre-soaking of the filter containing the DNA fragments or RNA to hybridize in 5×SSC [Sodium chloride/Sodium citrate; cf. Sambrook et al.; *Molecular Cloning: A Laboratory Manual*, Cold Spring Harbor Lab., Cold Spring Harbor, N.Y. 1989] for 10 minutes, and pre-hybridization of the filter in a solution of 5×SSC, 5×Denhardt's solution [cf. Sambrook et al., Op cit.], 0.5% SDS and 100 µg/ml of denatured sonicated salmon sperm DNA [cf. Sambrook et al.; Op cit.], followed by hybridization in the same solution containing a concentration of 10 ng/ml of a random-primed [Feinberg A P & Vogelstein B; *Anal. Biochem.* 1983 132 6–13], $^{32}$P-dCTP-labeled (specific activity >1×10$^9$ cpm/µg) probe for 12 hours at approximately 45° C. The filter is then washed twice for 30 minutes in 0.1×SSC, 0.5% SDS at a temperature of at least at least 60° C. (medium stringency conditions), preferably of at least 65° C. (medium/high stringency conditions), more preferred of at least 70° C. (high stringency conditions), and even more preferred of at least 75° C. (very high stringency conditions). Molecules to which the oligonucleotide probe hybridizes under these conditions may be detected using a x-ray film.

Cloned Polynucleotides

The isolated polynucleotide of the invention may in particular be a cloned polynucleotide. As defined herein, the term "cloned polynucleotide", refers to a polynucleotide or DNA sequence cloned in accordance with standard cloning procedures currently used in genetic engineering to relocate a segment of DNA, which may in particular be cDNA, i.e. enzymatically derived from RNA, from its natural location to a different site where it will be reproduced.

Cloning may be accomplished by any suitable route and may involve techniques such as reverse transcriptase technology, PCR technology, and the like, as well as excision and isolation of the desired DNA segment.

The cloned polynucleotide of the invention may alternatively be termed "DNA construct" or "isolated DNA sequence", and may in particular be a complementary DNA (cDNA).

Biological Sources

The isolated polynucleotide of the invention may be obtained from any suitable source.

In a preferred embodiment, which the polynucleotide of the invention is cloned from, or produced on the basis of a cDNA library, e.g. of a cDNA library of the fetal or adult brain, in particular of the forebrain, the hindbrain, the cortex, the striatum, the amygdala, the cerebellum, the caudate nucleus, the corpus callosum, the hippocampus, the thalamic nucleus, the subthalamic nucleus, the olfactory nucleus, the putamen, the substantia nigra, the dorsal root ganglia, the trigeminal ganglion, the superior mesenteric artery, or the thalamus; of the spinal cord; of the heart; the placenta; of the lung; of the liver; of the skeletal muscle; of the kidney; of the liver; of the pancreas; of the intestines; of the eye; of the retina; of the tooth pulp; of the hair follicle; of the prostate; of the pituitary; or of the trachea.

Commercial cDNA libraries from a variety of tissues, both human and non-human, are available from e.g. Stratagene and Clontech. The isolated polynucleotide of the invention may be obtained by standard methods, e.g. those described in the working examples.

Neublastin Polypeptides of the Invention

As noted above, a "neublastin polypeptide," as used herein, is a polypeptide which possesses neurotrophic activity (e.g., as described in Examples 6, 7, 8, and 9) and includes those polypeptides which have an amino acid sequence that has at least 70% homology to the "neublastin" polypeptides set forth in $AA_{-95}$–$AA_{105}$ of SEQ. ID. NO. 2, $AA_1$–$AA_{105}$ of SEQ. ID. NO. 2, $AA_{-97}$–$AA_{140}$ of SEQ. ID. NO. 4, $AA_{-41}$–$AA_{140}$ of SEQ. ID. NO. 4, $AA_1$–$AA_{140}$ of SEQ. ID. NO. 4, $AA_{-80}$–$AA_{140}$ of SEQ. ID. NO. 9 ("wild type" prepro), $AA_{-41}$–$AA_{140}$ of SEQ. ID. NO.9 (pro), $AA_1$–$AA_{140}$ of SEQ. ID. NO. 5 (mature 140AA), $AA_1$–$AA_{116}$ of SEQ. ID. NO. 6 (mature 116AA), $AA_1$–$AA_{113}$ of SEQ. ID. NO. 7 (mature 113AA), $AA_1$–$AA_{140}$ of SEQ. ID. NO. 10 (mature 140AA), $AA_1$–$AA_{116}$ of SEQ. ID. NO. 11 (mature 116AA), $AA_1$–$AA_{113}$ of SEQ. ID. NO. 12 (mature 113AA), $AA_1$–$AA_{224}$ of SEQ. ID. NO. 16 (murine prepro), and variants and derivatives of each of the foregoing.

Preferably, the C-terminal sequence of the above identified neublastin polypeptides has an amino acid sequence as set forth in $AA_{72}$–$AA_{105}$ of SEQ. ID. NO. 2 (i.e., $AA_{107}$–$AA_{140}$ of SEQ. ID. NO. 9), more preferably $AA_{41}$–$AA_{105}$ of SEQ. ID. NO. 2 (i.e., $AA_{76}$–$AA_{140}$ of SEQ. ID. NO. 9).

Also, it is preferable that the neublastin polypeptide retain the 7 conserved Cys residues that are characteristic of the GDNF family and of the TGF-beta super family.

Preferably the neublastin polypeptide has an amino acid sequence greater than 85% homology, most preferably greater than 95% homology, to the foregoing sequences (i.e., $AA_{-95}$–$AA_{105}$ of SEQ. ID. NO. 2, $AA$–$AA_{105}$ of SEQ. ID. NO. 2, $AA_{-97}$–$AA_{140}$ of SEQ. ID. NO.4, $AA_{-41}$–$AA_{140}$ of SEQ. ID. NO. 4, $AA_1$–$AA_{140}$ of SEQ. ID. NO. 4, $AA_{-80}$–$AA_{140}$ of SEQ. ID. NO. 9 ("wild type" prepro), $AA_{-41}$–$AA_{140}$ of SEQ. ID. NO. 9 (pro), $AA_1$–$AA_{140}$ of SEQ. ID. NO. 5 (mature 140AA), $AA_1$–$AA_{116}$ of SEQ. ID. NO. 6 (mature 116AA), $AA_1$–$AA_{113}$ of SEQ. ID. NO. 7 (mature 113AA), $AA_1$–$AA_{140}$ of SEQ. ID. NO. 10 (mature 140AA), $AA_1$–$AA_{116}$ of SEQ. ID. NO. 11 (mature 116AA), $AA_1$–$AA_{113}$ of SEQ. ID. NO. 12 (mature 113AA), $AA_1$–$AA_{224}$ of SEQ. ID. NO. 16 (murine prepro), and preferably any of the foregoing polypeptides with a C-terminal sequence of the above identified neublastin polypeptides has an amino acid sequence as set forth in $AA_{72}$–$A_{105}$ of SEQ. ID. NO. 2 (i.e., $AA_{107}AA_{140}$ of SEQ. ID. NO. 9), more preferably $AA_{41}$–$AA_{105}$ of SEQ. ID. NO. 2 (i.e., $AA_{76}$–$AA_{140}$ of SEQ. ID. NO. 9) or $AA_{191}AA_{224}$ of SEQ. ID. NO. 16.

In addition, this invention contemplates those polypeptides which have an amino acid sequence that has at least 70% homology to the murine "neublastin" polypeptides set forth in $AA_1$–$AA_{224}$ of SEQ. ID. NO. 16.

Among the preferred polypeptides of the invention in one embodiment represent the preprosequence(as set forth in SEQ. ID. NOS. 2,4, 9, and 16, respectively),the pro sequence (as set forth in $AA_{-75}$–$AA_{105}$ of SEQ. ID. NO. 2, or $AA_{-41}$–$AA_{140}$ of SEQ.ID.NOS. 4 and 9, respectively) and the mature sequence of neublastin(as set forth in SEQ. ID. NOS. 5, 6, 7, 10, 11, or 12, preferably SEQ. ID. NOS. 10, 11, 12).

The polypeptides of the invention include variant polypeptides. In the context of this invention, the term "variant polypeptide" means a polypeptide (or protein) having an amino acid sequence that differs from the sequence presented as SEQ ID NO: 2, SEQ ID NO: 4, SEQ ID NO: 5, SEQ ID NO: 6, SEQ ID NO: 7, SEQ ID NO: 9, SEQ ID NO: 10, SEQ ID NO: 11, SEQ ID NO: 12, or SEQ ID NO: 16, at one or more amino acid positions. Such variant polypeptides include the modified polypeptides described above, as well as conservative substitutions, splice variants, isoforms, homologues from other species, and polymorphisms.

As defined herein, the term "conservative substitutions" denotes the replacement of an amino acid residue by another, biologically similar residue. For example, one would expect conservative amino acid substitutions to have little or no effect on the biological activity, particularly if they represent less than 10% of the total number of residues in the polypeptide or protein. Preferably, conservative amino acids substitutions represent changes in less than 5% of the polypeptide or protein, most preferably less than 2% of the polypeptide or protein (e.g., when calculated in accordance with NBN113, most preferred conservative substitutions would represent fewer than 3 amino acid substitutions in the wild type mature amino acid sequence). In a particularly preferred embodiment, there is a single amino acid substitution in the mature sequence, wherein the both the substituted and replacement amino acid are non-cyclic.

Other examples of particularly conservative substitutions include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like.

The term conservative substitution also include the use of a substituted amino acid residue in place of an un-substituted parent amino acid residue provided that antibodies raised to the substituted polypeptide also immunoreact with the un-substituted polypeptide.

Modifications of this primary amino acid sequence may result in proteins which have substantially equivalent activity as compared to the unmodified counterpart polypeptide, and thus may be considered functional analogous of the parent proteins. Such modifications may be deliberate, e.g. as by site-directed mutagenesis, or they may occur spontaneous, and include splice variants, isoforms, homologues from other species, and polymorphisms. Such functional analogous are also contemplated according to the invention.

Moreover, modifications of the primary amino acid sequence may result in proteins which do not retain the biological activity of the parent protein, including dominant negative forms, etc. A dominant negative protein may interfere with the wild-type protein by binding to, or otherwise sequestering regulating agents, such as upstream or downstream components, that normally interact functionally with the polypeptide. Such dominant negative forms are also contemplated according to the invention.

A "signal peptide" is a peptide sequence that directs a newly synthesized polypeptide to which the signal peptide is attached to the endoplasmic reticulum (ER) for further post-translational processing and distribution.

An "heterologous signal peptide," as used herein in the context of neublastin, means a signal peptide that is not the human neublastin signal peptide, typically the signal peptide of some mammalian protein other than neublastin. Skilled artisans will recognize that the human neublastin DNA sequence (either cDNA or genomic DNA), or sequences that differ from human neublastin DNA due to either silent codon changes or to codon changes that produce conservative amino acid substitutions, can be used to genetically modify cultured human cells so that they will overexpress and secrete the enzyme.

Polypeptides of the present invention also include chimeric polypeptides or cleavable fusion polypeptides in which another polypeptide is fused at the N-terminus or the C-terminus of the polypeptide or fragment thereof. A chimeric polypeptide may be produced by fusing a nucleic acid sequence (or a portion thereof) encoding another polypeptide to a nucleic acid sequence (or a portion thereof) of the present invention.

Techniques for producing chimeric polypeptides are standard techniques. Such techniques usually requires joining the sequences in a way so that they are in both in the same reading flame, and expression of the fused polypeptide under the control of the same promoter(s) and terminator.

Polypeptides of the present invention also include truncated forms of the full length neublastin molecule. In such truncated molecules, one or more amino acids have been deleted from the N-terminus or the C-terminus, preferably the N-terminus.

Amino Acid Sequence Homology

The degree to which a candidate polypeptide shares homology with a neublastin polypeptide of the invention is determined as the degree of identity between two amino acid sequences. A high level of sequence identity indicates a likelihood that the first sequence is derived from the second.

Homology is determined by computer analysis, such as, without limitations, the ClustalX computer alignment program [Thompson J D, Gibson T J, Plewniak F, Jeanmougin F, & Higgins D G: The ClustalX windows interface: flexible strategies for multiple sequence alignment aided by quality analysis tools; *Nucleic Acids Res.* 1997, 25 (24): 4876–82], and the default parameters suggested herein. Using this program, the mature part of a polypeptide encoded by an analogous DNA sequence of the invention exhibits a degree of identity of at least 90%, more preferred of at least 95%, most preferred of at least 98% with the amino acid sequence presented herein as SEQ ID NO: 2, SEQ. ID. NO: 4; SEQ. ID. NO.: 5; SEQ. ID. NO.: 6; SEQ. ID. NO.: 7; SEQ. ID. NO.: 9; SEQ. ID. NO.: 10; SEQ. ID. NO.: 11; SEQ. ID. NO.: 12, or SEQ. ID. NO.: 16.

Based on the homology determination it is confirmed that the polypeptide of the invention, belonging to the TGF-β superfamily, is related to the GDNF subfamily, but represents a distinct member of this subfamily.

Bioactive Polypeptides

The polypeptide of the invention may be provided on any bioactive form, including the form of pre-pro-proteins, pro-proteins, mature proteins, glycosylated proteins, phosphorylated proteins, or any other posttranslational modified protein.

The polypeptide of the invention may in particular be a N-glycosylated polypeptide, which polypeptide preferably is glycosylated at the N-residues indicated in the sequence listings.

In a preferred embodiment, the polypeptide of the invention has the amino acid sequence presented as SEQ ID NO: 9, holding a glycosylated asparagine residue at position 122; the amino acid sequence presented as SEQ ID NO: 10, holding a glycosylated asparagine residue at position 122; the amino acid sequence presented as SEQ ID NO: 11, holding a glycosylated asparagine residue at position 98; or the amino acid sequence presented as SEQ ID NO: 12, holding a glycosylated asparagine residue at position 95.

This invention also contemplates neublastin fusion proteins, such as Ig-fusions, as described, e.g., in U.S. Pat. No. 5,434,131, herein incorporated by reference.

In one embodiment, the invention provides a polypeptide having the amino acid sequence shown as SEQ ID NO: 2, or an amino acid sequence which is at least about 85%, preferably at least about 90%, more preferably at least about 98%, and most preferably at least about 99% homologous to the sequence presented as SEQ ID NO: 2.

In another embodiment, the invention provides a polypeptide having the amino acid sequence of SEQ ID NO: 4, or an amino acid sequence which is at least 90%, more preferred at least 95%, yet more preferred at least 98%, most preferred at least 99% homologous to the sequence presented as SEQ ID NO: 4.

In a third embodiment, the invention provides a polypeptide having the amino acid sequence of SEQ ID NO: 5, or an amino acid sequence which is at least 90%, more preferred at least 95%, most preferred at least 98% homologous to the sequence presented as SEQ ID NO: 5.

In a fourth embodiment, the invention provides a polypeptides having the amino acid sequence of SEQ ID NO: 6, or an amino acid sequence which is at least 90%, more preferred at least 95%, most preferred at least 98% homologous to the sequence presented as SEQ ID NO: 6.

In a fifth embodiment, the invention provides a polypeptides having the amino acid sequence of SEQ ID NO: 7, or an amino acid sequence which is at least 90%, more preferred at least 95%, most preferred at least 98% homologous to the sequence presented as SEQ ID NO: 7.

The neublastin polypeptide of the invention includes allelic variants, e.g., the polypeptide amino acid sequences of SEQ ID NOS. 5–7, in which Xaa designates Asn or Thr, and Yaa designates Ala or Pro.

In a sixth embodiment, the invention provides a polypeptides having the amino acid sequence of SEQ ID NO: 9, or an amino acid sequence which is at least 90%, more preferred at least 95%, most preferred at least 98% homologous to the sequence presented as SEQ ID NO: 9.

In a seventh embodiment, the invention provides a polypeptide having the amino acid sequence of SEQ ID NO: 10, or an amino acid sequence at least 90%, more preferred at least 95%, most preferred at least 98%, homologous to the sequence presented as SEQ ID NO: 10.

In a eight embodiment, the invention provides a polypeptide having the amino acid sequence of SEQ ID NO: 11, or an amino acid sequence at least 90%, more preferred at least 95%, most preferred at least 98% homologous to the sequence presented as SEQ ID NO: 11.

In a ninth embodiment, the invention provides a polypeptide having the amino acid sequence of SEQ ID NO: 12, or an amino acid sequence at least 90%, more preferred at least 95%, most preferred at least 98% homologous to the sequence presented as SEQ ID NO: 12.

In a tenth embodiment, the invention provides a polypeptide having the amino acid sequence of SEQ ID NO: 16, or an amino acid sequence at least 90%, more preferred at least 95%, most preferred at least 98% homologous to the sequence presented as SEQ ID NO: 16, which is a pre-pro-neublastin of murine origin.

In another embodiment, the polypeptide of the invention holds the GDNF subfamily fingerprint, i.e. the amino acid residues underlined in Table 3.

In a further embodiment, the invention provides a polypeptide encoded by a polynucleotide sequence capable of hybridizing under high stringency conditions with the polynucleotide sequence presented as SEQ ID NO: 1, its complementary strand, or a subsequence thereof. In a preferred embodiment, the polypeptide of the invention is encoded by a polynucleotide sequence being at least 70% homologous to the polynucleotide sequence presented as SEQ ID NO: 1. In its most preferred embodiment, the polypeptide of the invention is encoded by the polynucleotide sequence presented as SEQ ID NO: 1.

In a yet further embodiment, the invention provides novel polypeptides encoded by a polynucleotide sequence capable of hybridizing under high stringency conditions with the polynucleotide sequence presented as SEQ ID NO: 3, its complementary strand, or a subsequence thereof. In a preferred embodiment, the polypeptide of the invention is encoded by a polynucleotide sequence being at least 70% homologous to the polynucleotide sequence presented as SEQ ID NO: 3. In its most preferred embodiment, the polypeptide of the invention is encoded by the polynucleotide sequence presented as SEQ ID NO: 3.

In a still further embodiment, the invention provides novel polypeptides encoded by a polynucleotide sequence capable of hybridizing under high stringency conditions with the polynucleotide sequence presented as SEQ ID NO: 8, its complementary strand, or a subsequence thereof. In a preferred embodiment, the polypeptide of the invention is encoded by a polynucleotide sequence being at least 70% homologous to the polynucleotide sequence presented as SEQ ID NO: 8. In its most preferred embodiment, the polypeptide of the invention is encoded by the polynucleotide sequence presented as SEQ ID NO: 8.

In a still further embodiment, the invention provides novel polypeptides encoded by a polynucleotide sequence capable of hybridizing under high stringency conditions with the polynucleotide sequence presented as SEQ ID NO: 15, its complementary strand, or a sub-sequence thereof. In a preferred embodiment, the polypeptide of the invention is encoded by a polynucleotide sequence being at least 70% homologous to the polynucleotide sequence presented as SEQ ID NO: 15. In its most preferred embodiment, the polypeptide of the invention is encoded by the polynucleotide sequence presented as SEQ ID NO: 15.

Biological Origin

The polypeptide of the invention may be isolated from mammalian cells, preferably from a human cell or from a cell of murine origin.

In a most preferred embodiment, the polypeptide of the invention may be isolated from human heart tissue, from human skeletal muscle, from human pancreas, or from human brain tissue, in particular from caudate nucleus or from thalamus, or it may be obtained from DNA of mammalian origin, as discussed in more detail below.

Neurotrophic Activity

Neublastin polypeptides of the invention are useful for moderating metabolism, growth, differentiation, or survival of a nerve or neuronal cell. In particular, neublastin polypeptides are used to treating or to alleviate a disorder or disease of a living animal, e.g., a human, which disorder or disease is responsive to the activity of a neurotrophic agents. Such treatments and methods are described in more details below.

Antibodies

Neublastin polypeptides or polypeptide fragments of the invention are used to produce neublastin-specific antibodies. As used herein, a "neublastin-specific antibody is an antibody, e.g., a polyclonal antibody or a monoclonal antibody, that is immunoreactive to a neublastin polypeptide or polypeptide fragment, or that binds with specificity to an epitopes of a neublastin polypeptides.

The preparation of polyclonal and monoclonal antibodies is well known in the art. Polyclonal antibodies may in particular be obtained as described by, e.g., Green et al.,: "Production of Polyclonal Antisera" in *Immunochemical Protocols* (Manson, Ed.); Humana Press, 1992, pages 1–5; by Coligan et al.,: "Production of Polyclonal Antisera in Rabbits, Rats, Mice and Hamsters" in *Current Protocols in Immunology,* 1992, Section 2.4.1, and by Ed Harlow and David Lane (Eds.) in "Antibodies; A laboratory manual" Cold Spring Harbor Lab. Press 1988. These protocols are hereby incorporated by reference. Monoclonal antibodies may in particular be obtained as described by, e.g., Kohler & Milstein, *Nature,* 1975, 256:495; Coligan et al., in *Current Protocols in Immunology,* 1992, Sections 2.5.1–2.6.7; and Harlow et al., in *Antibodies: A Laboratory Manual;* Cold Spring Harbor, Pub., 1988, page 726; which protocols are hereby incorporated by reference.

Briefly, monoclonal antibodies may be obtained by injecting, e.g., mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce the antibodies to the antigen, and isolating the antibodies from the hybridoma cultures.

Monoclonal antibodies can be isolated and purified from hybridoma cultures by a variety of well-established techniques, including affinity chromatography with protein A Sepharose, size-exclusion chromatography, and ion-exchange chromatography, see. e.g. Coligan et al. in *Current Protocols in Immunology*, 1992, Sections 2.7.1–2.7.12, and Sections 2.9.1–2.9.3; and Barnes et al.: "Purification of Immunoglobulin G (IgG)" in *Methods in Molecular Biology*; Humana Press, 1992, Vol. 10, Pages 79–104. Polyclonal or monoclonal antibodies may optionally be further purified, e.g. by binding to and elution from a matrix to which the polypeptide, to which the antibodies were raised, is bound.

Antibodies which bind to the neublastin polypeptide of the invention can be prepared using an intact polypeptide or fragments containing small peptides of interest as the immunising antigen. The polypeptide used to immunise an animal may be obtained by recombinant DNA techniques or by chemical synthesis, and may optionally be conjugated to a carrier protein. Commonly used carrier proteins which are chemically coupled to the peptide include keyhole limpet hemocyanin (KLH), thyroglobulin, bovine serum albumin (BSA), and tetanus toxoid. The coupled peptide may then be used to immunise the animal, which may in particular be a mouse, a rat, a hamster or a rabbit.

In one embodiment, antibodies are produced using the following peptides: Peptide 1: CRPTRYEAVSFMDVNST (amino acids 108–124 of SEQ ID NO: 9); or Peptide 2: ALRPPPGSRPVSQPC (amino acids 93–107 of SEQ ID NO: 9). Methods for producing antibodies using these polypeptides are described in Example 10.

We also generated rabbit polyclonal antibodies to the following peptides:

Peptide R27: GPGSRARAAGARGC (amino acids 30–43 of SEQ ID NO:9);

Peptide R28: LGHRSDELVRFRFC (amino acids 57–70 of SEQ ID NO:9);

Peptide R29: CRRARSPHDLSL (amino acids 74–85 of SEQ ID NO:9);

Peptide R30: LRPPPGSRPVSQPC (amino acids 94–107 of SEQ ID NO:9); and

Peptide R31: STWRTVDRLSATAC (amino acids 123–136 of SEQ ID NO:9).

Of this group, only peptides R30 and R31, relatively close to the C-terminus, recognized the denatured protein under reducing conditions on a Western blot.

We have also identified additional neublastin-derived peptides derived from the mature protein, as detailed below, which are predicted surface exposed loops based on the known GDNF structure (Eigenbrot and Gerber, Nat. Struct. Biol., 4, pp. 435–438 (1997)), and are thus useful for antibody generation:

Region 1: CRLRSQLVPVRALGLGHRSDELVRFRFC (AA43–70 of SEQ. ID. NO: 9)

Region 2: CRRARSPHDLSLASLLGAGALRPPPGSRPVSQPC (AA74–107 of SEQ. ID. NO: 9)

Region 3: CRPTRYEAVSFMDVNSTWRTVDRLSATAC (AA108–136 of SEQ. ID. NO: 9)

In another aspect of the invention, antibodies which specifically bind neublastin or neublastin-derived peptides may be used for detecting the presence of such neublastin neurotrophic factors in various media, and in particular for the diagnosis of conditions or diseases associated with the neublastin molecules of the invention. A variety of protocols for such detection, including ELISA, RIA and FACS, are known in the art.

The antibodies of this invention may also be used for blocking the effect of the eurotrophic factor, and may in particular be neutralizing antibodies.

Methods of Producing the Polypeptides of the Invention

A cell comprising a DNA sequence encoding a neublastin polypeptide of the invention is cultured under conditions permitting the production of the polypeptide, followed by recovery of the polypeptide from the culture medium, as detailed below. When cells are to be genetically modified for the purposes of producing a neublastin polypeptide, the cells may be modified by conventional methods or by gene activation.

According to conventional methods, a DNA molecule that contains a neublastin cDNA or genomic DNA sequence may be contained within an expression construct and transfected into cells by standard methods including, but not limited to, liposome-, polybrene-, or DEAE dextran-mediated transfection, electroporation, calcium phosphate precipitation, microinjection, or velocity driven microprojectiles ("biolistics"). Alternatively, one could use a system that delivers DNA by viral vector. Viruses known to be useful for gene transfer include adenoviruses, adeno-associated virus, lentivirus, herpes virus, mumps virus, poliovirus, retroviruses, Sindbis virus, and vaccinia virus such as canary pox virus, as well as Baculovirus infection of insect cells, in particular SfP9 insect cells.

Alternatively, the cells may be modified using a gene activation ("GA") approach, such as described in U.S. Pat. Nos. 5,733,761 and 5,750,376, each incorporated herein by reference.

Accordingly, the term "genetically modified," as used herein in reference to cells, is meant to encompass cells that express a particular gene product following introduction of a DNA molecule encoding the gene product and/or regulatory elements that control expression of a coding sequence for the gene product. The DNA molecule may be introduced by gene targeting, allowing incorporation of the DNA molecule at a particular genomic site.

Recombinant Expression Vectors

In a further aspect the invention provides a recombinant expression vector comprising the polynucleotide of the invention. The recombinant expression vector of the invention may be any suitable eukaryotic expression vector. Preferred recombinant expression vectors are the ubiquitin promoter containing vector pTEJ-8 (*FEBS Lett.* 1990 267 289–294), and derivatives hereof, e.g. pUbi1Z. A preferred commercially available eukaryotic expression vectors is e.g. the virus promoter containing vector pcDNA-3 (available from Invitrogen). Another preferred expression vector uses SV40 early and adenovirus major late promoters (derived from plasmid pAD2beta; Norton and Coffin, Mol. Cell. Biol. 5: 281 (1985)).

This invention also provides prokaryotic expression vectors and synthetic genes (syngenes) with codon optimization for prokaryotic expression. Syngenes were constructed with lower GC content and preferred bacterial (e.g., *E. coli*) codons. The syngene is being cloned into two vectors, pET19b and pMJB164, a derivative of pET19b. The construction with pET19b is shown in FIG. 14. In this construct, the sequence encoding the mature domain of neublastin is directly fused to an initiating methionine. The construction with pMJB 164 is shown in FIG. 15.

Production Cells

In a yet further aspect the invention provides a production cell genetically manipulated to comprise the isolated polynucleotide sequence of the invention, and/or or a recombinant expression vector of the invention. The cell of the invention may in particular be genetically manipulated to transiently or stably express, over-express or co-express polypeptide of the invention. Methods for generating transient and stable expression are known in the art.

The polynucleotide of the invention may be inserted into an expression vector, e.g. a plasmid, virus or other expression vehicle, and operatively linked to expression control sequences by ligation in a way that expression of the coding sequence is achieved under conditions compatible with the expression control sequences. Suitable expression control sequences include promoters, enhancers, transcription terminators, start codons, splicing signals for introns, and stop codons, all maintained in the correct reading frame of the polynucleotide of the invention so as to permit proper translation of mRNA. Expression control sequences may also include additional components such as leader sequences and fusion partner sequences.

The promoter may in particular be a constitutive or an inducible promoter. When cloning in bacterial systems, inducible promoters such as pL of bacteriophage λ, plac, ptrp, ptac (ptrp-lac hybrid promoter), may be used. When cloning in mammalian systems, promoters derived from the genome of mammalian cells, e.g. the ubiquitin promoter, the TK promoter, or the metallothionein promoter, or from mammalian viruses, e.g. the retrovirus long terminal repeat, the adenovirus late promoter or the vaccinia virus 7.5K promoter, may be used. Promoters obtained by recombinant DNA or synthetic techniques may also be used to provide for transcription of the polynucleotide of the invention.

Suitable expression vectors typically comprise an origin of expression, a promoter as well as specific genes which allow for phenotypic selection of the transformed cells, and include vectors like the T7-based expression vector for expression in bacteria [Rosenberg et al; *Gene* 1987 56 125], the pTEJ-8, pUbi1Z, pcDNA-3 and pMSXND expression vectors for expression in mammalian cells [Lee and Nathans, *J. Biol. Chem.* 1988 263 3521], baculovirus derived vectors for expression in insect cells, and the oocyte expression vector PTLN [Lorenz C, Pusch M & Jentsch T J: Heteromultimeric CLC chloride channels with novel properties; *Proc. Natl. Acad. Sci. USA* 1996 93 13362–13366].

In a preferred embodiment, the cell of the invention is an eukaryotic cell, e.g., a mammalian cell, e.g., a human cell, an oocyte, or a yeast cell. The cell of the invention may be without limitation a human embryonic kidney (HEK) cell, e.g., a HEK 293 cell, a BHK21 cell, a Chinese hamster ovary (CHO) cell, a *Xenopus laevis* oocyte (XLO) cell. In another embodiment, the cell of the invention is a fungal cell, e.g., a filamentous fungal cell. In another preferred embodiment, the cell is an insect cell, most preferably the Sf9 cell. Additional preferred mammalian cells of the invention are PC12, HiB5, RN33b cell lines and human neural progenitor cells. Most preferred are human cells.

Examples of primary or secondary cells include fibroblasts, epithelial cells including mammary and intestinal epithelial cells, endothelial cells, formed elements of the blood including lymphocytes and bone marrow cells, glial cells, hepatocytes, keratinocytes, muscle cells, neural cells, or the precursors of these cell types. Examples of immortalized human cell lines useful in the present methods include, but are not limited to, Bowes Melanoma cells (ATCC Accession No. CRL 9607), Daudi cells (ATCC Accession No. CCL 213), HeLa cells and derivatives of HeLa cells (ATCC Accession Nos. CCL 2, CCL 2.1, and CCL 2.2), HL-60 cells (ATCC Accession No. CCL 240), HT-1080 cells (ATCC Accession No. CCL 121), Jurkat cells (ATCC Accession No. TIB 152), KB carcinoma cells (ATCC Accession No. CCL 17), K-562 leukemia cells (ATCC Accession No. CCL 243), MCF-7 breast cancer cells (ATCC Accession No. BTH 22), MOLT-4 cells (ATCC Accession No. 1582), Namalwa cells (ATCC Accession No. CRL 1432), Raji cells (ATCC Accession No. CCL 86), RPMI 8226 cells (ATCC Accession No. CCL 155), U-937 cells (ATCC Accession No. CRL 1593), WI-38VA13 sub line 2R4 cells (ATCC Accession No. CLL 75.1), and 2780AD ovarian carcinoma cells (Van der Blick et al., *Cancer Res.* 48: 5927–5932, 1988), as well as heterohybridoma cells produced by fusion of human cells and cells of another species. Secondary human fibroblast strains, such as WI-38 (ATCC Accession No. CCL 75) and MRC-5 (ATCC Accession No. CCL 171), may also be used.

When the cell of the invention is an eukaryotic cell, incorporation of the heterologous polynucleotide of the invention may be in particular be carried out by infection (employing a virus vector), by transfection (employing a plasmid vector), using calcium phosphate precipitation, microinjection, electroporation, lipofection, or other physical-chemical methods known in the art.

In a more preferred embodiment the isolated polynucleotide sequence of the invention, and/or or a recombinant expression vector of the invention are transfected in a mammalian host cell, a neural progenitor cell, an astrocyte cell, a T-cell, a hematopoitic stem cell, a non-dividing cell, or a cerebral endothelial cell, comprising at least one DNA molecule capable of mediating cellular immortalization and/or transformation.

Activation of an endogenous gene in a host cell may be accomplished by the introducing regulatory elements, in particular by the introducing a promoter capable of effecting transcription of an endogenous gene encoding the neublastin polypeptide of the invention.

Pharmaceutical Compositions

In another aspect the invention provides novel pharmaceutical compositions comprising a therapeutically effective amount of the polypeptide of the invention.

For use in therapy the polypeptide of the invention may be administered in any convenient form. In a preferred embodiment, the polypeptide of the invention is incorporated into a pharmaceutical composition together with one or more adjuvants, excipients, carriers and/or diluents, and the pharmaceutical composition prepared by the skilled person using conventional methods known in the art.

Such pharmaceutical compositions may comprise the polypeptide of the invention, or antibodies hereof. The composition may be administered alone or in combination with at one or more other agents, drugs or hormones.

The pharmaceutical composition of this invention may be administered by any suitable route, including, but not limited to, oral, intravenous, intramuscular, inter-arterial, intramedullary, intrathecal, intraventricular, transdermal, subcultaneous, intraperitoneal, intranasal, anteral, topical, sublingual or rectal application, buccal, vaginal, intraorbital, intracerebral, intracranial, intraspinal, intraventricular, intracisternal, intracapsular, intrapulmonary, transmucosal, or via inhalation.

Intrapulmonary delivery methods, apparatus and drug preparation are described, for example, in U.S. Pat. Nos. 5, 785, 049, 5,780,019, and 5,775,320, each incorporated herein by reference. Administration may be by periodic injections of a bolus of the preparation, or may be made more continuous by intravenous or intraperitoneal administration from a reservoir which is external (e.g., an IV bag) or internal (e.g., a bioerodable implant, a bioartificial organ, or a colony of implanted neublastin production cells). See, e.g., U.S. Pat. Nos. 4,407,957, 5,798,113, and 5,800,828, each incorporated herein by reference. Intrapulmonary delivery methods and apparatus are described, for example, in U.S. Pat. Nos. 5,654,007, 5,780,014, and 5,814,607, each incorporated herein by reference.

In particular, administration of a neublastin according to this invention may be achieved using any suitable delivery means, including:

(a) pump (see, e.g., *Annals of Pharmacotherapy*, 27:912 (1993); *Cancer*, 41:1270 (1993); *Cancer Research*, 44:1698 (1984), incorporated herein by reference), (b) microencapsulation (see, e.g., U.S. Pat. Nos. 4,352,883; 4,353,888; and 5,084,350, herein incorporated by reference), (c) continuous release polymer implants (see, e.g., Sabel, U.S. Pat. No. 4,883,666, incorporated herein by reference), (d) macroencapsulation (see, e.g., U.S. Pat. Nos. 5,284,761, 5,158,881, 4,976,859 and 4,968,733 and published PCT patent applications WO92/19195, WO 95/05452, each incorporated herein by reference);

(e) naked or unencapsulated cell grafts to the CNS (see, e.g., U.S. Pat. Nos. 5,082,670 and 5,618,531, each incorporated herein by reference); or (f) injection, either subcutaneously, intravenously, intra-arterially, intramuscularly, or to other suitable site;

(g) oral administration, in capsule, liquid, tablet, pill, or prolonged release formulation.

In one embodiment of this invention, a neublastin is delivered directly into the CNS, preferably to the brain ventricles, brain parenchyma, the intrathecal space or other suitable CNS location, most preferably intrathecally.

In another preferred embodiment, we contemplate systemic delivery by subcutaneous injection, intravenous administration, or intravenous infusion.

Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch.

Further details on techniques for formulation and administration may be found in the latest edition of *Remington's Pharmaceutical Sciences* (Maack Publishing Co., Easton, Pa.).

The active ingredient may be administered in one or several doses per day. Currently contemplated appropriate dosages are between 0.5 ng neublastin/kg body weight to about 50 µg/kg per administration, and from about 1.0 ng/kg to about 100 µg/kg daily. The neublastin pharmaceutical composition should provide a local concentration of neurotrophic factor of from about 5 ng/ml cerebrospinal fluid ("CSF") to 25 ng/ml CSF.

The dose administered must of course be carefully adjusted to the age, weight and condition of the individual being treated, as well as the route of administration, dosage form and regimen, and the result desired, and the exact dosage should of course be determined by the practitioner.

In further embodiments, the Neublastin polypeptide of the invention may be administered by genetic delivery, using cell lines and vectors as described below under methods of treatment. To generate such therapeutic cell lines, the polynucleotide of the invention may be inserted into an expression vector, e.g. a plasmid, virus or other expression vehicle, and operatively linked to expression control sequences by ligation in a way that expression of the coding sequence is achieved under conditions compatible with the expression control sequences. Suitable expression control sequences include promoters, enhancers, transcription terminators, start codons, splicing signals for introns, and stop codons, all maintained in the correct reading frame of the polynucleotide of the invention so as to permit proper translation of mRNA. Expression control sequences may also include additional components such as leader sequences and fusion partner sequences.

The promoter may in particular be a constitutive or an inducible promoter. Constitutive promoters could be synthetic, viral or derived from the genome of mammalian cells, e.g. the human ubiquitin promoter. In a preferred embodiment the therapeutic cell line will be a human immortalised neural cell line expressing the polypeptide of the invention. For implantation, we contemplate implanting between about $10^5$ to $10^{10}$ cells, more preferably $10^6$ to about $10^8$ cells.

Methods of Treatment

The present invention, which relates to polynucleotides and proteins, polypeptides, peptide fragments or derivatives produced therefrom, as well as to antibodies directed against such proteins, peptides or derivatives, may be used for treating or alleviating a disorder or disease of a living animal body, including a human, which disorder or disease is responsive to the activity of neurotrophic agents.

The polypeptides of the present invention may be used directly via, e.g., injected, implanted or ingested pharmaceutical compositions to treat a pathological process responsive to the neublastin polypeptides.

The polynucleotide of the invention, including the complementary sequences thereof, may be used for the expression of the neurotrophic factor of the invention. This may be achieved by cell lines expressing such proteins, peptides or derivatives of the invention, or by virus vectors encoding such proteins, peptides or derivatives of the invention, or by host cells expressing such proteins, peptides or derivatives. These cells, vectors and compositions may be administered to treatment target areas to affect a disease process responsive to the neublastin polypeptides.

Suitable expression vectors may be derived from lentiviruses, retroviruses, adenoviruses, herpes or vaccinia viruses, or from various bacterially produced plasmids may be used for in vivo delivery of nucleotide sequences to a whole organism or a target organ, tissue or cell population. Other methods include, but are not limited to, liposome transfection, electroporation, transfection with carrier peptides containing nuclear or other localizing signals, and gene delivery via slow-release systems. In still another aspect of the invention, "antisense" nucleotide sequences complementary to the neublastin gene or portions thereof, may be used to inhibit or enhance neublastin expression.

In yet another aspect the invention relates to a method of treating or alleviating a disorder or disease of a living animal body, including a human, which disorder or disease is responsive to the activity of neurotrophic agents.

The disorder or disease may in particular be damages of the nervous system caused by trauma, surgery, ischemia, infection, metabolic diseases, nutritional deficiency, malignancy or toxic agents, and genetic or idiopathic processes.

The damage may in particular have occurred to sensory neurons or retinal ganglion cells, including neurons in the dorsal root ganglion or in any of the following tissues: The geniculate, petrosal and nodose ganglia; the vestibuloacoustic complex of the VIIth cranial nerve; the ventrolateral pole of the maxillomandribular lobe of the trigeminal ganglion; and the mesencephalic trigeminal nucleus.

In a preferred embodiment of the method of the invention, the disease or disorder is a neurodegenerative disease involving lesioned and traumatic neurons, such as traumatic lesions of peripheral nerves, the medulla, and/or the spinal cord, cerebral ischaemic neuronal damage, neuropathy and especially peripheral neuropathy, peripheral nerve trauma or injury, ischemic stroke, acute brain injury, acute spinal cord injury, nervous system tumors, multiple sclerosis, exposure to neurotoxins, metabolic diseases such as diabetes or renal dysfunctions and damage caused by infectious agents, neurodegenerative disorders including Alzheimer's disease, Huntington's disease, Parkinson's disease, Parkinson-Plus syndromes, progressive Supranuclear Palsy (Steele-Richardson-Olszewski Syndrome), Olivopontocerebellar Atrophy (OPCA), Shy-Drager Syndrome (multiple systems atrophy), Guamanian parkinsonism dementia complex, amyotrophic lateral sclerosis, or any other congenital or neurodegenerative disease, and memory impairment connected to dementia.

In a preferred embodiment, we contemplate treatment of sensory and/or autonomic system neurons. In another preferred embodiment, we contemplate treatment of motor neuron diseases such as amyotrophic lateral sclerosis ("ALS") and spinal muscular atrophy. In yet another preferred embodiment, we contemplate use of the neublastin molecules of this invention to enhance nerve recovery following traumatic injury. In one embodiment we contemplate use of a nerve guidance channel with a matrix containing neublastin polypeptides. Such nerve guidance channesl are disclosed, e.g., U.S. Pat. No. No. 5,834,029, incorporated herein by reference.

In a preferred embodiment, the polypeptides and nucleic acids of this invention (and pharmaceutical compositions containing same) are used in the treatment of peripheral neuropathies. Among the peripheral neuropathies contemplated for treatment with the molecules of this invention are trauma-induced neuropathies, e.g., those caused by physical injury or disease state, physical damage to the brain, physical damage to the spinal cord, stroke associated with brain damage, and neurological disorders related to neurodegeneration.

We also contemplate treatment of chemotherapy-induced neuropathies (such as those caused by delivery of chemotherapeutic agents, e.g., taxol or cisplatin); toxin-induced neuropathies, drug-induced neuropathies, vitamin-deficiency-induced neuropathies; idiopathic neuropathies; and diabetic neuropathies. See, e.g., U.S. Pat. Nos. 5,496, 804 and 5,916,555, each herein incorporated by reference.

We also contemplate treatment of mon-neuropathies, mono-multiplex neuropathies, and poly-neuropathies, including axonal and demyelinating neuropathies, using the neublastin nucleotides and polypeptides of this invention.

In another preferred embodiment, the polypeptides and nucleic acids of this invention (and pharmaceutical compositions containing same) are used in the treatment of various disorders in the eye, including photoreceptor loss in the retina in patients afflicted with macular degeneration, retinitis pigmentosa, glaucoma, and similar diseases.

Another object of the present invention is to provide a method for the prevention of the degenerative changes connected with the above diseases and disorders, by implanting into mammalian brain including human vectors or cells capable of producing a biologically active form of neublastin or a precursor of neublastin, i.e. a molecule that can readily be converted to a biologically active form of neublastin by the body, or additionally cells that secrete neublastin may be encapsulated, e.g. into semipermeable membranes.

Cells can be grown in vitro for use in transplantation or engraftment into mammalian brain including human.

In a preferred embodiment, the gene encoding the polypeptide of the invention is transfected into a suitable cell line, e.g. into an immortalised rat neural stem cell line like HiB5 and RN33b, or into a human immortalised neural progenitor cell line, and the resulting cell line is implanted in the brain of a living body, including a human, to secrete the therapeutic polypeptide of the invention in the CNS, e.g. using the expression vectors described in International Patent Application WO 98/32869.

Methods of Diagnosis and Screening

A neublastin nucleic acid can be used to determine whether an individual is predisposed to developing a neurological disorder resulting from a defect in the neublastin gene, e.g., an defect in a neublastin allele, which has been acquired by, e.g., genetic inheritance, by abnormal embryonic development, or by acquired DNA damage. The analysis can be by, e.g., detecting a deletion(s) or a point-mutation (s) within the neublastin gene, or by detecting the inheritance of such predisposition of such genetic defects with specific restriction fragment length polymorphisms (RFLPs), by detecting the presence or absence of a normal neublastin gene by hybridizing a nucleic acid sample from the patient with a nucleic acid probe(s) specific for the neublastin gene, and determining the ability of the probe to hybridize to the nucleic acid.

In particular, a neublastin nucleic acid can be used as a hybridization probe. Such hybridization assays may be used to detect, prognose, diagnose, or monitor the various conditions, disorders, or disease states associated with aberrant levels of the mRNAs encoding the Neublastin protein. A neublastin nucleic acid can be construed as a "marker" for neublastin neurotrophic factor-dependant physiological processes. These processes include, but are not limited to, "normal" physiological processes (e.g., neuronal function) and pathological processes (e.g., neurodegenerative disease). The characterization of a particular patient sub-population(s) with aberrant (i.e., elevated or deficient) levels of the neublastin protein and or neublastin-encoding mRNA may lead to new disease classifications. By "aberrant levels," as defined herein, is meant an increased or decreased level relative to that in a control sample or individual not having the disorder determined by quantitative or qualitative means.

The neublastin nucleic acids and polypeptides of this invention may also be used to screen for and identify neublastin analogs, including small molecule mimetics of neublastin. In one contemplated embodiment, the invention provides a method for identifying a candidate compound that induces a neuroblastin-mediated biological effect, the method comprising the steps of providing a test cell which when contacted with neublastin is induced to express a detectable product, exposing the cell to the candidate compound, and detecting the detectable product. The expression of the detectable product is indicative of the ability of the candidate compound to induce the neuroblastin-mediated biological effect.

Further, the neublastin nucleic acids and polypeptides of this invention may be used on DNA chip or protein chips,or in computer programs to identify related novel gene sequences and proteins encoded by them, including allelic variants and single nucleotide polymorphisms ("SNPs"). Such methods are described, e.g., in U.S. Pat. No. Nos. 5,795,716; 5,754,524; 5,733,729; 5,800,992; 5,445,934; 5,525,464, each herein incorporated by reference.

EXAMPLES

Example 1

Methods for Isolating Neublastin Nucleic Acids
Method 1: Rapid-Screening of Human Fetal Brain cDNA for the Neublastin Gene A 290 bp fragment was identified in two high throughput genomic sequences (HGTS) submitted to GenBank (Accession No. AC005038 and AC00505 1) by its homology to human persephin. From the nucleic acid sequence of the 290 bp fragment, two neublastin specific primers were synthesized. The neublastin top strand primer ("NBNint.sence") had the sequence 5'-CCT GGC CAG CCT ACT GGG-3' (SEQ. ID. NO.: 17). The neublastin bottom strand primer ("NBNint.antisence") had the sequence 5'-AAG GAG ACC GCT TCG TAG CG-3' (SEQ. ID. NO.: 18). With these primers, 96-well PCR reactions were performed.

A 96-well master plate, containing plasmid DNA from 500,000 cDNA clones, was loaded with approximately 5000 clones per well. A 96-well sub-plate was utilized with E. coli DH10B glycerol stock containing 50 clones per well.

A neublastin nucleic acid was identified by three rounds of amplification using polymerase chain reaction ("PCR") techniques; amplification increases the number of copies of the nucleic acid in the sample.

Master Plate Screening: Using the 96-well PCR screening technique described above, a human fetal brain cDNA master plate was screened with the gene-specific primers to isolate the human neublastin cDNA.

Thirty nanograms (30 ng) of human fetal brain cDNA (6 ng/μl; Origene Technologies) was obtained from the corresponding well of the master plate and placed in a total volume of 25 μl which contained the following reagents: 0.2 mM of each of the two aforementioned gene-specific primers (i.e., NBNint.sence and NBNint.antisence), 1×standard PCR buffer (Buffer V, Advanced Biotechnologies, UK), 0.2 mM dNTPs (Amersham-Pharmacia), 0.1 M GC-Melt (Clontech Laboratories, USA); and 0.5 units of Taq DNA polymerase (5 U/μl; Advanced Biotechnologies, UK).

PCR thermocycling reactions were performed using the following procedure and conditions. DNA was initially denatured at 94° C. for 3 minutes, and then followed by 35 cycles of denaturation at 94° C. for 1 minute each, annealing at 55° C. for 1 minute, a first extension at 72° C. for 90 seconds; and a final extension at 72° C. for 5 minutes. The products of 96 individual PCR reactions were analysed by gel electrophoresis using a 2% agarose gel containing ethidium bromide stain. The 102 bp, positive PCR product seen from a well was found to correspond to a unique 96-well sub-plate.

The 102 bp nucleic acid fragment had the following sequence [SEQ ID NO. 13]:

5'-CCTGGCCAGCCTACTGGGCGCCGGGGC CCTGCGACCGCCCCGGGCTCCCGGCCCGTCA GCCAGCCCTGCTGCCGACCCACGCGCTACGAA GCGGTCTCCTT-3'

Sub-Plate Screening: The 96-well human fetal brain sub-plate was screened by PCR-mediated amplification by placing 1 μl of the glycerol stock from the corresponding sub-plate well in a total volume of 25 μl which contained: 0.2 mM of each of the two gene-specific primers; 1×standard PCR buffer (Buffer V; Advanced Biotechnologies, UK); 0.2 mM dNTPs (Amersham-Pharmacia); 0.1 M GC-Melt (Clontech Laboratories, USA); and 0.5 units of Taq DNA polymerase (5 U/μl; Advanced Biotechnologies, UK).

The same PCR thermocycling conditions as described for the masterplate screening were utilized. The 96 individual PCR reactions were analysed on a 2% agarose gel containing ethidium bromide and a positive well was identified which gave the 102 bp PCR fragment.

Colony PCR: One ml of the glycerol stock from the positive sub-plate well was diluted 1:100 in Luria broth (LB). One ml and 10 ml of the aforementioned dilution were then plated on two separate agar plates containing Luria broth ("LB"), and 100 μg/ml carbenicillin. The LB plates were then incubated overnight at 30° C. From these plates, 96 colonies were picked into a new 96-well PCR plate containing: 0.2 mM of each of the two aforementioned gene-specific primers, 1×standard PCR buffer (Buffer V; Advanced Biotechnologies, UK), 0.2 mM dNTPs (Amersham-Pharmacia), 0.1 M GC-Melt (Clontech Laboratories, USA), and 0.5 units of Taq DNA polymerase (5 U/μl; Advanced Biotechnologies, UK) in a final volume of 25 μl.

The same PCR thermocycling conditions as described for the masterplate screening were utilized. The 96 individual PCR reactions were then analysed on a 2% agarose gel containing ethidium bromide. A positive colony containing the 102 bp fragment was subsequently identified.

Sequencing of the plasmid DNA prepared from this positive colony revealed a full-length cDNA of 861 bp [SEQ ID NO: 8]. The cDNA coded for a pre-pro-neublastin [SEQ ID NO: 9]. Automated DNA sequencing was performed using the BigDye® terminator cycle sequencing kit (PE Applied Biosystems, USA). The sequencing gels were run on the ABI Prism 377 (PE Applied Biosystems, USA).

Method 2: Cloning Neublastin cDNA from Human Brain

An additional method of amplifying the full-length neublastin cDNA or cDNA fragment can be performed by RACE (Rapid Amplification of cDNA ends) and the neublastin-specific primers NBNint.sence and NBNint.antisence described above, combined with vector-specific or adapter-specific primers, for example by using the Marathon cDNA amplification kit (Clontech Laboratories, USA, Cat. No. K1802-1).

Whole human brain Marathon-Ready cDNA (Clontech Laboratories, USA, Catalogue. No. 7400-1) can be used to amplify the full-length neublastin cDNA. Useful primers for amplification include a neublastin top strand primer 5'-ATGGAACTTGGACTTGG-3' (SEQ ID NO.: 19) ("NBNext.sence"), and a neublastin bottom strand primer 5'-TCCATCACCCACCGGC-3' (SEQ ID NO.: 20) ("NBNext.antisence"), combined with the adaptor primer AP1 included with the Marathon-Ready cDNA. An alternative top strand primer has also been used, 5'-CTAGGAGCCCATGCCC-3' (SEQ ID NO.: 28). A further alternative bottom strand primer, 5'-GAGCGAGCCCTCAGCC-3' (SEQ ID NO.: 33) may also be used. Likewise, alternative bottom strand primers SEQ ID NOS.: 24 and 26 may also be used.

Method 3: Cloning Neublastin cDNA from Human Brain

Another method of cloning neublastin cDNA is by screening human adult or fetal brain libraries with one or more neublastin probes described herein (and as exemplified in FIG. 1). These libraries include: λgt11 human brain (Clontech Laboratories, USA, Cat. No. HL3002b); or λgt11 human fetal brain (Clontech Laboratories, USA, Cat. No. HL3002b).

Method 4: Rapid-Screening of Mouse Fetal cDNA for the Neublastin Gene

A rapid screening procedure for the neublastin gene was performed in the following manner. A 96-well master plate, containing plasmid DNA from 500,000 cDNA clones, was loaded with approximately 5000 clones per well. A 96-well sub-plate was utilized with E. Coli glycerol stock containing 50 clones per well. Three rounds of PCR-mediated amplification was performed in order to identify a gene of interest (i.e., neublastin).

Master Plate Screening: A mouse fetal cDNA master plate was screened by 96-well PCR using gene-specific primers to isolate the mouse neublastin cDNA. The following two primers were synthesised:

(1) neublastin C2 primer (NBNint.sence):
5'-GGCCACCGCTCCGACGAG-3' (SEQ ID NO: 21);

and (2) neublastin C2as primer (NBNint.antisence): 5'-GGCGGTCCACGGTTCTCCAG-3'(SEQ ID NO: 22). By using these two gene-specific primers a 220 bp positive PCR product was identified. The 220 bp nucleic acid possessed the following sequence [SEQ ID NO. 14]:

5'-GGCCACCGCTCCGACGAGCTGATACGTTTC
CGCTTCTGCAGCGGCTCGTGCCGCCGAGCA
CGCTCCCAGCACGATCTCAGTCTGGCCAGC
CTACTGGGCGCTGGGGCCCTACGGTCGCCT
CCCGGGTCCCGGCCGATCAGCCAGCCCTGC
TGCCGGCCCACTCGCTATGAGGCCGTCTCC
TTCATGGACGTGAACAGCACCTGGAGAACC
GTGGACCGCC-3'

96-well PCR reactions were then performed in the following manner. Thirty nanograms of mouse fetal brain cDNA (6 ng/µl; Origene Technologies) was obtained from the corresponding well of the master plate and placed in a total volume of 25 µl which also contained: 0.2 mM of each of the two aforementioned gene-specific primers (i.e., C2 primer (NBNint.sence) and neublastin C2as primer (NBNint.antisence)), 1×standard PCR buffer (Buffer V; Advanced Biotechnologies, UK), 0.2 mM dNTPs (Amersham-Pharmacia), 0.1 M GC-Melt (Clontech Laboratories, USA), and 0.5 units of Taq DNA polymerase (5 U/µl; Advanced Biotechnologies, UK).

The following PCR thermocycling conditions were utilized: an initial denaturation at 94° C. for 3 minutes, followed by 35 cycles of denaturation at 94° C. for 1 minute each, annealing at 55° C. for 1 minute, extension at 72° C. for 90 seconds; and a final extension at 72° C. for 5 minutes. The 96 individual PCR reactions were analysed on a 2% agarose gel containing ethidium bromide stain. The 220 bp, positive PCR product seen from a well was found to correspond to a unique 96-well sub-plate. The 96 individual PCR reactions were then analysed by gel electrophoresis on a 2% agarose gel containing ethidium bromide stain. The 220 bp positive PCR product which had been identified corresponded to a unique well of the 96-well sub-plate.

Sub-Plate Screening: The 96-well mouse fetal sub-plate was screened by PCR-mediated amplification by placing 1 µl of the glycerol stock from the corresponding sub-plate well into a final, total volume of 25 µl which contained: 0.2 mM of each of the two aforementioned gene-specific primers; 1×standard PCR buffer (Buffer V; Advanced Biotechnologies, UK); 0.2 mM dNTPs (Amersham-Pharmacia); 0.1 M GC-Melt (Clontech. Laboratories, USA); and 0.5 units of Taq DNA polymerase (5 U/µl; Advanced Biotechnologies, UK). The PCR thermocycling was performed according to the conditions described above for the master plate screening.

The individual 96 PCR reactions were then analysed on a 2% agarose gel containing ethidium bromide and a positive well was identified which produced the 220 bp fragment.

Colony PCR: One ml of the glycerol stock from the positive sub-plate well was diluted 1:100 in Luria broth (LB). One ml and 10 ml of the aforementioned dilution were then plated on two separate LB plates, containing 100 µg/ml carbenicillin, and incubated at 30° C. overnight. A total of 96 colonies were isolated and transferred to a 96-well PCR plate containing: 0.2 mM of each of the two aforementioned gene-specific primers, 1×standard PCR buffer (Buffer V; Advanced Biotechnologies, UK), 0.2 mM dNTPs (Amersham-Pharmacia); 0.1 M GC-Melt (Clontech Laboratories, USA), and 0.5 units of Taq DNA polymerase (5 U/µl; Advanced Biotechnologies UK) in a final volume of 25 µl.

PCR thermocycling was performed according to the conditions described above (see, "master plate screening", infra). The 96 individual PCR reactions were analysed by gel electrophoresis on a 2% agarose gel containing ethidium bromide. A positive colony was identified by the presence of the 220 bp fragment. Plasmid DNA was prepared from this positive colony. The clone was sequenced by automated DNA sequencing using the BigDye® terminator cycle sequencing kit with AmpliTaq DNA polymerase. The sequencing gels were run on the ABI Prism 377 (PE Applied Biosystems). The resulting sequence of this clone revealed a full-length cDNA of 2136 bp (SEQ ID NO: 15). The cDNA includes an open reading frame with the predicted amino acid sequence shown in SEQ ID NO: 16, which codes for a mouse pre-pro-neublastin polypeptide.

Example 2

Cloning of Genomic Neublastin

As discussed above, applicants identified a 290 bp nucleic acid fragment in two human BAC clones with entries in GenBank (with the Accession Nos. AC005038 and AC00505 1) which had regions of homology to persephin and to the flanking sequences of persephin. Applicants used the 861 bp predicted sequence described above to design additional primers, with the goal of cloning a nucleic acid encoding additional neublastin nucleic acids using Lasergene Software (DNAStar, Inc.). Two pairs of primers were used to clone the neublastin gene by using PCR reactions on genomic DNA. The two pairs of primers are illustrated below.

Primer Pair No. 1
  5' CCA AgC CCA CCT ggg TgC CCT CTT TCT CC 3' (sense) (SEQ ID NO:23).
  5' CAT CAC CCA CCg gCA ggg gCC TCT CAg 3' (antisense) (SEQ ID NO:24).

Primer Pair No. 2
  5' gAgCCCAtgCCCggCCTgATCTCAgCCCgA ggACA 3' (sense) (SEQ ID NO:25).
  5' CCCTggCTgAggCCgCTggCTAgTgggACTCTgC 3' (antisense) (SEQ ID NO:26).

Using primer pair No. 1, a 887 bp DNA fragment was amplified from a preparation of human genomic DNA purchased from Clontech Laboratories, (Cat. No. 6550–1).

PCR protocol: PCR was performed using the Expand™ High Fidelity PCR system (Boehringer Mannheim) with buffer 1. The PCR reaction mixture was supplemented with 5% dimethylsulfoxide (DMSO) and 17.5 pmol of each dNTP in a total volume of 50 µl. Thermocycling was performed with a pre-denaturation step at 94° C. for 2 minutes, followed by 35 two-step cycles at 94° C. for 10 seconds, and 68° C. for 1 minute, respectively. Thermocycling was terminated by incubation at 68° C. for 5 minutes. Thermocycling was carried out in a PTC-225 DNA Engine Tetrad thermocycler (MJ Research, MA). The PCR products were analysed by gel electrophoresis on 2% agarose (FMC) and then photographed.

The 887 bp fragment amplified from human genomic DNA with primer pair No. 1 was cloned into the pCRII vector (Invitrogen), and transformed into XL 1-Blue competent E.coli cells (Stratagene). The resulting plasmid, designated neublastin-2, was sequenced using Thermosequenase (Amersham Pharmacia Biotech). Sequencing products were analysed by electrophoreses on an ALFExpress automated sequencer (Amersham Pharmacia Biotech).

Fragments obtained by PCR amplification of human genomic DNA with the second pair of primers (Primer Pair No. 1, above), were sequenced, revealing an additional 42 bp region at the 3' prime end of the open reading frame. The full-length sequence was analysed by comparing it to the sequences of nucleic acids of other neurotrophic factors, as well as by mapping exon-intron boundaries using gene-finding software programs which identify probable splice junctions and regions of high coding potential using Netgene and Gene Mark software (Brunak et al., *J.Mol. Biol.*, 220, pp. 49–65 (1991); Borodovsky et al., Nucl. Acids Res., 23, pp. 3554–62 (1995). The exon-intron boundaries were confirmed by the cDNA obtained from the Rapid Screen described above.

Figure 7:
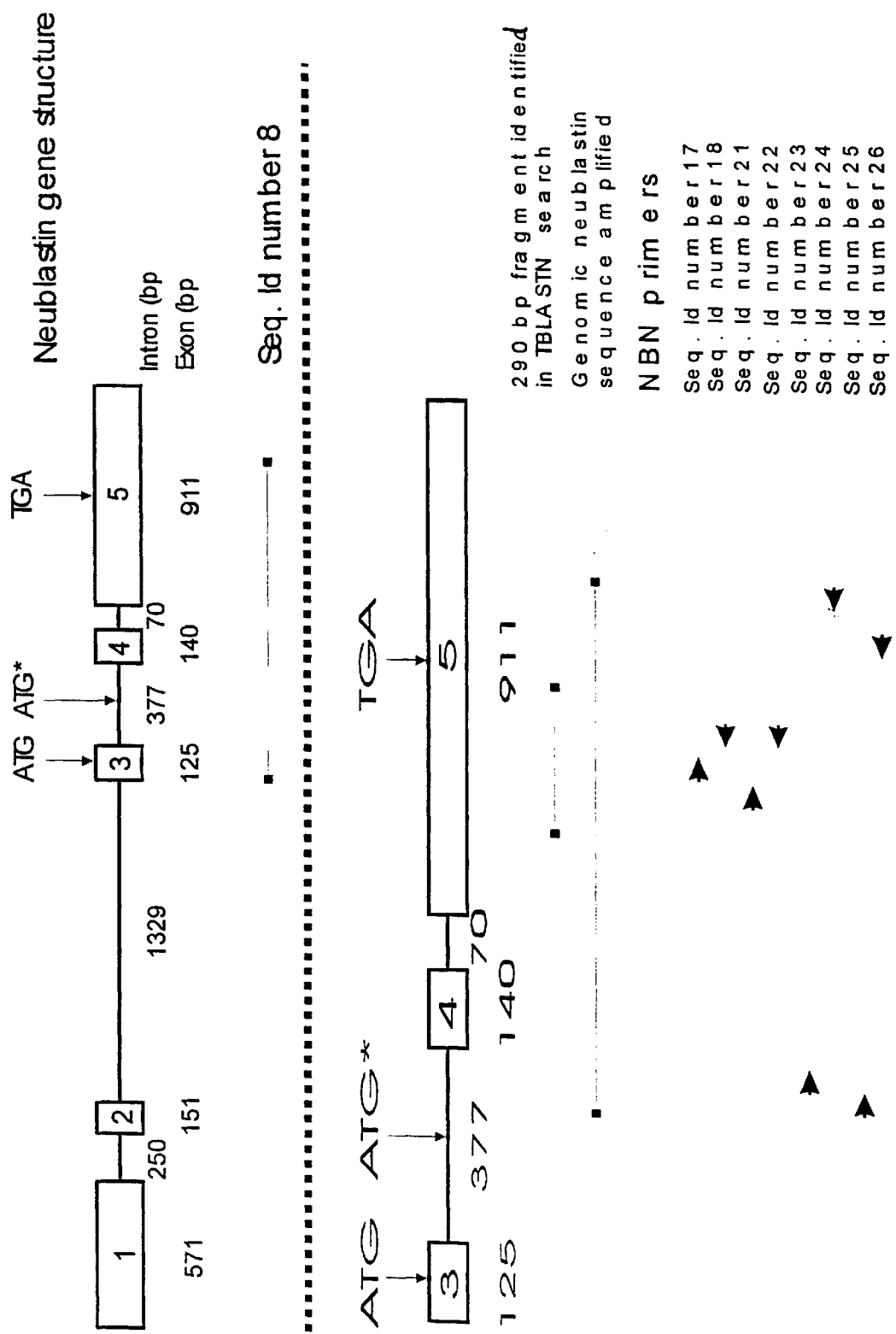
FIG. 7 is a schematic diagram of the genomic structure of the neublastin gene, including the nucleic acid primers which can be used to identify the full length neublastin gene, and their spatial orientation in relation to the genomic Neublastin-encoding sequence (i.e., gene).

As illustrated in FIG. 7, the resulting neublastin gene has two exons separated by a 70 bp intron. Together, the exons have a predicted amino acid sequence of a full-length Neublastin polypeptide. The predicted cDNA (SEQ ID NO: 3) contains an open reading frame (ORF) encoding 238 amino acid residues (SEQ ID NO: 4). The Neublastin-2 clone contained the complete coding sequence of pro-neublastin. The amino acid sequence encoded by the gene showed high homology to three proteins, persephin, neurturin, and GDNF.

Example 3

Expression of Neublastin Nucleic Acids

Expression of neublastin RNA was detected in both nervous and non-nervous tissue in rodents and in humans, and at various developmental immature and adult stages, using the techniques described below.

Method of detecting Neublastin RNA expression using RT-PCR: Based on the neublastin DNA sequence identified as SEQ ID NO: 1, the following primers were synthesised: (1) a neublastin C2 primer 5'-GGCCACCGCTCCGACGAG-3' (SEQ ID NO: 21), and (2) a neublastin C2 as primer 5'-GGCGGTCCACGGTTCTCCAG-3' (SEQ ID NO: 22). This primer set was used to RT-PCR amplify a DNA fragment from adult and fetal human whole-brain mRNA. Among the DNA fragments produced by this reaction was one of 220 bp. Identification of this 220 bp DNA fragment confirmed that the neublastin gene is expressed in adult and fetal brain tissue. A 220 bp DNA fragment was also amplified from genomic DNA with using these primers.

Method of detecting Neublastin RNA expression by northern blot hybridization: Northern blots with polyA$^+$ RNA from adult human tissue were purchased from a commercial supplier (Clontech Laboratories, USA) and probed with a $^{32}$P-labeled neublastin cDNA. The labelled neublastin cDNA was prepared according to the methods described in Example 1, above.

Preparation of Probes: A neublastin nucleic acid DNA fragment (nucleotides 296–819 of SEQ ID NO: 8) was labelled by the Rediprime II labelling kit (Amersham; Cat. No. RPN1633) for use as a hybridization probe, as recommended by the manufacturer. Briefly, the DNA sample was diluted to a concentration of 2.5–25 ng in 45 µl of 10 mM TE Buffer (10 mM Tris-HCl, pH 8.0, 1 mM EDTA). The DNA was then denatured by heating the sample to 95–100° C. for 5 minutes in a boiling water bath, quick cooling the sample by placing it on ice for 5 minutes, and then briefly centrifuging it to bring the contents to the bottom of the reaction tube. The total amount of denatured DNA was added together with 5 µl of Redivue [$^{32}$P] dCTP (Amersham Pharmacia Biotech Ltd.) in the reaction tube containing buffered solution of dATP, dGTP, dTTP, exonuclease free Klenow enzyme and random primer in dried stabilised form. The solution was mixed by pipetting up and down 2 times, moving the pipette tip around in the solution, and the reaction mixture was incubated at 37° C. for 10 minutes. The labelling reaction was stopped by adding 5 µl of 0.2 M EDTA. For use as a hybridization probe the labelled DNA was denatured to single strands by heating the DNA sample to 95–100° C. for 5 minutes, then snap cooling the DNA sample on ice for 5 minutes. The tube was centrifuged and its contents mixed well. Finally the single-stranded DNA probe was purified using the Nucleotide Removal Kit (Qiagen).

Hybridization Techniques: Prepared northern blots were purchased from a commercial supplier ("Multiple Tissue Northern Blots, Clontech Laboratories, USA, Catalogue Nos. 7760-1 and 7769-1) and were hybridized according to the manufacturer's instructions using the neublastin $^{32}$P-labeled probe prepared above. For hybridization, ExpressHyb Solution (Clontech Laboratories, USA) was used, and a concentration of approximately 3 ng/ml of the labelled probe was employed. The ExpressHyb solution was heated to 68° C. and then stirred to dissolve any precipitate. Each northern blot membrane (10×10 cm) was pre-hybridized in at least 5 ml of ExpressHyb Solution at 68° C. for 30 minutes in a Hybaid Hybridization Oven according to the manufacturer's instructions. The neublastin $^{32}$P-labeled probe was denatured at 95–100° C. for 2 minutes and then chilled quickly on ice. Fourteen microliters (14 µl) of the labelled probe was added to 5 ml of fresh ExpressHyb, and thoroughly mixed. The ExpressHyb Solution used in the pre-hybridization was replaced by evenly distributing over the blots the 5 ml of fresh ExpressHyb Solution containing labelled DNA probe. Blots were incubated at 68° C. for 1 hour in a Hybaid hybridization Oven. After incubation, the blots were rinsed and washed several times at low stringency (2×SSC buffer containing 0.05% SDS at room temperature) followed by a high stringency wash (0.1×SSC containing 0.1% SDS at 50° C.) [20×SSC is 0.3 M NaCl/0.3 M Na citrate, pH 7.0]. The blots were exposed to a Hyperfilm MP (Amersham Pharmacia Biotech Ltd.) at −80° C. using intensifying screens.

The results of the northern blot hybridization experiments are presented in FIG. 1. FIG. 1A (left) and FIG. 1B (right) are northern blots of polyA$^+$ RNA which were probed with $^{32}$P-labelled neublastin cDNA as described in Example 3. The markers represent polynucleotides of 1.35 kilobase pairs ("kb"), 2.4 kb, 4.4 kb, 7.5 kb, and 9.5 kb in size. The membrane of FIG. 1A was prepared with mRNA extracted from various adult human tissues: From the results of the northern blot hybridization analysis, applicants conclude that neublastin mRNA is expressed in many adult human tissues. The highest level of neublastin expression is detected in the heart, in skeletal muscle and in the pancreas. The membrane of FIG. 1B was prepared with RNA extracted from various regions of the adult human brain. Within the adult brain, the highest level of expression is seen in the caudate nucleus and in the thalamus. An mRNA transcript of approximately 5 kb was the predominant form of neublastin mRNA expressed in the brain.

Method of Detecting Neublastin RNA Expression Using by in situ Hybridization in Tissues The following techniques are used to measure the expression of neublastin RNA in animal tissues, e.g., rodent tissues, with a neublastin anti-sense probe.

Expression in Mice

Preparation of Tissue Samples: Time pregnant mice (B&K Universal, Stockholm, Sweden) were killed by cervical dislocation on gestational day 13.5 or 18.5. Embryos were removed by dissection under sterile conditions, and immediately immersed in a solution of 0.1M phosphate buffer (PB) containing 4% paraformaldehyde ("PFA") for 24–30 hours, and then removed from the PFA and stored in PBS. The tissue was prepared for sectioning by immersing the tissue in a solution of 30% sucrose, and then embedding it in TissueTech (O.C.T. Compound, Sakura Finetek USA, Torrance, Calif.). Six series of coronal or sagittal sections (12 µm each) were cut on a cryostat and thaw mounted onto positively charged glass slides. Neonatal heads/brains (P1, P7) were fixed following the same protocol as for the embryonic stages, and adult brain tissue was dissected, immediately frozen on dry ice, and cut on a cryostat without any prior embedding.

Preparation of Neublastin Riboprobes: An antisense neublastin RNA probe (hereafter a "neublastin riboprobe") was made as follows. Nucleotides 1109–1863 of the mouse neublastin cDNA sequence (SEQ ID NO: 15) were subcloned into the BlueScript vector (Stratagene). The resulting plasmid was cut into a linear DNA using EcoRI restriction endonuclease. The EcoRI DNA fragment was in vitro transcribed with T3 RNA polymerase and the digoxigenin ("DIG") RNA Labelling Kit according to the manufacturer's instructions (Boehringer Mannheim).

Hybridization: Cryostat sections were fixed for 10 minutes in 4% PFA, treated for 5 minutes with 10 mg/ml of proteinase K, dehydrated sequentially in 70% and 95% ethanol for 5 and 2 min, respectively, and then allowed to air dry. Hybridization buffer (50% deionized formamide, 10% of a 50% dextran sulphate solution, 1% Denhardt's solution, 250µg/ml yeast tRNA, 0.3M NaCl, 20 mM Tris-HCl (pH8), 5 mM EDTA, 10 mM NaPO$_4$, 1% sarcosyl) containing 1 µg/ml of the DIG-labelled probe was heated to 80° C. for 2 minutes and applied onto the sections. The sections was then covered with parafilm and incubated at 55° C. for 16–18 hours.

The next day the sections were washed at high stringency (2×SSC containing 50% formamide) at 55° C. for 30 minutes, and then washed in RNase buffer and incubated with 20µg/ml of RNaseA for 30 minutes at 37° C. In order to detect the DIG-labelled probe, sections were pre-incubated in blocking solution (PBS containing 0.1% Tween-20 and 10% heat-inactivated goat serum) for 1 hour and then incubated over night at 4° C. with a 1:5000 dilution of alkaline-phosphatase-coupled anti-DIG antibody (Boehringer Mannheim). The following day, each section was given four, two-hour washes in PBS containing 0.1% Tween-20, and then given two ten-minute washes in NTMT buffer (100 mM NaCl, 100 mM Tris-HCl (pH9.5), 50 mM MgCl$_2$, 0.1% Tween-20). The sections were then incubated in BM-purple substrate containing 0.5mg/ml of levamisole for 48 hours. The color reaction was stopped by washing in PBS. The sections were air dried and covered with cover-slip with DPX (KEBO-lab, Sweden).

The results of the in situ hybridization reactions are presented in Table 1.

TABLE 1

Expression of neublastin in Mice

| Structure | E13.5 | E18.5 | P1 | P7 | Adult |
|---|---|---|---|---|---|
| Forebrain | ++ | | | | |
| Ventral Midbrain | – | | | | |
| Dorsal Root ganglia | ++ | | | | |
| Spinal chord | + | | | | |
| Retina | | +++ | +++ | + | |
| Olfactory bulb | | ++ | ++ | ++ | |
| Tooth pulp | | ++ | ++ | + | |
| Trigeminal ganglia | | ++ | ++ | ++ | |
| Striatum | | + | + | ++ | |
| Cortex | | ++ | ++ | ++ | + |
| Dentate gyrus | | | | ++ | + |

As shown in Table 1, at embryonic day 13.5 ("E3.5"), neublastin was expressed in the spinal chord and in the hindbrain, and weakly in the forebrain. Neublastin expression was also detected in the developing retina and in the sensory ganglia (dorsal root ganglia and trigeminal ganglia (V)). Outside the nervous system, a weak signal was found in the kidney, the lung and the intestine, indicating that neublastin is also expressed in those tissues.

At embryonic day 18.5 ("E18.5"), neublastin was expressed most prominently in the trigeminal ganglion (V). Neublastin expression was also detected in the retina, the striatum, and the cortex. In addition, expression was seen in tooth anlage.

Again referring to Table 1, increased neublastin expression, from the E18.5 time-point to postnatal days 1 and 7, was seen in the cortex, the striatum and the trigeminal ganglion (V). Neublastin expression was more prominent in the outer layers of the cortex than in the inner layers of the cortex. On P7, expression was found in the same structures as at day 1 but in addition neublastin expression was found in the hippocampus, especially in the dentate gyrus and in the cerebellum. In the adult murine brain, neublastin was strongly expressed in dentate gyrus, with very low or undetectable levels of neublastin expression detected other tissues tested.

Expression in Rat

The following experiment describes the hybridization of rat tissues with a alkaline-phosphatase-labelled oligodeoxynucleotide neublastin anti-sense probe.

Preparation of tissue samples: Rat embryos (E14) were obtained from pregnant Wistar rats (Møllegård, Denmark) following pentobarbital anaesthesia. Postnatal rats (P0, P7, adult) were killed by decapitation. Dissected brains and whole heads were immediately immersed in cold 0.9% NaCl, fresh frozen and sectioned at 20 µm on a cryostat (coronal and sagittal sections, 10 series).

In situ hybridization: Two series of sections were hybridized using an anti-sense alkaline-phosphatase (AP) conjugated oligodeoxynucleotide probe (5'-NCA GGT GGT CCG TGG GGG GCG CCA AGA CCG G-3' (SEQ ID NO:27), Oligo. No. 164675, DNA Technology, Denmark,). This probe is complementary to bases 1140 to 1169 of the mouse neublastin cDNA of SEQ ID NO: 15).

Prior to hybridization, the sections were air dried at room temperature, heated at 55° C. for 10 min., and then treated with 96% ethanol at 4° C. overnight. The sections were then air dried and incubated in hybridization medium (5.0 pmol probe/ml) overnight at 39 ° C. (Finsen et al., 1992, *Neurosci.* 47:105–113; West et al., 1996, *J. Comp. Neurol.* 370:11–22).

Post-hybridization treatment consisted of four, thirty-minute rinses in 1×SSC (0.15M NaCl, 0.015 M Na-citrate) at 55° C., followed by three ten-minute rinses in Tris-HCl, pH 9.5 at room temperature prior to applying AP developer. AP developer was prepared immediately before use and contained nitroblue tetrazoleum (NBT, Sigma), 5-bromo, 4-chloro, 3-indolylphosphate (BCIP, Sigma), and Tris-HCl-MgCl$_2$ buffer, pH 9.5 (Finsen et al., *Neurosci.* 1992 47 105–113). AP development took place in the dark at room temperature for 48 hours. The color reaction was stopped by rinsing the sections in destilled water. The sections were dehydrated in graded acetone, softened in xylene-phenol creosote (Allchem, UK), cleared in xylene, and coverslipped using Eukitt (Bie & Berntsen, Denmark).

Control reactions consisted of (1) pre-treating the sections with RNase A (50 µg/ml, Pharmacia, Sweden) prior to hybridization; (2) hybridizing the sections with a hundred-fold excess of unlabelled probe; and (3) hybridizing the sections with hybridization buffer alone. The results of the hybridization reactions are presented in Table 2.

TABLE 2

Expression of neublastin in rats

| Structure | E14 | P0/P1 | P7 | Adult |
|---|---|---|---|---|
| Forebrain | ++ | | | |
| Ventral Midbrain | − | | | |
| Dorsal root ganglia | ++ | | | |
| Spinal cord | + | | | |
| Retina | + | | | |
| Olfactory bulb | (+) | ++ | ++ | |
| Cerebellum | | + | ++ | + |
| Trigeminal ganglia | | ++ | ++ | |
| Striatum | | + | +(+) | |
| Cortex | (+) | ++ | ++ | + |
| Hippocampus | | (+) | ++ | ++ |

At embryonic day 14 (E14), neublastin was weakly expressed in rat embryos in the forebrain, in the hindbrain, and in the spinal cord. Neublastin mRNA was also detected in the eye (retina), dorsal root ganglia, the trigeminal ganglia (V), and in the kidneys, lungs, heart, liver, and intestines. In newborn (P0) rats there was marked neublastin expression in the cortex and in the striatum. Neublastin expression was also detected in the olfactory bulb and in the hippocampus. In 7-day-old (P7) rats, neublastin was expressed in the cortex, the striatum, the olfactory bulb, and in the cerebellum. A marked signal was seen in the hippocampus. In adult rats, very low or undetectable levels of neublastin expression were detected in most areas of the brain. Weak signals were detected in the thalamic nucleus, and marked neublastin expression was detected in the hippocampus.

Example 4

Neublastin Polypeptides

The open reading frame, or coding region (CDS), identified in SEQ ID NO: 8 encodes the pre-pro-polypeptide (designated "pre-pro-neublastin"). The amino acid sequence predicted from this open reading frame is shown in SEQ ID NO: 9. Based on SEQ ID NO: 9, three variants of neublastin polypeptides were identified. These variants include: (i) the polypeptide designated herein as NBN140, which possesses the amino acid sequence designated as SEQ ID NO: 10; (ii) the polypeptide designated herein as NBN116, which possesses the amino acid sequence designated as SEQ ID NO: 11; and (iii) the polypeptide designated herein as NBN113, which possesses the amino acid sequence designated as SEQ ID NO: 12.

Similarly, based on the coding region (CDS) as identified in SEQ ID NO: 3, which encodes the pre-pro-polypeptide possessing the amino acid sequence (designated as SEQ ID NO: 4), three variants of neublastin were identified. These variants include: (i) the polypeptide which possesses the amino acid sequence designated as SEQ ID NO: 5; (ii) the polypeptide which possesses the amino acid sequence designated as SEQ ID NO: 6; and (iii) the polypeptide which possesses the amino acid sequence designated as SEQ ID NO: 7.

Based on a Clustal W (1.75)-based multiple sequence alignment, SEQ ID NO: 9 was aligned with the amino acid sequences of GDNF, persephin and neurturin. This alignment is illustrated in Table 3.

TABLE 3

Amino Acid Sequence Comparison of Neublastin (SEQ ID NO:35) to Persephin (SEQ ID NO:36), Neurturin (SEQ ID NO:34), and GDNF (SEQ ID NO:37)

```
Neurturin-full    -------------------MQRWKAAALASVLCSSVLSIWMCREGLLLSHRLGPA
Neublastin        MELGLGGLSTLSHCPWPRRQPALWPTLAALALLSSVAEASLGSAPRSPAPREGPPP
Persephin-full    -------------------------------------------------------
GDNF_HUMAN-full   -----MKLWDVVAVCLVLLHTASAFPLPAGKRPPEAPAEDRSLGRRRAPFALSSDS
Neurturin-full    LVPLHRLPRTLDARIARLAQYRALLQGAPDAMELRELTPWAGRPPGPRRRAGPRRR
Neublastin        VLASPAGHLPGGRTARWCSGRARRPPPQPSRPAPPPPAPPSALPRGGRAARAGGPG
Persephin-full    -MAVGKFLLGSLLLLSLQLGQGWGPDARGVPVADGEFSSEQVAKAGGTWLGTHRPL
GDNF_HUMAN-full   NMPEDYPDQFDDVMDFIQATIKRLKRSPDKQMAVLPRRERNRQAAAANPENSRGKG
Neurturin-full    RARARLGARPCGLRELEVRVSELGLGYASDETVLFRYCAGACEA-AARVYDLGLRR
Neublastin        SRAAAAGARGCRLRSQLVPVRALGLGHRSDELVRFRFCSGSCRR-ARSPHDLSLAS
Persephin-full    ARLRRALSGPCQLWSLTLSVAELGLGYASEEKVIFRYCAGSCPRGARTQHGLALAR
GDNF_HUMAN-full   RRGQRGKNRGCVLTAIHLNVTDLGLGYETKEELIFRYCSGSCDA-AETTYDKILKN
                   *  *    :  *  ****:  :.*  : **:*:*:*    *    :.   *
Neurturin-full    LRQRRRLRRE---RVRAQPCCRPTAYEDEVSFLDAHSRYHTVHELSARECACV-
Neublastin        LLGAGALRPPPGSRPVSQPCCRPTRYE-AVSFMDVNSTWRTVDRLSATACGCLG
Persephin-full    LQGQGPAHGG--------PCCRPTRYT-DVAFLDDRHRWQRLPQLSAAACGCGG
GDNF_HUMAN-full   LSRNRRLVSD----KVGQACCRPIAFDDDLSFLDDNLVYHILRKHSAKRCGCI-
                   *            .****  :    ::*:*  .  :: :  .  **   *.*
```

*indicates positions which have a single, fully conserved residue.
:indicates that one of the following 'strong' groups is fully conserved:
-STA,NEQK,NHQK,NDEQ,QHRK,MILV,MILF,HY,FYW.
.indicates that one of the following 'weaker' groups is fully conserved:
-CSA,ATV,SAG,STNK,STPA,SGND,SNDEQK,NDEQHK,NEQHRK,VLIM, HFY.

From the amino acid sequence alignment shown in Table 3, it can be seen that neublastin has seven conserved cysteine residues at locations that are conserved within the TGF-β superfamily. In one embodiment, the preferred neuroblastin polypeptide contains (seven) cysteines conserved as in SEQ ID NO: 2 at positions 8, 35, 39, 72, 73, 101 and 103, or as in SEQ ID NOS: 4 and 9 at positions 43, 70, 74, 107, 108, 136 and 138. These seven conserved cysteine residues are known within the TGF-b superfamily to form three intra-monomeric disulfide bonds (contemplated, e.g., in SEQ ID NO: 2 between cysteine residues 8–73, 35–101, and 39–103, and, e.g., in SEQ ID NOS: 4 and 9 between cysteine residues 43–108, 70–136, and 74–138) and one intermonomeric disulfide bond (contemplated, e.g., in SEQ ID NO: 2 between cysteine residues 72–72, and, e.g., in SEQ ID NOS: 4 and 9 between cysteine residues 107–107), which together with the extended beta strand region constitutes the conserved structural motif for the TGF-b superfamily. See, e.g., Daopin et al., *Proteins* 1993 17 176–192.

Based on this sequence alignment, neublastin was shown to be a member of the GDNF subfamily of neurotrophic factors (LGLG-FR(Y/F)CSGSC-QxCCRP-SAxxCGC, the GDNF subfamily fingerprint, underlined in Table 3).

The homology of neublastin to other members of the GDNF family was calculated, and the results are presented Table 4, below.

$^{32}$P-labelled neublastin cDNA of the present invention as described infra). The blot was prepared by total RNA extracted from untransfected HiB5 cells, HiB5pUbi1zNBN22 cells and HiB5pUbi1zGDNF14, respectively, as indicated. The positions of the 28S and 18S rRNA bands corresponding to 4.1 kb and 1.9 kb, respectively, are indicated on the blot.

TABLE 4

Homology of Neublastin Polypeptides to other members of the GDNF Family

| | Mature Protein NBN140 | | | | Mature Protein NBN113 | | | |
|---|---|---|---|---|---|---|---|---|
| | Homology | | | Homology of full length peptides Identity | Homology | | | Homology of full length peptides Identity |
| Neurotrophic Factor | Identity | Overlap (aa) | Strong Homology | | Identity | Overlap (aa) | Strong Homology | |
| GDNF | 34% (47/137) | 137 | 45% (67/137) | 31.9% | 36% (41/111) | 111 | 52% (59/111) | 29.5% |
| NTN | 48% (61/127) | 127 | 56% (72/127) | 36.9% | 49% (56/114) | 114 | 57% (66/114) | 44.7% |
| PSP | 44% (55/125) | 125 | 56% (71/125) | 36.9 | 45% (51/111) | 111 | 57% (65/111) | 44.3% |
| IHA | 31% (25/81) | 81 | — | 25.2% | 31% (25/81) | 81 | — | 22.5% |
| TGF-β2 | 23% (17/73) | 73 | — | 18.5% | 23% (17/73) | 73 | — | 20.2% |

GDNF = Glial cell line Derived Neurotrophic Factor
NTN = Neurturin
PSP = Persephin
IHA = Inhibin-α
TF-β2 = Transforming Growth Factor-β2
Strong homology indicates that one of the following "strong" groups are conserved: STA, NEQK, NHQK, NDEQ, QHRK, MILV, MILF, HY, FYW.

Example 5

Production of Neublastin

We have produced neublastin in both eukaryotic and prokaryotic cells, as described below.

Expression Vectors The full length cDNA encoding neublastin was inserted into the eukaryotic expression vector pUbi1Z. This vector was generated by cloning the human UbC promoter into a modified version of pcDNA3.1/Zeo. The unmodified pcDNA3.1/Zeo is commercially available (Invitrogen). The modified pcDNA3.1/Zeo is smaller than the parent vector, because the ampicillin gene (from position 3933 to 5015) and a sequence from position 2838 to 3134 were removed. In this modified version of pcDNA3.1/Zeo, the CMV promoter was replaced with the UbC promoter from pTEJ-8 (Johansen et al., *FEBS Lett.* 1990 267 289–294), resulting in pUbi1Z.

Figure 2:
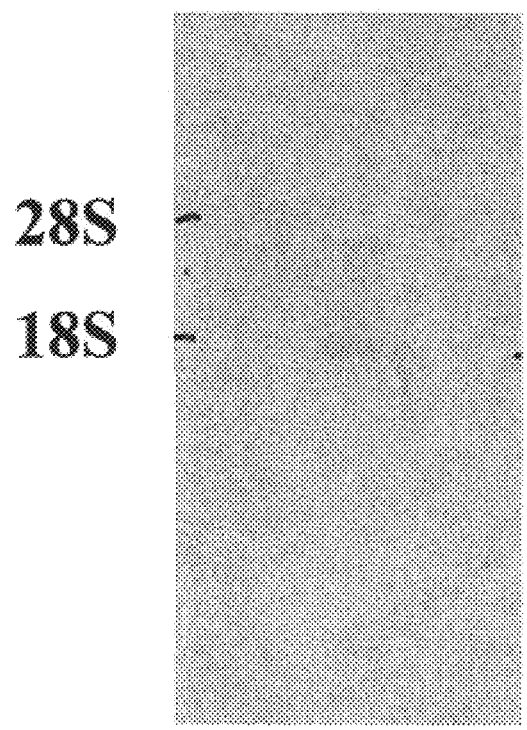
FIG. 2 is a photographic image of a northern blot probed with $^{32}$P-labelled neublastin cDNA, comparing the amount of neublastin cDNA expressed in a non-transfected cell-line, HiB5, with the amount of neublastin cDNA expressed in a cell-line transfected with neublastin cDNA, and with a cell-line transfected with GDNF-cDNA.

Mammalian Cell Expression The pUbi1Z vector which contained neublastin coding sequences was then transfected into the mammalian cell line HiB5, which is an immortalised rat neural cell line (Renfranz et al., *Cell,* 66, pp. 713–729 (1991)). Several HiB5 cell lines stably expressing neublastin (as determined by RT-PCR) have been established. In one of these stable cell lines, HiB5pUbi1zNBN22 expression was confirmed by hybridizing total RNA on a Northern blot with a $^{32}$P-labelled neublastin probe. The results of these studies are shown in FIG. 2. HiB5pUbi1zNBN22 was then used as a source of neublastin for studies of neublastin neurotrophic activity.

Figure 3:
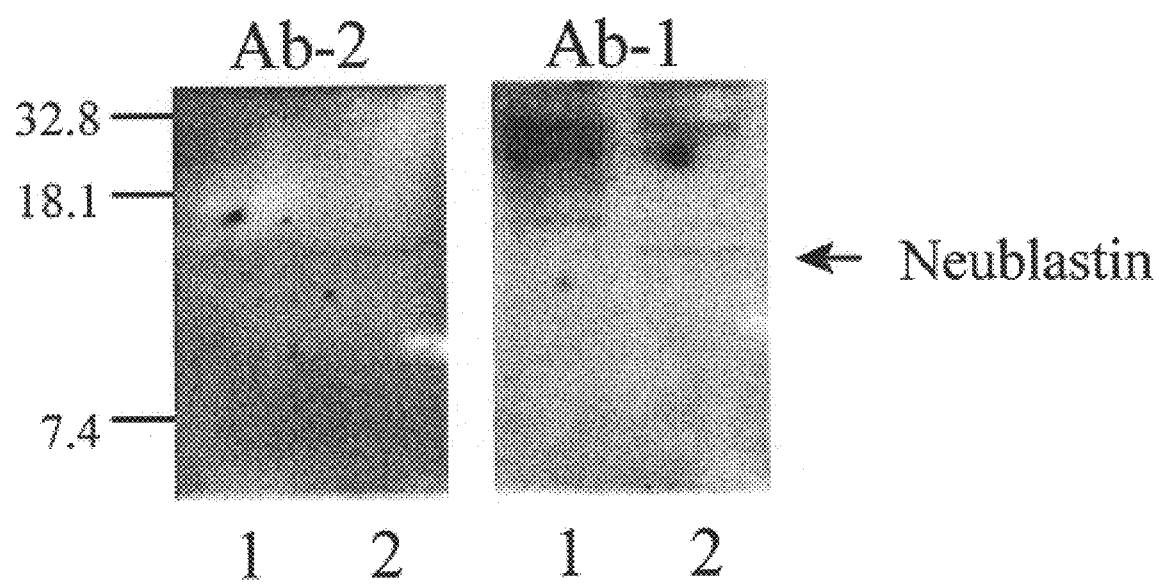
FIG. 3 is a photographic image of two western blots which compare the degrees to which neublastin protein is expressed in non-transfected HiB5 cells (lane 1) relative to an HiB5 cell-line stably-transfected with neublastin cDNA (lane 2) was probed with either the neublastin-specific antibody Ab-2 (left blot; Panel A) or the neublastin-specific antibody Ab-1 (right blot; Panel B).

FIG. 2 shows the expression of neublastin cDNA in the HiB5pUbi1zNBN22 clone (i.e., Northern blot probed with As shown in FIG. 3, antibodies raised against neublastin-derived polypeptides also recognised a protein of approximately 13 kilodaltons ("kD") in conditioned medium from the HiB5pUbi1zNBN22 clone but not from non-transfected HiB5 cells (cf. Example 6).

The predicted molecular weights of the non-modified (i.e. lacking post-translational modifications) neublastin polypeptides NBN140 (SEQ ID NO:10), NBN116 (SEQ ID NO:11) and NBN113 (SEQ ID NO:12) were determined to be 14.7 kilodaltons ("kD"), 12.4 kD, and 12.1 kD, respectively.

Methods: A Northern blot with total RNA (10 μg) from untransfected HiB5 cells and the HiB5pUbi1zNBN22 clone was prepared by electrophoresis on a 0.8% formaldehyde agarose gel and blotted onto a nylon membrane (Duralone, Stratagene). The blot was hybridized and washed as described in Example 3 with a 1.3 kb $^{32}$P-labelled probe prepared by random labelling covering SEQ ID. NO:8 and additional nucleotides from the 5'UTR and 3'UTR of the neublastin cDNA. The blot was exposed to a Hyperfilm MP (Amersham) at −80° C. using intensifying screens.

Conditioned medium from Hib5pUbi1zNBN22, or untransfected Hib5 cells incubated overnight in serum-free medium supplemented with N2 supplement (Life Technologies; Cat. No. 17502–048) was concentrated and separated on 15% polyacrylamide gels (Amersham Pharmacia Biotech; Cat. No. 80-1262-01). Proteins were transferred to PVDF-membranes (Amersham Pharmacia Biotech; Cat. No. RPN-303F) and non-specific protein-binding sites were blocked with 5% non-fat dry milk in PBS with 0.1% Tween-20. Membranes were incubated overnight with a polyclonal neublastin antibody (1:1000), followed by incubation with a secondary anti-rabbit IgG antibody (Amersham Pharmacia Biotech; Cat. No. NA 934) conjugated to horseradish peroxidase (1:2000). Immunostaining was visualised using enhanced chemoluminiscence (ECL) (Amersham Pharmacia Biotech; Cat. No. RPN2109) or ECL+ (Amersham Pharmacia Biotech; Cat. No. RPN2132) according to the manufacturer's instructions (Amersham).

The results of these experiments are shown in FIG. 3. FIGS. 3A and 3B are illustrations of the expression of neublastin protein in transfected HiB5 cells. Overnight medium from non-transfected HiB5 cells [Lane 1], or from an HiB5 clone stable transfected with neublastin cDNA [Lane 2], were concentrated as described infra. The medium was then analyzed by Western blotting using two different polyclonal antibodies, Ab-1 and Ab-2 described in Example 10, specific for neublastin. In the medium derived from transfected cells, both of the antibodies were found to recognize a protein with a molecular weight of approximately 15 kDa. This protein was not seen in non-transfected HiB5 cells.

The cloned cDNA encoding neublastin can also be inserted into other eukaryotic expression vector, e.g., the eukaryotic expression vector TEJ-8 (Johansen et al., FEBS Lett.,1990, 267:289–294) or pcDNA-3 (Invitrogen), and the resulting expression plasmid transfected into an alternative mammalian cell line, e.g., Chinese Hamster Ovary ("CHO") cells, the HEK293, the COS, the PC12, or the RN33b cell lines, or a human neural stem cell. Stable cell lines expressing neublastin are used, e.g., to produce the neublastin protein.

Expression in CHO Cells

Construction of plasmid pJC070.14 In order to express the Neublastin cDNA in Chinese hamster ovary cells, a cDNA fragment encoding the prepro form of human Neublastin was inserted into the mammalian expression vector pEAG347 to generate plasmid pJC070.14. pEAG347 contains tandem SV40 early and adenovirus major late promoters (derived from plasmid pAD2beta; Norton and Coffin, Mol. Cell. Biol. 5: 281 (1985)), a unique NotI cloning site, followed by SV40 late transcription termination and polyA signals (derived from plasmid pCMVbeta; MacGregor and Caskey, Nucl. Acids. Res. 17: 2365 (1989)). In addition, pEAG347 contains a pUC19-derived plasmid backbone and a pSV2dhfr-derived dhfr for MTX selection and amplification in transfected CHO cells.

Plasmid pJC070.14 was generated in two steps. First, a fragment encoding the prepro form of human Neublastin was isolated from plasmid pUbi1Z-NBN using the polymerase chain reaction with oligonucleotides KD2–824 5'AAGGAAAAAA GCGGCCGCCA TGGAACTTGG ACTTGGAGG3' (SEQ. ID. NO. 31), KD2-825 5'TTTTTTCCTT GGCGGCCGCT CAGCCCAGGC AGCCGCAGG3' (SEQ. ID. NO. 32) and PFU polymerase. The fragment was cloned into the Srf-1 site of pPCR-Script Amp SK(+) to generate the plasmid pJC069. In the second step, a partial Not-1 digest was performed on plasmid pJC069 to generate a 685bp fragment (containing the neublastin gene) which was cloned into the Not-1 site of plasmid pEAG347 to generate plasmid pJC070.14. Transcription of the neublastin gene in plasmid pJC070.14 is controlled by the adenovirus major late promoter.

Figure 10:
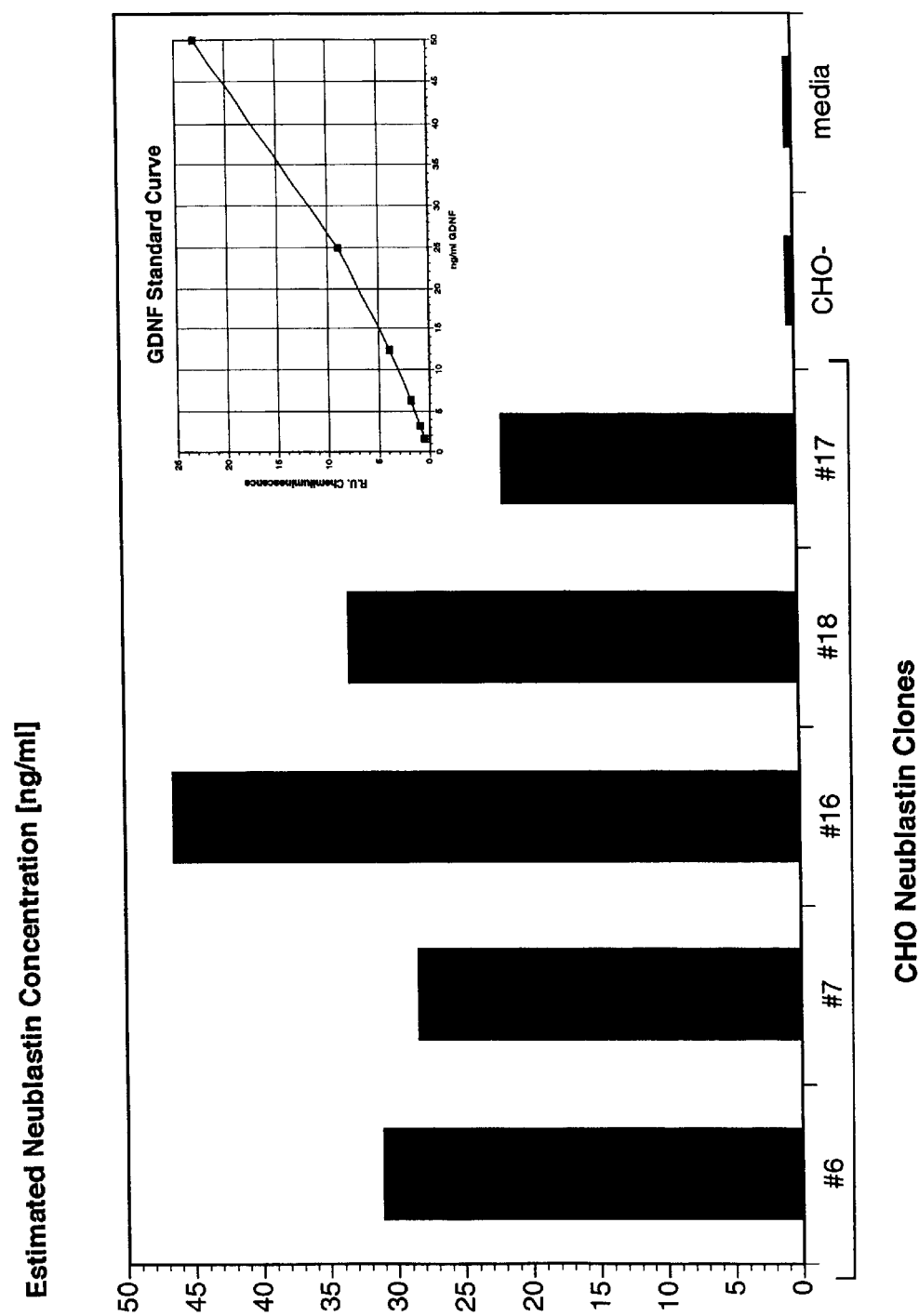
FIG. 10 illustrates neublastin production from CHO cell lines.

Generation of CHO cell lines expressing Neublastin. 200 μg of pJC070.14 was linearized by digestion with the restriction endonuclease Mlu-1. The DNA was extracted with phenol: chloroform:isoamyl alchohol (25:24:1) and ethanol precipitated. The linearized DNA was resuspended in 20 mM Hepes pH7.05, 137mM NaCl, 5mM KCl, 0.7mM $Na_2HPO_4$, 6 mM dextrose (HEBS) and introduced into ~4E7 CHO dukx B1(dhfr−) cells (p23) by electroporation (280V and 960 μF). Following electroporation, the cells were returned to culture in α+ Modified Eagle's Medium (MEM) supplemented with 10% fetal bovine serum (FBS) for two days. The cells were then trypsinized and replated in 100 mm dishes (100,000 cells/plate) in α-MEM (lacking ribo- and deoxyribonucleosides), supplemented with 10% dialyzed FBS, for five days. The cells were subsequently split at a density of 100,000 cells/100 mm plate, and selected in 200 nM methotrexate. Resistant colonies were picked and scaled up to 6 well plates; conditioned media from each clone was screened using a specific assay for neublastin described below. The twelve clones expressing the highest level of neublastin were scaled up to T162 flasks and subsequently reassayed. As shown in FIG. 10, the CHO cell lines produced neublastin in the range of 25 to 50 ng/ml.

Ternary complex assay for neublastin. We assayed for the presence of neublastin in the media of CHO cell line supernatants using a modified form of a ternary complex assay described by Sanicola et al. (Proc Natl Acad Sci USA 94: 6238 (1997).

In this assay, the ability of GDNF-like molecules can be evaluated for their ability to mediate binding between the extracellular domain of RET and the various co-receptors, GFRα1, GFRα2, and GFRα3. Soluble forms of RET and the co-receptors were generated as fusion proteins. A fusion protein between the extracellular domain of rat RET and placental alkaline phosphatase (RET-AP) and a fusion protein between the extracellular domain of rat GFRα1 (disclosed in published application WO9744356; Nov. 27, 1997, herein incorporated by reference) and the Fc domain of human IgG1 (rGFRα1-Ig) have been described (Sanicola et al. Proc Natl Acad Sci USA 94: 6238 (1997)).

To generate a fusion protein between the extracellular domain of murine GFRα3 and the Fc domain of human IgG1 (mGFRα3-Ig), a DNA fragment encoding amino acids 1-359 of murine RETL3 was ligated to a fragment containing the Fc domain of human IgG1 and cloned into the expression vector pEAG347 to generate plasmid pGJ144. Plasmid pGJ144 was transfected into Chinese hamster ovary cells (CHO) to generate a stable cell line producing the fusion protein, which was purified on a Protein A Sepharose immunoaffinity column using standard methods. In summary, if the GDNF-like molecule can mediate binding of the co-receptor to RET in this assay, then the RET-AP fusion protein will be retained on the plate and the amount that is retained can be measured using a chemiluminescent substrate for alkaline phosphatase.

Dynex Microlite-1 ELISA plates (Dynex Technologies) were coated with 1 μg/ml goat antibody specific for human Fc in 50 mM bicarbonate/carbonate, pH 9.6 for 16 hr. The plates were emptied and filled with 300 μl of 1% I-block (Tropix) in TBS/0.5% Tween-20 (TBST), for 1 hr. After washing three times with TBST the wells were filled with 100 μl of I pg/ml rGFRα1-Ig or mGFRα3-Ig diluted in conditioned media from 293 EBNA cells expressing the RET-AP fusion gene. 100 μl of conditioned media from the CHO neublastin clones was then added to the top well of a column of wells, and 2 fold serial dilutions were performed down each row of wells, and incubated for 1.5 hr at room temperature. The plates were then washed three times with TBST, and twice with 200 mM Tris pH9.8, 10 mM$MgCl_2$ (CSPD buffer). The wash solution was then replaced with 425 μM CSPD (Tropix) in CSPD buffer containing 1 mg/ml Sapphire chemiluminescence enhancer (Tropix), and incubated for 30' at room temperature. The chemiluminescent output was measured using a Dynatech luminometer.

Figure 11:
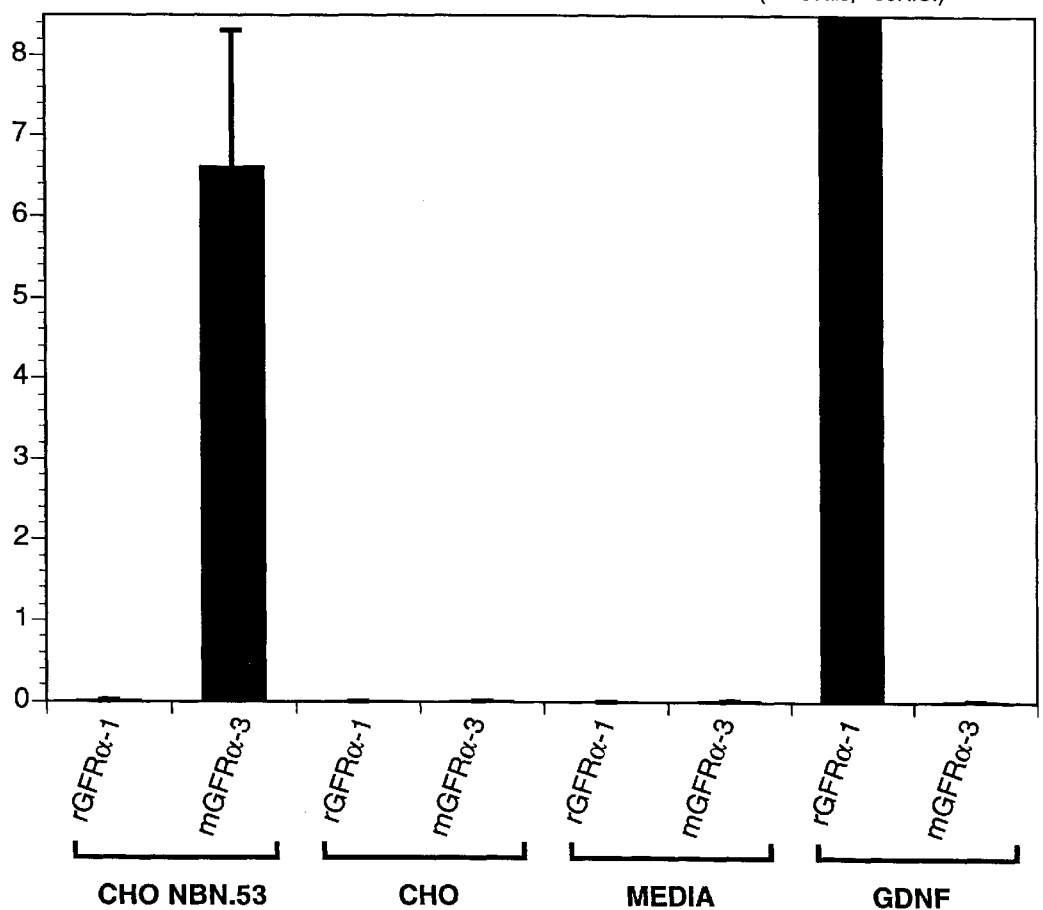
FIG. 11 illustrates a comparison of neublastin and GDNF binding to GFRβ-1 and GFRβ-3 receptors.

In the initial experiments, we investigated whether neublastin produced by the CHO cell lines could mediate the binding of GFRα1 or GFRα3 to the extracellular domain of RET. As shown in FIG. 11, conditioned medium from CHO cell clone #53 produced a robust signal in the ternary complex assay when the mGFRα3-Ig fusion protein was included, but no signal when the rGFRα1 -Ig fusion protein was included, indicating that neublastin binds to GFRα3 but not to GFRα1. This behavior clearly distinguishes neublastin from GDNF; as shown in FIG. 11, GDNF binds to GFRα1 but not to GFRα3. No signal was observed with either co-receptor fusion protein, when conditioned medium from the parental CHO cell line or straight medium was assayed.

In order to quantitate the expression levels of neublastin in the CHO cell lines, a standard curve was prepared using rGFRα1-Ig and GDNF starting at a concentration of 1 ng/ml. Neublastin concentrations for the different CHO cell lines were then calculated using this standard curve; the levels produced by five CHO cell lines are shown in FIG. 10. Because this estimation depends on the untested assumption that the binding affinity between GDNF and GFRα1 is similar to the binding affinity between neublastin and GFRα3, these levels are only approximate.

Analysis of neublastin from CHO cell line supernatants. In order to further analyze the neublastin produced by the CHO cell lines, the protein was extracted from the medium using the GFRα3-Ig fusion protein and analyzed by western blots with polyclonal antibodies raised against neublastin peptides.

In the first experiment, the neublastin was extracted with mGFRα3-Ig attached to Sepharose beads. mGFRα3-Ig was attached to Sepharose beads using the conditions suggested by the manufacturer, Pharmacia Inc. 100 μL of mGFRα3-Ig-Sepharose was added to 1.0 mL samples of conditioned medium from a negative control CHO cell line or from the neublastin producing CHO cell line #16. The suspensions were incubated for two hours on a rocking platform. Each suspension was centrifuged and the supernatant removed followed with three 1.0 mL washes with 10 mM HEPES, 100 mM NaCl, pH 7.5. Each resin was resuspended in 100 μL of 2×reducing sample buffer and heated to 100° C. for 5 minutes. 20 μL of the sample buffer supernatant and 10 μL of a molecular weight standard (FMC) were applied to each well of a 10–20% precast SDS-PAGE gel (Owl Scientific). The gel was electrophoresed at 40 mA constant current for 72 minutes.

Figure 12:
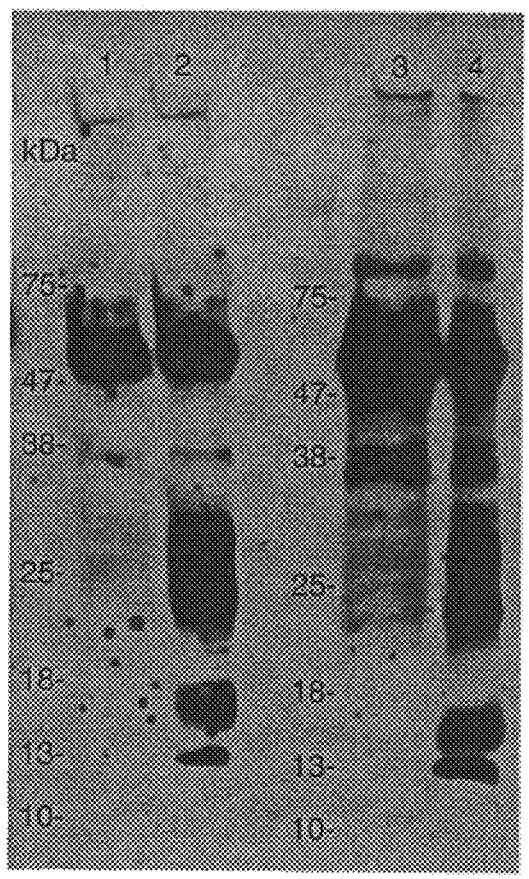
FIG. 12 is a photographic image of a western blot which illustrates R30 anti-peptide antibody and R31 anti-peptide antibody binding to neublastin.

For western blot analysis, the protein was electroblotted to nitrocellulose (Schleicher and Schuell) in a Hofer Scientific apparatus in 10 mM CAPS, 10% methanol, 0.05% SDS, pH 11.2 buffer system (45 minutes at 400 mA constant current). After the transfer, the nitrocellulose filter was removed from the cassette and the molecular weight markers were visualized by staining with a solution of 0. 1% Ponceau S in 1% acetic acid for 60 seconds. The membrane was cut into two sections and the excess stain was removed by gentle agitation in distilled water. The membranes were blocked in 2% nonfat dry milk in TBS overnight at 4° C. The membranes were incubated individually with two of the affinity-purified anti-neublastin peptide antibodies (R30 and R31) at a concentration of 1.0 μg/mL in 2% nonfat dry milk in TBS). The membranes were washed with three 10 minute washes in TBS-Tween and incubated in a 1:5000 dilution of goat anti-rabbit IgG-HRP conjugate (Biorad) for 30 minutes. The membranes were washed with three 10 minute washes of TBS-Tween and developed with ECL substrate (Amersham). As shown in FIG. 12, specific bands were detected in the proteins extracted from the neublastin producing CHO cell line with both antibodies (lanes 2 and 4), when compared to the bands observed in the extracted proteins from the negative control cell line (lanes 1 and 3).

The molecular weight of the lower species is about 13 kD and probably represents the mature domain of neublastin, generated after cleavage of the pro- domain. This cleavage could occur after any one of the three Arg-_(e.g., -RXXR↓-) residues of the prepro neublastin protein to generate either the 140 AA, 116 AA or 113 AA forms, as set forth in SEQ.ID.NOS. 10, 11, or 12, respectively. The predicted molecular weights of the non-modified (i.e., lacking post-translational modifications) neublastin polypeptides NBN140 (SEQ. ID. NO. 10), NBN116 (SEQ. ID. NO. 11), and NBN113 (SEQ. ID. NO. 12) were determined to be 14.7 kD, 12.4 kD, and 12.1 kD, respectively. Further analysis will be needed to confirm the structure of this species as well as the other neublastin specific bands.

In the second experiment, the neublastin was extracted with hGFRα3-Ig captured on an ELISA plate. To generate a fusion protein between the extracellular domain of human GFRα3 (disclosed in published application WO97/44356; Nov. 27, 1997, herein incorporated by reference) and the Fc domain of human IgG1 (hGFRα3-Ig), a DNA fragment encoding amino acids 1–364 of human GFRα3 was ligated to a fragment containing the Fc domain of human IgG1 and cloned into the expression vector CH269 described by Sanicola et al. (Proc Natl Acad Sci USA 94: 6238 (1997)). The fusion protein encoded by this plasmid was transiently expressed in 293-Epstein-Barr virus-encoded nuclear antigen (EBNA) cells and purified on a Protein A Sepharose immunoaffinity column using standard methods.

Six wells of a 96-well plate were coated overnight at 4° C. with goat anti-human IgG (Fcδ fragment specific; Jackson Immunulogics) at a concentration of 25 μg/ml in PBS (300 μl/well). The wells were blocked for 1 h at room temperature with 400 μl of 1% BSA in PBS. After 3 washes with PBST (PBS+0.05% Tween 20), 300 μl hGFRα3-Ig (10 μg/ml in PBS containing 0.1% BSA) was added to each well. The plate was incubated for 1 h at room temperature and shaken gently (200 strokes/min) to maximize the binding. The wells were then emptied and washed again 3 times with PBST. 250 μl of conditioned media from a negative control CHO cell line or from the neublastin producing CHO cell line #25 was added to each of 3 wells. The plate was incubated for 3 h at room temperature and shaken gently (300 strokes/min). The wells were then washed twice with PBST. 25 μl of non-reducing Laemli loading buffer was added to the first well and the plate was shaken rapidly for 5 min to elute the bound proteins (1300 strokes/min). The content was transferred to the next well and the procedure was repeated to elute the proteins bound in the second and third wells. After adding β-mercaptoethanol (5% final), the samples were boiled for 5 minutes and analyzed by SDS-PAGE on a 10–20% polyacrylamide gel.

Figure 13:
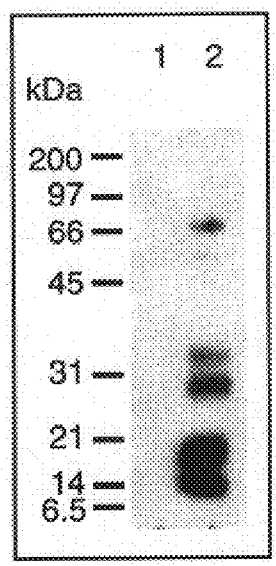
FIG. 13 is a picture of a gel showing extraction of neublastin by affinity binding on RETL3-Ig.

For western blot analysis, the proteins were transferred to nitrocellulose. The membrane was blocked and probed in 5% non fat dry milk, PBST and washed in PBST. Neublastin was detected by electrochemoluminescence after reaction with polyclonal antibodies (R30 and R3 1) raised against two neublastin peptides (at 1 ug/ml) followed by reaction with HRP-conjugated goat anti-rabbit antibodies (BioRad). As shown in FIG. 13, five neublastin specific bands were detected in the extracted proteins from the neublastin producing CHO cell line (lane 2). The lower two bands are very similar to the bands observed in FIG. 12; again, the lower band probably represents the mature domain of neublastin generated after cleavage of the pro-domain.

Subsequent analysis (data not shown) of the bands in FIG. 13 shows that deglycosylation with PGNase F of the approximately 18 kD band reduces that band to a size equivalent to the lower-most band in the gel of FIG. 13. This suggests that neublastin may be produced as a glycosylated protein in mammalian cells.

Expression of Neublastin in E. coli

In order to express the neublastin gene in *E. coli*, syngenes were constructed with lower GC content and preferred *E. coli* codons. The syngene is being cloned into two vectors, pET19b and pMJB164, a derivative of pET19b. The construction with pET19b is shown in FIG. 14. In this construct, the sequence encoding the mature domain of neublastin (NBN113) is directly fused to an initiating methionine. The construction with pMJB164 is shown in FIG. 15. In this construct, the mature domain of neublastin is fused to a histidine tag (i.e. 10 histidines) separated by an enterokinase cleavage site. The initiating methionine precedes the histidine tag.

Nucleotide Sequence Encoding Neublastin in FIG. 14
ATGGCTGGAGGACCGGGATCTCGT-
GCTCGTGCAGCAGGAGCACGTGGCTGTCGTCT
GCGTTCTCAACTAGTGCCGGTGCGTG-
CACTCGGACTGGGACACCGTTCCGACGAACT
AGTACGTTTTCGTTTTTGTTCAGGATCT-
TGTCGTCGTGCACGTTCTCCGCATGATCTA
TCTCTAGCATCTCTACTAGGAGCCGGAG-
CACTAAGACCGCCGCCGGGATCTAGACCT
GTATCTCAACCTTGTTGTAGACCTACTA-
GATACGAAGCAGTATCTTTCATGGACGTA
AACTCTACATGGAGAACCGTAGATAGAC-
TATCTGCAACCGCATGTGGCTGTCTAGGA
TGATAATAG SEQ. ID. NO. 29

Nucleotide Sequence Encoding His-tagged Neublastin in FIG. 15
ATGGGCCATCATCATCATCATCATCAT-
CATCATCACTCGAGCGGCCATATCGACGAC GAC-
GACAAGGCTGGAGGACCGGGATCTCGT-
GCTCGTGCAGCAGGAGCACGTGGCTG
TCGTCTGCGTTCTCAACTAGTGCCGGT-
GCGTGCACTCGGACTGGGACACCGTTCCGA
CGAACTAGTACGTTTTCGTTTTTGT-
TCAGGATCTTGTCGTCGTGCACGTTCTCCGCAT
GATCTATCTCTAGCATCTCTACTAG-
GAGCCGGAGCACTAAGACCGCCGCCGGGATCT
AGACCTGTATCTCAACCTTGTTGTAGAC-
TACTAGATACGAAGCAGTATCTTTCATG GACG-
TAAACTCTACATGGAGAACCGTAGATA-
GACTATCTGCAACCGCATGTGGCTGT
CTAGGATGATAATAG SEQ. ID. NO. 30.

Example 6

Effect of Neublastin on the Survival of Rat Embryonic Dopaminergic Neurons and ChAT Activity In this series of experiments the effect of conditioned medium from neublastin-producing HiB5pUbi1zNBN22 cells described above was assessed.

Preparation of Cultures: The ventral mesencephalon or spinal chord was dissected out from rat E14 embryos in cold Hanks Buffered Salt Solution (HBSS). Tissue pieces were incubate in sterile filtered 0.1% trypsin (Worthington) and 0.05% DNase (Sigma) in HBSS at 37° C. for 20 min. Tissue pieces was then rinsed four times in HBSS +0.05% DNase and dissociated using a 1 ml automatic pipette. The suspension was then centrifuged at 600 rpm for 5 min and the pellet was re-suspended in serum conditioned medium (SCM; DMEM with 10% foetal calf serum). The total number of cells was assessed by tryphan blue dye exclusion method and plated at a density of 100.000 cells/cm$^2$ in poly-L-lysine coated eight-well chamber slides (Nunc) for assessment of dopaminergic neuron survival or at 200 000 cells/cm$^2$ in 48 well plates (Nunc) for ChAT activity measurements. Cells were incubated in SCM at 5% $CO_2$/95% $O_2$ and 95% humidity in 37° C. for 24–48 h before changing to serum free medium (SFM) with addition of neurotrophic factors.

Cells for assessing dopaminergic neuron survival was left for 5 days in SFM+trophic factor additions and then fixed for 5 min in 4% PFA and stained for tyrosine hydroxylase by immunohistochemistry.

Cells for ChAT activity were left for 3 days with SFM and then lysed in HBSS +0.1% Triton X-100 and immediately frozen down on dry ice until Chat activity measurement.

Trophic Factor Addition: Conditioned medium was collected from non-transfected HiB5 control or HiB5 producing neublastin (HiB5pUbi1zNBN22) or GDNF (HiB5pUbi1zGDNF-L17). HiB5pUbi1zNBN22 produces approximately 20 ng GDNF/24 hours/10$^5$ cells as determined by GDNF-ELISA on conditioned medium, collected from the cells. The respective cell lines were incubated overnight with DMEM+1% FCS and the supernatant was taken off and stored at –20° C. until use. The supernatants were diluted in 1:50 in SFM when added to the cells. Separate wells were treated with HiB5 control supernatant (1:50)+purified recombinant rat GDNF (from 0.03–10 ng/ml).

The results of these experiments are shown in FIG. 4. FIGS. 4A–4C are illustrations of the effect of neublastin, secreted from HiB5pUbi1zNBN22 cells, on the survival of cultured rat embryonic, dopaminergic, ventral mesencephalic neurons and ChAT activity in cholinergic cranial nerve motor neurons in serum-free medium as described infra in Example 5.1.

FIG. 4A is an illustration of the dose-response curve for recombinant GDNF on ChAT activity (dpm/hour) measured at DIV5 in serum-free cultures which were initially established from E14 ventral mesencephali [i.e., HiB5; GDNF 0.03 ng/ml; GDNF 0.1 ng/ml; GDNF 0.3 ng/ml; GDNF 1 ng/ml; GDNF 10 ng/ml; GDNF 100 ng/ml].

FIG. 4B is an illustration of ChAT activity (dpm/hour) measured at DIV5 in serum-free cultures which were initially established from E14 ventral mesencephali. Diluted conditioned medium from either neublastin producing HiB5pUbi1zNBN22 cells (neublastin) or GDNF-producing HiB5GDNFL-17 (GDNFL-17) cells were added as indicated in the figure [i.e., neublastin 1:10; neublastin 1:50; GDNF L-17 1:50].

FIG. 4C is an illustration of the number of tyrosine hydroxylase immunoreactive cells per well [No. TH+ cells/well] at DIV7 in serum-free cultures which were initially established from E14 rat ventral mesencephali. Diluted conditioned medium from either non-transfected HiB5 cells (HiB5) or neublastin-producing HiB5pUbi1zNBN22 cells (neublastin) or recombinant GDNF, in various concentrations, were added as indicated in the figure [i.e., HiB5 1:10; HiB5 1:40; GDNF 0.1 ng/ml; GDNF 10 ng/ml; GDNF 100 ng/ml; and neublastin 1:40].

Conditioned medium from neublastin transfected HiB5 cells diluted 1:40 significantly increases the number of TH immunoreactive cells pr. well compared to control (untransfected) HiB5 cells at an equivalent and a lower dilution (1:10 and 1:40) (see, e.g., FIG. 4B). The increase in TH-immunoreactive cells are comparable to the increase seen at a maximal GDNF concentration (10 ng/ml). This indicates that neublastin secreted to the medium has an effect on survival of the dopaminergic neuron population from rat embryonic ventral mesencephalon. In contrast, unlike GDNF secreted from transfected HiB5 cells, no effect of conditioned medium from neublastin transfected HiB5 cells is seen on another neuronal population in the same culture, the cholinergic neurons (see, e.g., FIG. 4A).

Example 7

Effect of Neublastin on the Survival of Slice Cultures of Pig Embryonic Dopaminergic Ventral Mesencephalic Neurons In this experiment the effect of co-culturing neublastin-producing HiB5pUbi1 zNBN22 cells with slice cultures of ventral mesencephali from porcine embryos.

Preparation of Cultures: Ventral mesencephali (VM) were isolated from porcine embryos (E28; n=12) under sterile conditions, chopped into 400 μm slices and placed in chilled Gey's balanced salt solution (GIBCO) with glucose (6.5 mg/ml). The tissue slices were cultured by the interface culture method, originally developed by Stoppini et al. [L. Stoppini, P. A. Buchs, D. Muller, *J. Neurosci. Methods* 1991 37 173–182].

In brief, slices were placed on semi-porous membranes (Millipore, 0.3 μm; 8 slices/membrane corresponding to one VM) placed as inserts in 6-well plates (Costar) with serum containing medium (Gibco BRL). Each well contained 1 ml medium (50% Optimem, 25% horse serum, 25% Hank's balanced salt solution (all GIBCO)) supplemented with D-glucose to a final concentration of 25 mM. At day 0, 7000 transfected HiB5pUbi1zNBN22 (neublastin) or 7000 non-transfected HiB5 cells (control) were seeded on each tissue slice. The co-cultures were first grown in an incubator at 33° C. for 48 hours allowing the HiB5 cells immortalized with a temperature sensitive oncogene to proliferate, and then placed in an incubator at 37° C., where the HiB5 cells differentiate. The medium was changed twice a week. Antimitotics and antibiotics were not used at any stage.

Determination of Dopamine by HPLC: At day 12 and 21 in vitro, the culture medium was collected and analysed for dopamine using HPLC with electrochemical detection (W. N. Slooth, J. B. P. Gramsbergen, *J. Neurosci. Meth.* 1995 60 141–49).

Tissue Processing and Immunohistochemistry: At day 21, the cultures were fixed in 4% paraformaldehyde in phosphate buffer for 60 min., dehydrated in a 20% sucrose solution for 24 hours, frozen, cryostat sectioned at 20 μm (4 series), and mounted onto gelatine coated microscope slides. One series of sections was immunostained for tyrosine hydroxylase (TH). Briefly, sections were washed in 0.05M tris-buffered saline (TBS, pH 7.4) containing 1% Triton X-100 for 3×15 min. and incubated with 10% fettle bovine serum (FBS, Life Technologies) in TBS for 30 min. The tissue was then incubated for 24 hours at 4° C. with monoclonal mouse anti-TH antibody (Boehringer Mannheim) diluted 1:600 in TBS with 10% FBS. After rinsing in TBS with 1% Triton X-100 for 3×15 min., sections were incubated for 60 min. with bio-tinylated anti-mouse IgG antibody (Amersham) diluted 1:200 in TBS with 10% FBS. The sections were then washed in TBS with 1% Triton X-100 (3×15 min.) and incubated for 60 min. with streptavidin-peroxidase (Dako) diluted 1:200 in TBS with 10% FBS. After washing in TBS (3×15 min.), bound antibody was visualised by treatment with 0.05% 3,3-diaminobenzidine (Sigma) in TBS containing 0.01% $H_2O_2$. Finally, the sections were dehydrated in alcohol, cleared in xylene, and cover-slipped in Eukitt.

Cell counts and morphometric analysis: Quantification of immunoreactive TH-ir neurons was performed using bright field microscopy (Olympus). Only cells displaying an intense staining with a well preserved cellular structure and a distinct nucleus were counted. The estimation was based on cell counts in every fourth culture section using a ×20 objective. Cell numbers were corrected for double counting according to Abercrombie's formula (M. Abercrombie, *Anat. Rec.* 1946 94 239–47), using the average diameter of the nuclei in the TH-ir neurons (6.6±0.2 μm, n=30). The size of the nuclei was estimated using a neuron tracing system (Neurolucida, MicroBrightField, Inc.).

Figures 5A, 5B:
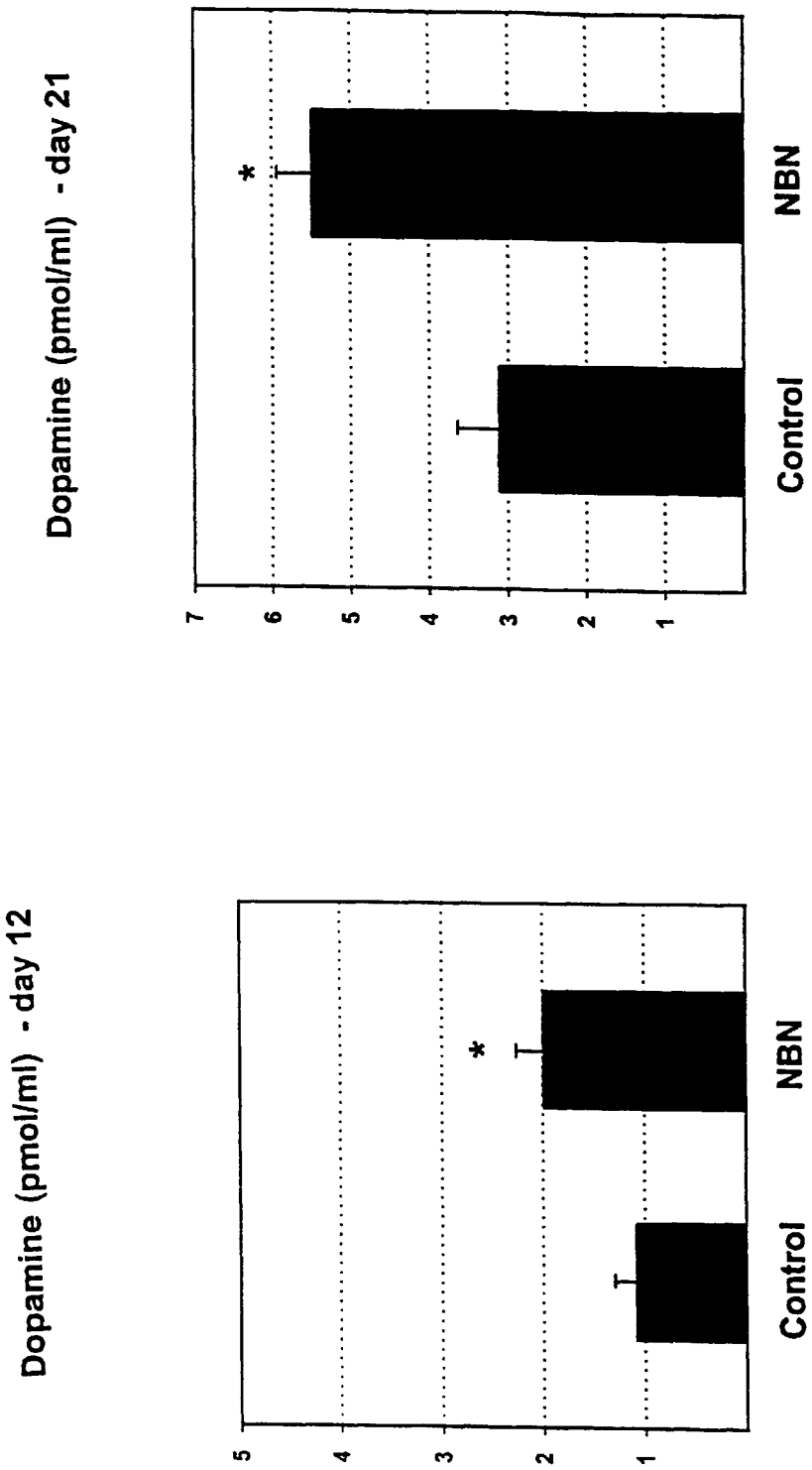
FIG. 5A and FIG. 5B illustrate dopamine released to the medium at DIV12 [Dopamine (pmol/ml)—day 12] and DIV21 [Dopamine (pmol/ml)—day 21], respectively.
Figure 5C:
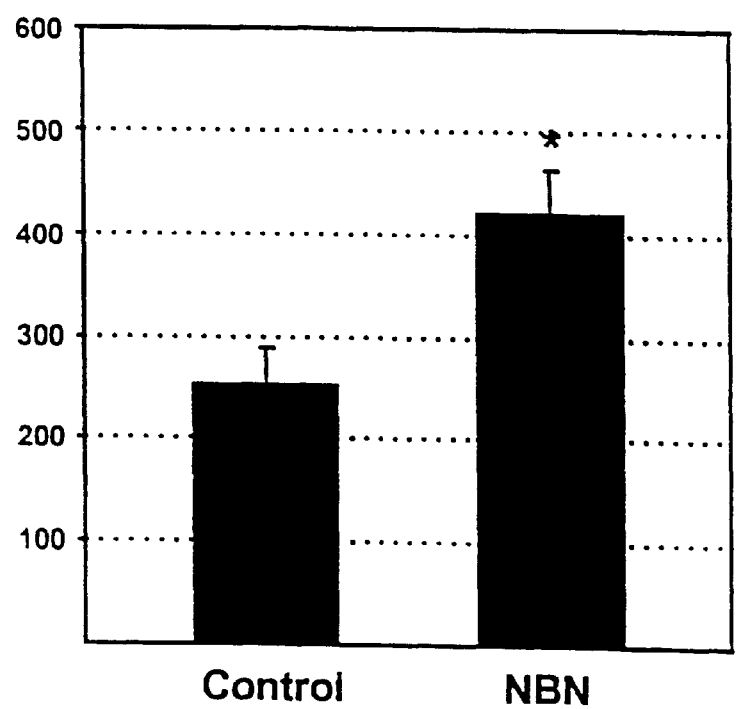
FIG. 5C is an illustration of the number of tyrosine hydroxylase immunoreactive cells per culture [TH-ir cells per culture] at DIV21.

The results of these experiments are shown in FIG. 5. FIGS. 5A–5C are illustrations of the effect of neublastin secreted from HiB5pUbi1zNBN22 cells on the function and survival of slice cultures of pig embryonic dopaminergic ventral mesencephalic neurons co-cultured with either HiB5pUbi1zNBN22 cells (neublastin) or HiB5 cells (control) as described infra. FIG. 5A and FIG. 5B: illustrate dopamine released to the medium at DIV12 [Dopamine (pmol/ml)-day 12] and DIV21 [Dopamine (pmol/ml)-day 21], respectively. FIG. 5C is an illustration of the number of tyrosine hydroxylase immunoreactive cells per culture [TH-ir cells per culture] at DIV21.

At day 12 HPLC analysis revealed that medium from HiB5-neublastin co-cultures contained 84% more dopamine than medium from HiB5-C co-cultures (FIG. 5A). At day 21 the difference was 78% (FIG. 5B), and cell counts showed that HiB5-neublastin co-cultures contained 66% more tyrosine hydroxylase immunoreactive neurons than HiB5-C co-cultures (P<0.05) (FIG. 5C). This indicates, that neublastin secreted from the HiB5pUbi1zNBN22 clone has a potent survival effect on embryonic porcine dopaminergic neurons.

Example 8

Survival of Dorsal Root Ganglion Cells in Serum-free Medium

This example shows the neurotrophic activity of a neublastin polypeptide in comparison with known neurotrophic factors.

Pregnant female mice were killed by cervical dislocation. The embryos were processed for culture as follows.

Electrolytically sharpened tungsten needles were used to dissect dorsal root ganglia from indicated stages of C57/B16 mice (Mollegaard Breeding, Denmark). Embryonic ganglia were incubated for 5 minutes at 37° C. with 0.05% trypsin (Gibco/BRL) in calcium and magnesium-free Hanks balanced salt solution. Postnatal ganglia were treated with collagenase/dispase 1 mg/ml for 30 to 45 minutes and then trypsin/DNAse 0,25% for 15 minutes. After removal of the trypsin solution, the ganglia were washed once with 10 ml of DMEM containing 10% heat inactivated horse serum, and were gently triturated with a fire-polished Pasteur pipette to give a single cell suspension.

The cells were plated on 24 well plates (Nunc), that were precoated with polyornithine (0.5 mg/ml, overnight) and laminin (20 mg/ml for 4 h; Gibco/BRL). The neurons were incubated at 37° C. in a humidified 5% $CO_2$ incubator in a defined medium consisting of Hams F14 supplemented with 2 mM glutamine, 0.35% bovine serum albumin, 60 ng/ml progesterone, 16 mg/ml putrescine, 400 ng/ml L-thyroxine, 38 ng/ml sodium selenite, 340 ng/ml triiodo-thyronine, 60 mg/ml penicillin and 100 mg/ml streptomycin.

After 48 hours of incubation, neurons were clearly recognised by their bipolar morphology under phase-contrast optics. The percentage neuronal survival in the absence or presence of trophic factors (added to the culture medium prior to plating the neurons at 10 ng/ml), or of conditioned medium from the neublastin producing HiB5pUbi1zNBN22 cells, was assessed by counting the neurons in the wells at 48 hours.

Figure 9:
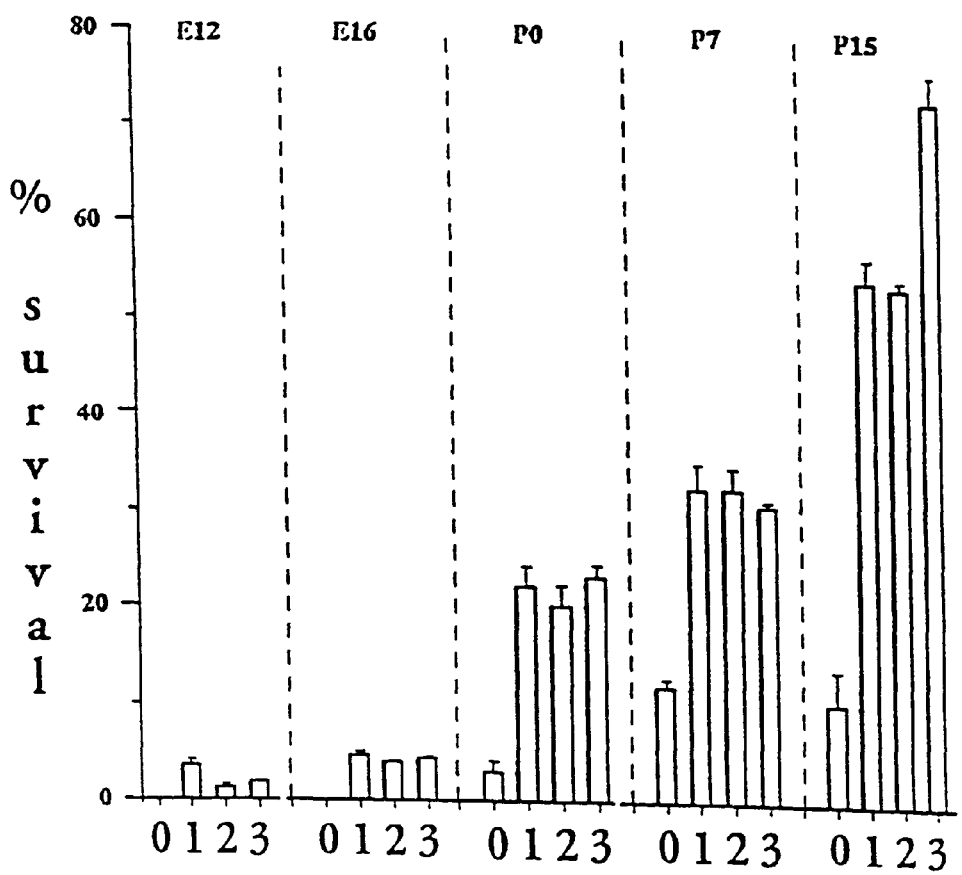
FIG. 9 illustrates the neurotrophic activity on cultures of dissociated rat dorsal root ganglion cells from different development stages of a polypeptide disclosed in the present invention in comparison to those obtained with known neurotrophic factors [0 control experiment (in absence of factors); 1 in the presence of GDNF; 2 in the presence of Neurturin; 3 in the presence of Neublastin of the invention; E12 embryonic day 12; E16 embryonic day 16; P0 the day of birth; P7 day 7 after birth; and P15 day 15 after birth].

The results of these experiments are presented in FIG. 9, in which figure:

0 represents the control experiment (in absence of factors);

1 represents experiments in the presence of GDNF;

2 represents experiments in the presence of Neuturin;

3 represents experiments in the presence of Neublastin of the invention;

E12 represents data from experiments carried out on DRG cells isolated from embryonic day 12;

E16 represents data from experiments carried out on DRG cells isolated from embryonic day 16;

P0 represents data from experiments carried out on DRG cells isolated from the day of birth;

P7 represents data from experiments carried out on DRG cells isolated from day 7 after birth; and P15 represents data from experiments carried out on DRG cells isolated from day 15 after birth.

These results clearly show that the neurotrophic factor of the invention show activities comparable to, or even better than those of the well established neurotrophic factors.

Example 9

In vivo Effects of Neublastin on Nigral Dopamine Neurons

In order to test the ability of neublastin (neublastin) to protect adult nigral dopamine (DA) neurons from 6-hydroxydopamine induced degeneration, we employed a rat model of Parkinson's disease ([Sauer and Oertel, *Neuroscience* 1994 59, 401–415) and lentiviral gene transfer of neublastin.

Lentivirus production: To generate a lentiviral transfer vector encoding neublastin, pHR'-neublastin, a 1331 bp BamH1 fragment from neublastin cDNA was subcloned in the BamH1/Bgl II site of pSL301 (Invitrogen). From this construct a 1519 bp BamH1/Xho1 fragment was cut out and ligated in the BamH1/Xho1 site of pHR'carrying a woodchuck hepatitis virus post-translational fragment [Zufferey R, Donello J E, Trono D, Hope T J: Woodchuck hepatitis virus posttranscriptional regulatory element enhances expression of transgenes delivered by retroviral vectors"; *J. Virol.* 1999 73 (4) 2886–2892]. To generate pHR-GDNF a 701 bp BamH1/Xho1 fragment from pUbi1z-GDNF was ligated in the BamH1Xho1 site of pHR'.

Production of the lentiviral vector have been described by e.g. Zufferey et al. [Zufferey R, Nagy D, Mandel R J, Naldini L, Trono D: "Multiply attenuated lentiviral vector achieves efficient gene delivery in vivo; *Nat. Biotechnol.* 1997 15 (9) 871–875]. Briefly, the transfer constructs and the helper plasmids pR8.91 and pMDG were co-transfected into 293T cells. Virions released into the media were collected at 48 and 72 hrs post-transfection. To concentrate the virus, the media was centrifuged 1.5 hrs at 141 000 g, and the pellet dissolved in DMEM. The titer of a control carrying the gene for Green Fluorescent Protein ("GFP") was determined to be $10^8$ transforming units (TU)/ml by GFP fluorescence in 293T cells. A RNA slot blot technique [von Schwedler U, >7/ Song J, Aiken C, Trono D: "Vif is crucial for human immunodeficiency virus type I proviral DNA synthesis in infected cells"; *J. Virol.* 1993 67 (8) 4945–4955] was used to determine viral particle titer. In the GDNF supernatant and neublastin supernatant there was 10 times less particles as compared to the GFP supernatant.

Surgical Procedures: All work involving animals was conducted according to the rules set by the Ethical Committee for Use of Laboratory Animals at Lund University.

A total of 21 young adult female Sprague-Dawley rats (B&K Universal, Stockholm, Sweden) were used and housed under 12 hours light:dark cycle with free access to rat chow and water. Retrograde labelling and 6-OHDA lesions were performed 3 weeks prior to lesion according to Sauer and Oertel [Sauer and Oertel, *Neuroscience* 1994 59:401–415]. Briefly, under Equithesin anaesthesia (0.3 ml/100 g) the rats were injected bilaterally with 0.2 $\mu$l of a 2% solution (dissolved in 0.9% NaCl) of the retrograde tracer Fluoro-Gold (FG; Fluorochrome, Inc., Englewood, Colo.). Injections were made using a 2 $\mu$l Hamilton syringe at co-ordinates: AP=+0.5 mm; ML=±3.4 mm relative to bregma; DV=–5.0 mm relative to the dura and incisor bar set to 0.0 mm. In addition, 0.05 $\mu$/min was injected with another 5 min left before the needle was retracted.

Fourteen days after the FG injections animals received a total of 5 deposits (1 $\mu$l/deposit) of a lentiviral vector carrying the gene for green fluorescent protein (GFP), neublastin or GDNF. Four of the deposits were into the striatum along two needle tracts at the following co-ordinates: AP=+1.0 mm, ML=–2.6 mm, $DV_1$=–5.0 mm $DV_2$=–4.5 mm and AP=0.0 mm, ML=–3.7 mm, $DV_1$=–5.0 mm $DV_2$=–4.5 mm. The supranigral deposit was made at AP=–5.2 mm, ML=–2.0 mm, $DV_1$=–6.3 mm. Tooth bar was set at –2.3 mm.

Twenty-one days after retrograde labelling, and 7 days after lentiviral injections the animals were re-anaesthetised and with a, 10 $\mu$l Hamilton syringe a single deposit of 20 $\mu$g 6-OHDA (Sigma; calculated as free base and dissolved in 3 $\mu$l ice cold saline supplemented with 0.02% ascorbic acid) was injected into the right striatum in the same location as the FG deposits. The injection rate was 1 $\mu$l/min, leaving another 3 min before retracting the needle.

Tissue Processing: At 21 days after the 6-OHDA injection the animals were deeply anaesthetised with chloral hydrate and transcardially perfused with saline (pH 7.4; room temperature) for one min followed by 200 ml ice cold formaldehyde solution (4% paraformaldehyde in 0.1M phosphate buffer, pH 7.4). The brains were dissected and postfixed in the same fixative for 3–4 hours and then transferred into 25% sucrose/0.1M phosphate buffer for 48 hours. Five series of 40 $\mu$m sections through the striatum and substantia nigra (SN) were cut on a freezing microtome.

Quantitative Assessment of Dopaminergic Neurons in the SN: The number of FG-labelled in the SN pars compacta was assessed by a blinded observer as described previously [Sauer and Oertel, *Neuroscience* 1994 59, 401–415]. In brief, three consecutive sections centred around the level of the medial terminal nucleus of the accessory optic tract (MTN; –5.3 in the atlas of Paxinos and Watson (1997)) were used and all labelled/stained neurons laterally to the MTN was counted at 40×magnification (n=6–7/group). FG-labelled neurons were included if they were brightly fluorescent under epi-illumination at 330 nm, displayed a neuronal profile and extend at least one neuritic process.

On the lesion side in animals receiving injections of lentivirus carrying GFP the number of FG-positive nigral neurons were reduced to 18% of that on the intact side. In contrast, animals injected with lenti-neublastin showed a near complete protection of the number of FG-positive nigral neurons (89%). This was as efficient as lenti-GDNF treated animals where 87% of the retrogradely labelled neurons remained on the lesioned side. This shows that neublastin is a potent survival factor for lesioned adult nigral dopamine neurons and that it is as potent as GDNF.

Figure 6:
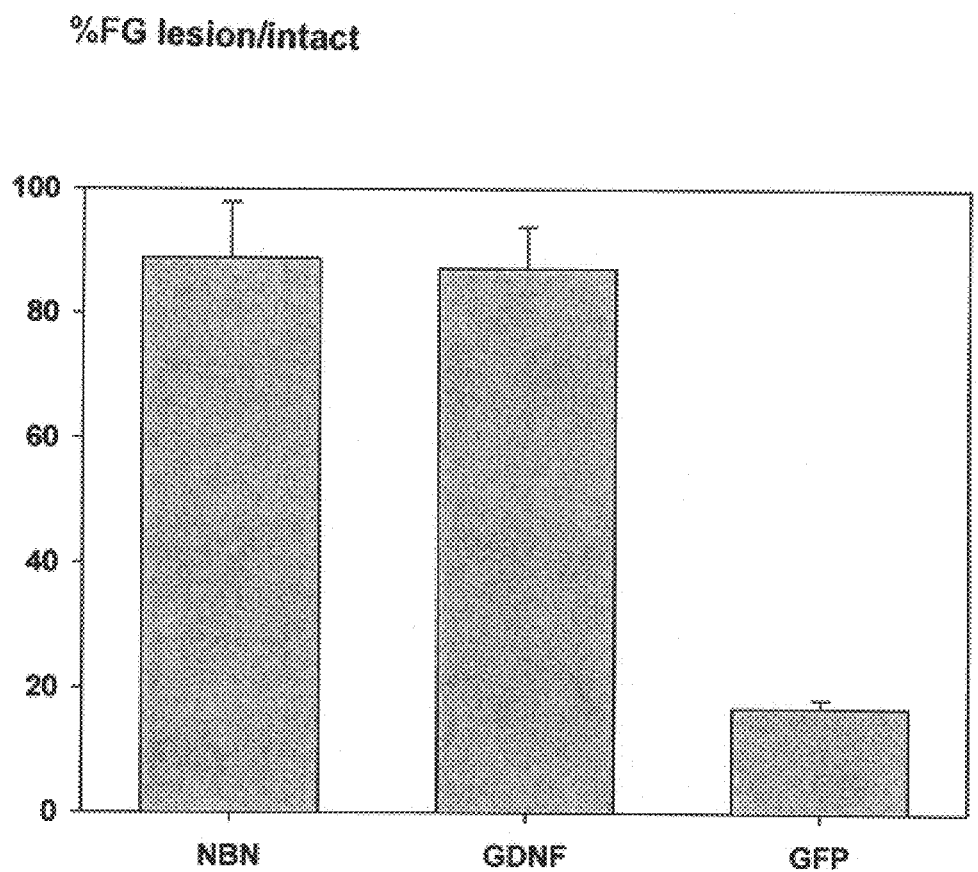
FIG. 6 is an illustration of the in vivo effect of lentiviral-produced neublastin on nigral dopamine neurons.

FIG. 6 is an illustration of the in vivo effect of lentiviral-produced neublastin on nigral dopamine neurons. Neurons of the SN pars compacta, in female Sprague Dawley rats, were retrogradely-labelled with Fluorogold (FG), 3 weeks prior to a single injection of 6-hydroxydopamine (6-OHDA) in the right striatum. One week before the 6-OHDA injection, the animals received injections with lentiviral vectors expressing neublastin [neublastin], GDNF [GDNF] or the Green Fluorescent Protein [GFP] as indicated in the figure. Twenty one days after the 6-OHDA injections, the number of FG-labelled neurons in both sides of the striata were determined. The figure shows the percentage [%FG lesion/intact] of FG-labelled neurons in the lesioned (right) side verses the intact (left) side of the striata of the three groups of animals.

Example 10

Production of Antibodies

To prepare antibodies against neublastin, two rabbits were immunised with either peptide 1: CRPTRYEAVSFMD-VNST (amino acids 108–124 of SEQ ID NO: 9); or peptide 2: ALRPPPGSRPVSQPC (amino acids 93–107 of SEQ ID NO: 9) conjugated to carrier protein at 3 week intervals. Two rabbits for each peptide were immunized at week 0, 3, 6 and 10, and bleeds were collected at week 7 and 11. The second bleed was affinity purified via a peptide affinity column. The antibodies were named Ab-1 and Ab-2, according to the peptide.

Western blot: $2 \times 10^6$ HiB5 cells, stably transfected with the cDNA for neublastin (Hib5pUbi1zNBN22), or untransfected HiB5 cells, were incubated overnight in serum free medium with $N_2$ supplement (GIBCO). The medium was concentrated on small concentrators with cut-off membranes of 5 kDa (Millipore, Bedford, Mass.). Concentrated samples were added 5×Laemmli sample buffer and were heated to 95° C. for 5 minutes. Samples were separated by SDS polyacrylamide gel electrophoresis on 15% acrylamide gels and transferred to PVDF-membranes. Residual protein-binding sites were blocked with 5% non-fat dry milk in PBS with 0.1% Tween-20. Membranes were incubated overnight with neublastin antibody (1:1000), followed by incubation with a secondary anti-rabbit or anti-mouse IgG antibody conjugated to horseradish peroxidase (1:2000).

Immunostaining was visualized using enhanced chemoluminiscence Plus (ECL+) according to the manufacturer's instructions (Amersham). The results of these experiments are shown in FIG. 3 and Example 5.

Using standard techniques, we also raised rabbit polyclonal antibodies against the following peptides:

Peptide R27: GPGSRARAAGARGC (amino acids 30–43 of SEQ ID NO:9);

Peptide R28: LGHRSDELVRFRFC (amino acids 57–70 of SEQ ID NO:9);

Peptide R29: CRRARSPHDLSL (amino acids 74–85 of SEQ ID NO:9);

Peptide R30: LRPPPGSRPVSQPC (amino acids 94–107 of SEQ ID NO:9); and

Peptide R31: STWRTVDRLSATAC (amino acids 123–136 of SEQ ID NO:9).

Only peptides R30 and R31, relatively close to the C-terminus, recognized the denatured protein under reducing conditions on a Western blot.

| | Description of Sequences Contained in the Sequence Listing | |
|---|---|---|
| SEQ ID NO.: 1 | Human neublastin nucleic acid. | 865 bp |
| SEQ ID NO.: 2 | Human neublastin polypeptide from sequence 1. | 200 aa |
| SEQ ID NO.: 3 | Coding region (CDS) of a human pre-pro- polypeptide. | 861 bp |
| SEQ ID NO.: 4 | Human neublastin polypeptide from sequence 3. | 238 aa |
| SEQ ID NO.: 5 | Variant of human neublastin in sequence 4 (Xaa is Asn or Thr; Yaa is Ala or Pro). | 140 aa |
| SEQ ID NO.: 6 | Variant of human neublastin in sequence 4 (Xaa is Asn or Thr; Yaa is Ala or Pro). | 116 aa |
| SEQ ID NO.: 7 | Variant of human neublastin in sequence 4 (Xaa is Asn or Thr; Yaa is Ala or Pro). | 113 aa |
| SEQ ID NO.: 8 | cDNA from positive colony PCR of human fetal brain cDNA. | 861 bp |
| SEQ ID NO.: 9 | human fetal brain pre-pro-neublastin polypeptide including "stop" (corresponds to seq. 8) | 221 aa |
| SEQ ID NO.: 10 | Variant of pre-pro-neublastin (seq. 9) NBN140, 14.7 kD. | 140 aa |
| SBQ ID NO.: 11 | Variant of pre-pro-neublastin (seq. 9) NBN116, 12.4 kD. | 116 aa |
| SEQ ID NO.: 12 | Variant of pre-pro-neublastin (seq. 9) NBN113, 12.1 kD. | 113 aa |
| SEQ ID NO.: 13 | PCR product from screen of human fetal brain cDNA master plate using SEQ. ID. NOS. 17 and 18 as primers. | 102 bp |
| SEQ ID NO.: 14 | PCR product from screen of mouse fetal cDNA master plate using SEQ. ID. NOS. 21 and 22 as primers. | 220 bp |
| SEQ ID NO.: 15 | Full length mouse neublastin cDNA. | 2136 bp |
| SEQ ID NO.: 16 | Mouse pre-pro-neublastin polypeptide. | 224 aa |
| SEQ ID NO.: 17 | "NBNint.sence" Top Primer for NBN from human fetal brain cDNA complementary to bases 551–568 of SEQ. ID. NO. 1 | 18 nt |
| SEQ ID NO.: 18 | "NBNint.antisence" Bottom Primer for NBN from human fetal brain cDNA reverse complement to bases 633–652 of SEQ. ID. NO. 1 | 20 nt |
| SEQ ID NO.: 19 | "NBNext.sence" Top Primer for whole human brain mRNA RT-PCR complementary to bases 58–74 of SEQ. ID. NO. 8. | 17 nt |
| SEQ ID NO.: 20 | "NBNext.antisence" Bottom Primer for whole human brain mRNA RT-PCR reverse complement to bases 850–865 of SEQ. ID. NO. 8. | 16 nt |
| SEQ ID NO.: 21 | "NBNint.sence" NBN C2 Primer for screening mouse fetal cDNA master plate complementary to bases 1398–1415 of SEQ. ID. NO. 15. | 18 nt |

-continued

Description of Sequences Contained in the Sequence Listing

| | | |
|---|---|---|
| SEQ ID NO.: 22 | "NBNint.antisence" NBN C2as Primer for screening mouse fetal cDNA master plate. Reverse complement to bases 1598–1617 of SEQ. ID. NO. 15. | 20 nt |
| SEQ ID NO.: 23 | Primer Pair 1 Sense PCR Primer for human genomic DNA amplification complementary to bases 60–88 of SEQ. ID. NO. 3. | 29 nt |
| SEQ ID NO.: 24 | Primer Pair 1 Antisense PCR Primer for human genomic DNA amplification Reverse complement to bases 835–861 of SEQ. ID. NO. 3. | 27 nt |
| SEQ ID NO.: 25 | Primer Pair 2 Sense PCR Primer for human genomic DNA amplification complementary to bases 1–35 of SEQ. ID. NO. 3. | 35 nt |
| SEQ ID NO.: 26 | Primer Pair 2 Antisense PCR Primer for human genomic DNA amplification reverse complement to bases 786–819 of SEQ. ID. NO. 3. | 34 nt |
| SEQ ID NO.: 27 | Antisense alkaline phosphatase conjugated hybridization probe, complimentary to bases 1140–1169 of mouse neuroblastin cDNA. | 30 nt |
| SEQ ID NO.: 28 | "NBNext.sence" Top Primer for whole human brain mRNA RT-PCR complementary to bases 1–16 of SEQ. ID. NO. 1 | 16 nt |
| SEQ ID NO.: 29 | Syngene from FIG. 14 of neublastin. | 351 nt |
| SEQ ID NO.: 30 | Syngene from FIG. 15 of Hisneublastin. | 414 nt |
| SEQ ID NO.: 31 | Primer for isolating neublastin. | 39 nt |
| SEQ ID NO.: 32 | Primer for isolating neublastin. | 39 nt |
| SEQ ID NO.: 33 | "NBNint.antisence" NBN primer; reverse complement to bases 715–730 of SEQ. ID. NO. 8. | 16 nt |

We claim:

1. An isolated neublastin nucleic acid comprising a nucleotide sequence selected from the group consisting of:
   a) nucleotides 405–719 of SEQ ID NO. 1;
   b) a nucleotide sequence that hybridizes specifically to a complement sequence of nucleotides 405–719 of SEQ ID NO. 1 under high stringency solution hybridization conditions;
      wherein the nucleotide sequence codes on expression for a neublastin polypeptide with neurotrophic activity and comprising all of the following characteristics:
      (i) seven conserved cysteine residues at positions 8, 35, 39, 72, 73, 101, and 103 when numbered in accordance with SEQ ID NO. 2;
      (ii) amino acid residues as follows:
         C at position 8, L at position 10, V at position 17, L at position 20, G at position 21, L at position 22, G at position 23, E at position 28, F at position 32, R at position 33, F at position 34, C at position 35, G at position 37, C at position 39, C at position 72, C at position 73, R at position 74, P at position 75, F at position 83, D at position 85, S at position 97, A at position 98, C at position 101 and C at position 103, each when numbered in accordance with SEQ ID NO. 2;
      (iii) an LGLG repeat, an FRFC motif, a QPCCRP motif, and a SATACGC motif
      (iv) an amino acid sequence comprising at least 90% sequence identity to $AA_1$–$AA_{105}$ of SEQ ID NO. 2.

2. An isolated nucleic acid sequence comprising a nucleotide sequence selected from the group consisting of:
   a) nucleotides 405–719 of SEQ ID NO. 1 or nucleotides 379–717 of SEQ ID NO. 3;
   b) a nucleotide sequence that hybridizes specifically to a complement sequence of nucleotides 405–719 of SEQ ID NO. 1 or to nucleotides 379–717 of SEQ ID NO. 3 under high stringency solution hybridization conditions;
      wherein the nucleotide sequence codes on expression for a neublastin polypeptide with neurotrophic activity and comprising:
      (i) seven conserved cysteine residues at positions 8, 35, 39, 72, 73, 101, and 103 when numbered in accordance with SEQ ID NO. 2;
      (ii) amino acid residues as follows:
         C at position 43, L at position 45, V at position 52, L at position 55, G at position 56, L at position 57, G at position 58, E at position 63, F at position 67, R at position 68, C at position 70, G at position 72, C at position 74, C at position 107, C at position 108, R at position 109, P at position 110, F at position 118, D at position 120, S at position 132, A at position 133, C at position 136 and C at position 138, each when numbered in accordance with SEQ ID NO. 4;
      (iii) an LGLG repeat, an FRFC motif, a QPCCRP motif, and a SATACGC motif; and
      (iv) an amino acid sequence comprising at least 90% sequence identity to $AA_1$–$AA_{105}$ of SEQ ID NO. 2 or at least 90% sequence identity to $AA_1$–$AA_{113}$ of SEQ ID NO. 7.

3. An isolated nucleic acid that comprises a nucleic acid sequence that is complementary to the nucleic acid of claims 1 or 2.

4. A vector comprising the nucleic acid of any one of claims 1–2.

5. The vector of claim 4, wherein said vector is an expression vector.

6. A method of using the vector of claim 5, comprising causing a polypeptide encoded by said nucleic acid to be expressed in vitro from said nucleic acid.

7. A cell transformed in vitro with a nucleic acid of any one of claims 1–2.

8. The cell of claim 7, wherein said cell is selected from the group consisting of mammalian cells, fungal cells, yeast cells, insect cells and bacterial cells.

9. The cell of claim 8, wherein said cell is a Chinese hamster ovary cell.

10. A cell of claim 8, wherein said cell is a cell derived from the mammalian central nervous system.

11. An isolated nucleic acid molecule encoding a neublastin polypeptide, wherein the nucleic acid molecule has the sequence set forth in SEQ ID NOS. 29 or 30.

12. A vector comprising the nucleic acid of claim 11.

13. The vector of claim 12, wherein said vector is an expression vector.

14. A method of using the vector of claim 13, comprising causing a polypeptide encoded by said nucleic acid to be expressed in vitro from said nucleic acid.

15. A cell transformed in vitro with a nucleic acid of claim 11.

16. The cell of claim 15, wherein said cell is a bacterial cell.

17. An isolated neublastin nucleic acid comprising a nucleotide sequence selected from the group consisting of:
   a) the nucleotide sequence of nucleotides 379–717 of SEQ. ID. NO. 8
   b) a nucleotide sequence that hybridizes specifically to a complement sequence of nucleotides 379–717 of SEQ ID NO. 8 under high stringency solution hybridization conditions;
      wherein the nucleotide sequence codes on expression for a neublastin polypeptide with neurotrophic activity and comprising:
      (i) seven conserved cysteine residues at positions 8, 35, 39, 72, 73, 101, and 103 when numbered in accordance with SEQ ID NO. 2;
      (ii) amino acid residues as follows:
         C at position 43, L at position 45, V at position 52, L at position 55, G at position 56, L at position 57, G at position 58, E at position 63, F at position 67, R at position 68, C at position 70, G at position 72, C at position 74, C at position 107, C at position 108, R at position 109, P at position 110, F at position 118, D at position 120, S at position 132, A at position 133, C at position 136 and C at position 138, each when numbered in accordance with SEQ ID NO. 8;
      (iii) an LGLG repeat, an FRFC motif, a QPCCRP motif, and a SATACGC motif; and
      (iv) an amino acid sequence comprising at least 90% sequence identity to $AA_1$–$AA_{105}$ of SEQ ID NO. 2 or at least 90% sequence identity to $AA_1$–$AA_{113}$ of SEQ ID NO. 7 or at least 90% sequence identity to $AA_1$–$AA_{113}$ of SEQ ID NO. 12.

18. A vector comprising a nucleic acid of claim 17.

19. The vector of claim 18, wherein said vector is an expression vector.

20. A method of producing a neublastin mRNA, comprising transforming the expression vector according to claim 19 into a host cell capable of expressing mRNA from the expression vector.

21. A cell transformed in vitro with a nucleic acid of claim 17.

22. The cell of claim 21, wherein said cell is a bacterial cell.

* * * * *

UNITED STATES PATENT AND TRADEMARK OFFICE
CERTIFICATE OF CORRECTION

PATENT NO.    : 6,593,133 B1
DATED         : July 15, 2003
INVENTOR(S)   : Teit E. Johansen, Nikolaj Blom and Claus Hansen It is certified that error appears in the above-identified patent and that said Letters Patent is hereby corrected as shown below:

Title page,
Item [63], Foreign Application Priority Data, the first entry should read -- Jul. 6, 1998 --.

Column 6,
Line 53, should read -- manipulated polypeptides --;

Column 10,
Line 24, should read -- $AA_{107}$-$AA_{140}$ --;
Line 26, should read -- $AA_{191}$-$AA_{224}$ --;

Column 15,
Line 66, should read -- neurotrophic --;

Column 20,
Line 60, should read -- VIIIth cranial nerve --;

Column 26,
Line 16, should read -- AC005051 --;

Column 29,
Line 66, should read -- E13.5 --;

UNITED STATES PATENT AND TRADEMARK OFFICE
CERTIFICATE OF CORRECTION

PATENT NO. : 6,593,133 B1
DATED : July 15, 2003
INVENTOR(S) : Teit E. Johansen, Nikolaj Blom and Claus Hansen It is certified that error appears in the above-identified patent and that said Letters Patent is hereby corrected as shown below:

Column 32,
Table 3 should read:

--Amino Acid Sequence Comparison of Neublastin (SEQ ID NO:35) to
Persephin(SEQ ID NO:36), Neurturin (SEQ ID NO:34), and GDNF (SEQ ID NO:37)

```
Neurturin-full      ------------------MQRWKAAALASVLCSSVLSIWMCREGLLLSHRLGPA
Neublastin          MELGLGGLSTLSHCPWPRRQPALWPTLAALALLSSVAEASLGSAPRSPAPREGPPP
Persephin-full      -------------------------------------------------------
GDNF_HUMAN-full     -----MKLWDVVAVCLVLLHTASAFPLPAGKRPPEAPAEDRSLGRRRAPFALSSDS Neurturin-full      LVPLHRLPRTLDARIARLAQYRALLQGAPDAMELRELTPWAGRPPGPRRRAGPRRR
Neublastin          VLASPAGHLPGGRTARWCSGRARRPPPQPSRPAPPPPAPPSALPRGGRAARAGGPG
Persephin-full      -MAVGKFLLGSLLLLSLQLGQGWGPDARGVPVADGEFSSEQVAKAGGTWLGTHRPL
GDNF_HUMAN-full     NMPEDYPDQFDDVMDFIQATIKRLKRSPDKQMAVLPRRERNRQAAAANPENSRGKG Neurturin-full      RARARLGARPCGLRELEVRVSELGLGYASDETVLFRYCAGACEA-AARVYDLGLRR
Neublastin          SRARAAGARGCRLRSQLVPVRALGLGHRSDELVRFRFCSGSCRR-ARSPHDLSLAS
Persephin-full      ARLRRALSGPCQLWSLTLSVAELGLGYASEEKVIFRYCAGSCPRGARTQHGLALAR
GDNF_HUMAN-full     RRGQRGKNRGCVLTAIHLNVTDLGLGYETKEELIFRYCSGSCDA-AETTYDKILKN
                    * *    : * ****: :.*  : **:*:*:*   *   :. *

Neurturin-full      LRQRRRLRRE---RVRAQPCCRPTAYEDEVSFLDAHSRYHTVHELSARECACV-
Neublastin          LLGAGALRPPPGSRPVSQPCCRPTRYE-AVSFMDVNSTWRTVDRLSATACGCLG
Persephin-full      LQGQGPAHGG--------PCCRPTRYT-DVAFLDDRHRWQRLPQLSAAACGCGG
GDNF_HUMAN-full     LSRNRRLVSD----KVGQACCRPIAFDDDLSFLDDNLVYHILRKHSAKRCGCI-
                          *          .****  :    ::*:*  . :: :  . **  *.*
```

*indicates positions which have a single, fully conserved residue.
:indicates that one of the following 'strong' groups is fully conserved:
-STA, NEQK, NHQK, NDEQ, QHRK, MILV, MILF, HY, FYW.
.indicates that one of the following 'weaker' groups is fully conserved:
-CSA, ATV, SAG, STNK, STPA, SGND, SNDEQK, NDEQHK, NEQHRK, VLIM, HFY.--

Column 34,
Line 44, should read -- NO:11 --;

Column 36,
Line 55, should read -- 100 $\mu$l of 1 $\mu$g/ml --;

Column 38,
Line 33, should read -- Fc$\gamma$ --;

Column 41,
Line 17, should read -- HiB5pUbilzNBN22 --.

UNITED STATES PATENT AND TRADEMARK OFFICE
CERTIFICATE OF CORRECTION

PATENT NO.    : 6,593,133 B1
DATED         : July 15, 2003
INVENTOR(S)   : Teit E. Johansen, Nikolaj Blom and Claus Hansen It is certified that error appears in the above-identified patent and that said Letters Patent is hereby corrected as shown below:

Column 83,
Line 65, Claim 6 should read -- 6. A method of producing a neublastin mRNA, comprising transforming the expression vector according to claim 5 into a host cell capable of expressing mRNA from the expression vector. --

Column 84,
Line 16, Claim 14 should read -- 14. A method of producing a neublastin mRNA, comprising transforming the expression vector according to claim 13 into a host cell capable of expressing mRNA from the expression vector. --

Signed and Sealed this

Sixteenth Day of November, 2004

JON W. DUDAS
*Director of the United States Patent and Trademark Office*

SEQUENCE LISTING

<160> NUMBER OF SEQ ID NOS: 43

<210> SEQ ID NO 1
<211> LENGTH: 865
<212> TYPE: DNA
<213> ORGANISM: Homo sapiens
<220> FEATURE:
<221> NAME/KEY: CDS
<222> LOCATION: (120)..(719)
<220> FEATURE:
<221> NAME/KEY: 5'UTR
<222> LOCATION: (1)..(119)
<220> FEATURE:
<221> NAME/KEY: 3'UTR
<222> LOCATION: (721)..(865)
<220> FEATURE:
<221> NAME/KEY: sig_peptide
<222> LOCATION: (120)..(179)
<220> FEATURE:
<221> NAME/KEY: mat_peptide
<222> LOCATION: (405)..(719)
<220> FEATURE:
<221> NAME/KEY: misc_structure
<222> LOCATION: (661)..(663)
<223> OTHER INFORMATION: CARBOHYD: Glycosylated Asparagine at Asn87
<220> FEATURE:
<221> NAME/KEY: misc_structure
<222> LOCATION: (426)..(623)
<223> OTHER INFORMATION: DISULFID - Cys8-Cys73 disulfide bridge
<220> FEATURE:
<221> NAME/KEY: misc_structure
<222> LOCATION: (507)..(707)
<223> OTHER INFORMATION: DISULFID: Cys35-Cys101 disulfide bridge
<220> FEATURE:
<221> NAME/KEY: misc_structure
<222> LOCATION: (519)..(713)
<223> OTHER INFORMATION: DISULFID: Cys39-Cys103 disulfide bridge
<220> FEATURE:
<221> NAME/KEY: misc_structure
<222> LOCATION: (616)..(619)
<223> OTHER INFORMATION: DISULFID: Cys72-Cys72 interchain disulfide
      bridge

<400> SEQUENCE: 1

```
ctaggagccc atgcccggcc tgatctcagc ccgaggacag cccctccttg aggtccttcc      60
tccccaagcc cacctgggtg ccctcttttct ccctgaggct ccacttggtc tctccgcgc     119
```

-continued

```
atg cct gcc ctg tgg ccc acc ctg gcc gct ctg gct ctg ctg agc agc        167
Met Pro Ala Leu Trp Pro Thr Leu Ala Ala Leu Ala Leu Leu Ser Ser
-95             -90             -85             -80 gtc gca gag gcc tcc ctg ggc tcc gcg ccc cgc agc cct gcc ccc cgc        215
Val Ala Glu Ala Ser Leu Gly Ser Ala Pro Arg Ser Pro Ala Pro Arg
        -75             -70             -65 gaa ggc ccc ccg cct gtc ctg gcg tcc ccc gcc ggc cac ctg ccg ggg        263
Glu Gly Pro Pro Pro Val Leu Ala Ser Pro Ala Gly His Leu Pro Gly
        -60             -55             -50 gga cgc acg gcc cgc tgg tgc agt gga aga gcc cgg cgg ccg cgc cgc        311
Gly Arg Thr Ala Arg Trp Cys Ser Gly Arg Ala Arg Arg Pro Arg Arg
        -45             -40             -35 aga cac ttc tcg gcc cgc gcc ccc gcc gcc tgc acc ccc atc tgc tct        359
Arg His Phe Ser Ala Arg Ala Pro Ala Ala Cys Thr Pro Ile Cys Ser
        -30             -25             -20 tcc ccg cgg gtc cgc gcg gcg cgg ctg ggg ggc cgg gca gcg cgc tcg        407
Ser Pro Arg Val Arg Ala Ala Arg Leu Gly Gly Arg Ala Ala Arg Ser
-15             -10             -5              -1   1 ggc agc ggg ggc gcg ggg tgc cgc ctg cgc tcg cag ctg gtg ccg gtg        455
Gly Ser Gly Gly Ala Gly Cys Arg Leu Arg Ser Gln Leu Val Pro Val
                5               10              15 cgc gcg ctc ggc ctg ggc cac cgc tcc gac gag ctg gtg cgt ttc cgc        503
Arg Ala Leu Gly Leu Gly His Arg Ser Asp Glu Leu Val Arg Phe Arg
        20              25              30 ttc tgc acc ggc tcc tgc ccg cgc gcg cgc tct cca cac gac ctc agc        551
Phe Cys Thr Gly Ser Cys Pro Arg Ala Arg Ser Pro His Asp Leu Ser
        35              40              45 ctg gcc agc cta ctg ggc gcc ggg gcc ctg cga ccg ccc ccg ggc tcc        599
Leu Ala Ser Leu Leu Gly Ala Gly Ala Leu Arg Pro Pro Pro Gly Ser
50              55              60              65 cgg ccc gtc agc cag ccc tgc tgc cga ccc acg cgc tac gaa gcg gtc        647
Arg Pro Val Ser Gln Pro Cys Cys Arg Pro Thr Arg Tyr Glu Ala Val
                70              75              80 tcc ttc atg gac gtc aac agc acc tgg aga acc gtg gac cgc ctc tcc        695
Ser Phe Met Asp Val Asn Ser Thr Trp Arg Thr Val Asp Arg Leu Ser
        85              90              95 gcc acc gcc tgc ggc tgc ctg ggc tgagggctcg ctccagggct ttgcagactg       749
Ala Thr Ala Cys Gly Cys Leu Gly
        100             105 gaccct tacc ggtggctctt cctgcctggg accctcccgc agagtccac tagccagcgg      809 cctcagccag ggacgaaggc ctcaaagctg agaggcccct gccggtgggt gatgga          865
```

<210> SEQ ID NO 2
<211> LENGTH: 200
<212> TYPE: PRT
<213> ORGANISM: Homo sapiens

<400> SEQUENCE: 2

```
Met Pro Ala Leu Trp Pro Thr Leu Ala Ala Leu Ala Leu Leu Ser Ser
-95             -90             -85             -80

Val Ala Glu Ala Ser Leu Gly Ser Ala Pro Arg Ser Pro Ala Pro Arg
        -75             -70             -65

Glu Gly Pro Pro Pro Val Leu Ala Ser Pro Ala Gly His Leu Pro Gly
        -60             -55             -50

Gly Arg Thr Ala Arg Trp Cys Ser Gly Arg Ala Arg Arg Pro Arg Arg
        -45             -40             -35

Arg His Phe Ser Ala Arg Ala Pro Ala Ala Cys Thr Pro Ile Cys Ser
        -30             -25             -20
```

-continued

```
Ser Pro Arg Val Arg Ala Ala Arg Leu Gly Gly Arg Ala Ala Arg Ser
-15                 -10                  -5                  -1   1

Gly Ser Gly Gly Ala Gly Cys Arg Leu Arg Ser Gln Leu Val Pro Val
             5                  10                  15

Arg Ala Leu Gly Leu Gly His Arg Ser Asp Glu Leu Val Arg Phe Arg
         20                  25                  30

Phe Cys Thr Gly Ser Cys Pro Arg Ala Arg Ser Pro His Asp Leu Ser
     35                  40                  45

Leu Ala Ser Leu Leu Gly Ala Gly Ala Leu Arg Pro Pro Pro Gly Ser
 50                  55                  60                  65

Arg Pro Val Ser Gln Pro Cys Cys Arg Pro Thr Arg Tyr Glu Ala Val
             70                  75                  80

Ser Phe Met Asp Val Asn Ser Thr Trp Arg Thr Val Asp Arg Leu Ser
             85                  90                  95

Ala Thr Ala Cys Gly Cys Leu Gly
            100                 105
```

<210> SEQ ID NO 3
<211> LENGTH: 861
<212> TYPE: DNA
<213> ORGANISM: Homo sapiens
<220> FEATURE:
<221> NAME/KEY: CDS
<222> LOCATION: (7)..(717)
<220> FEATURE:
<221> NAME/KEY: 5'UTR
<222> LOCATION: (1)..(6)
<220> FEATURE:
<221> NAME/KEY: 3'UTR
<222> LOCATION: (718)..(861)
<220> FEATURE:
<221> NAME/KEY: sig_peptide
<222> LOCATION: (7)..(174)
<220> FEATURE:
<221> NAME/KEY: mat_peptide
<222> LOCATION: (298)..(717)
<220> FEATURE:
<221> NAME/KEY: mat_peptide
<222> LOCATION: (370)..(717)
<220> FEATURE:
<221> NAME/KEY: mat_peptide
<222> LOCATION: (379)..(717)
<220> FEATURE:
<221> NAME/KEY: misc_structure
<222> LOCATION: (661)..(663)
<223> OTHER INFORMATION: CARBOHYD: glycosylated Asparagine as Asn122
<220> FEATURE:
<221> NAME/KEY: misc_structure
<222> LOCATION: (424)..(621)
<223> OTHER INFORMATION: DISULFID: Cys43-Cys108 disulfide bridge
<220> FEATURE:
<221> NAME/KEY: misc_structure
<222> LOCATION: (505)..(705)
<223> OTHER INFORMATION: DISULFID: Cys70-Cys136 disulfide bridge
<220> FEATURE:
<221> NAME/KEY: misc_structure
<222> LOCATION: (517)..(711)
<223> OTHER INFORMATION: DISULFID: Cys74-Cys138 disulfide bridge
<220> FEATURE:
<221> NAME/KEY: misc_structure
<222> LOCATION: (616)..(618)
<223> OTHER INFORMATION: DISULFID: Cys107-Cys107 interchain disulfide
      bridge

<400> SEQUENCE: 3

```
gagccc atg ccc ggc ctg atc tca gcc cga gga cag ccc ctc ctt gag        48
       Met Pro Gly Leu Ile Ser Ala Arg Gly Gln Pro Leu Leu Glu
       -95                 -90                 -85
```

```
gtc ctt cct ccc caa gcc cac ctg ggt gcc ctc ttt ctc cct gag gct        96
Val Leu Pro Pro Gln Ala His Leu Gly Ala Leu Phe Leu Pro Glu Ala
            -80              -75              -70 cca ctt ggt ctc tcc gcg cag cct gcc ctg tgg ccc acc ctg gcc gct       144
Pro Leu Gly Leu Ser Ala Gln Pro Ala Leu Trp Pro Thr Leu Ala Ala
        -65              -60              -55 ctg gct ctg ctg agc agc gtc gca gag gcc tcc ctg ggc tcc gcg ccc       192
Leu Ala Leu Leu Ser Ser Val Ala Glu Ala Ser Leu Gly Ser Ala Pro
    -50              -45              -40 cgc agc cct gcc ccc cgc gaa ggc ccc ccg cct gtc ctg gcg tcc ccc       240
Arg Ser Pro Ala Pro Arg Glu Gly Pro Pro Pro Val Leu Ala Ser Pro
-35              -30              -25              -20 gcc ggc cac ctg ccg ggg gga cgc acg gcc cgc tgg tgc agt gga aga       288
Ala Gly His Leu Pro Gly Gly Arg Thr Ala Arg Trp Cys Ser Gly Arg
                -15              -10              -5 gcc cgg cgg ccg ccg ccg cag cct tct cgg ccc gcg ccc ccg ccg cct       336
Ala Arg Arg Pro Pro Pro Gln Pro Ser Arg Pro Ala Pro Pro Pro Pro
        -1  1               5                10 gca ccc cca tct gct ctt ccc cgc ggg ggc cgc gcg gcg cgg gct ggg       384
Ala Pro Pro Ser Ala Leu Pro Arg Gly Gly Arg Ala Ala Arg Ala Gly
    15              20              25 ggc ccg ggc aac cgc gct cgg gca gcg ggg gcg cgg ggc tgc cgc ctg       432
Gly Pro Gly Asn Arg Ala Arg Ala Ala Gly Ala Arg Gly Cys Arg Leu
30              35              40              45 cgc tcg cag ctg gtg ccg gtg cgc gcg ctc ggc ctg ggc cac cgc tcc       480
Arg Ser Gln Leu Val Pro Val Arg Ala Leu Gly Leu Gly His Arg Ser
                50              55              60 gac gag ctg gtg cgt ttc cgc ttc tgc agc ggc tcc tgc cgc cgc gcg       528
Asp Glu Leu Val Arg Phe Arg Phe Cys Ser Gly Ser Cys Arg Arg Ala
        65              70              75 cgc tct cca cac gac ctc agc ctg gcc agc cta ctg ggc gcc ggg gcc       576
Arg Ser Pro His Asp Leu Ser Leu Ala Ser Leu Leu Gly Ala Gly Ala
    80              85              90 ctg cga ccg ccc ccg ggc tcc cgg ccc gtc agc cag ccc tgc tgc cga       624
Leu Arg Pro Pro Pro Gly Ser Arg Pro Val Ser Gln Pro Cys Cys Arg
95              100             105 ccc acg cgc tac gaa gcg gtc tcc ttc atg gac gtc aac agc acc tgg       672
Pro Thr Arg Tyr Glu Ala Val Ser Phe Met Asp Val Asn Ser Thr Trp
110             115             120             125 aga acc gtg gac cgc ctc tcc gcc aac ccc tgc ggc tgc ctg ggc           717
Arg Thr Val Asp Arg Leu Ser Ala Asn Pro Cys Gly Cys Leu Gly
            130             135             140 tgagggctcg ctccagggct tgcagactg gaccttacc ggtggctctt cctgcctggg       777
accctcccgc agagtccac tagccagcgg cctcagccag ggacgaaggc ctcaaagctg       837
agaggcccct gccggtgggt gatg                                            861

<210> SEQ ID NO 4
<211> LENGTH: 237
<212> TYPE: PRT
<213> ORGANISM: Homo sapiens

<400> SEQUENCE: 4

Met Pro Gly Leu Ile Ser Ala Arg Gly Gln Pro Leu Leu Glu Val Leu
            -95              -90              -85
Pro Pro Gln Ala His Leu Gly Ala Leu Phe Leu Pro Glu Ala Pro Leu
    -80              -75              -70
Gly Leu Ser Ala Gln Pro Ala Leu Trp Pro Thr Leu Ala Ala Leu Ala
-65              -60              -55              -50
Leu Leu Ser Ser Val Ala Glu Ala Ser Leu Gly Ser Ala Pro Arg Ser
        -45              -40              -35
Pro Ala Pro Arg Glu Gly Pro Pro Pro Val Leu Ala Ser Pro Ala Gly
```

-continued

```
              -30                 -25                 -20
    His Leu Pro Gly Gly Arg Thr Ala Arg Trp Cys Ser Gly Arg Ala Arg
            -15                 -10                  -5
    Arg Pro Pro Gln Pro Ser Arg Pro Ala Pro Pro Pro Ala Pro
     -1   1                   5                  10                  15
    Pro Ser Ala Leu Pro Arg Gly Gly Arg Ala Ala Arg Ala Gly Gly Pro
                         20                  25                  30
    Gly Asn Arg Ala Arg Ala Ala Gly Ala Arg Gly Cys Arg Leu Arg Ser
                     35                  40                  45
    Gln Leu Val Pro Val Arg Ala Leu Gly Leu Gly His Arg Ser Asp Glu
                 50                  55                  60
    Leu Val Arg Phe Arg Phe Cys Ser Gly Ser Cys Arg Arg Ala Arg Ser
             65                  70                  75
    Pro His Asp Leu Ser Leu Ala Ser Leu Leu Gly Ala Gly Ala Leu Arg
         80                  85                  90                  95
    Pro Pro Pro Gly Ser Arg Pro Val Ser Gln Pro Cys Cys Arg Pro Thr
                        100                 105                 110
    Arg Tyr Glu Ala Val Ser Phe Met Asp Val Asn Ser Thr Trp Arg Thr
                    115                 120                 125
    Val Asp Arg Leu Ser Ala Asn Pro Cys Gly Cys Leu Gly
                130                 135                 140

SEQ ID NO 5
LENGTH: 140
TYPE: PRT
ORGANISM: Homo sapiens
FEATURE:
NAME/KEY: VARIANT
LOCATION: (134)
OTHER INFORMATION: Wherein Xaa at position 134 designates Asn or Thr
FEATURE:
NAME/KEY: VARIANT
LOCATION: (135)
OTHER INFORMATION: Wherein Xaa at position 135 designates Ala or Pro

SEQUENCE: 5

Pro Pro Pro Gln Pro Ser Arg Pro Ala Pro Pro Pro Ala Pro Pro
  1               5                  10                  15

Ser Ala Leu Pro Arg Gly Gly Arg Ala Ala Arg Ala Gly Gly Pro Gly
                 20                  25                  30

Asn Arg Ala Arg Ala Ala Gly Ala Arg Gly Cys Arg Leu Arg Ser Gln
             35                  40                  45

Leu Val Pro Val Arg Ala Leu Gly Leu Gly His Arg Ser Asp Glu Leu
         50                  55                  60

Val Arg Phe Arg Phe Cys Ser Gly Ser Cys Arg Arg Ala Arg Ser Pro
 65                  70                  75                  80

His Asp Leu Ser Leu Ala Ser Leu Leu Gly Ala Gly Ala Leu Arg Pro
                 85                  90                  95

Pro Pro Gly Ser Arg Pro Val Ser Gln Pro Cys Cys Arg Pro Thr Arg
            100                 105                 110

Tyr Glu Ala Val Ser Phe Met Asp Val Asn Ser Thr Trp Arg Thr Val
        115                 120                 125

Asp Arg Leu Ser Ala Xaa Xaa Cys Gly Cys Leu Gly
    130                 135                 140

<210> SEQ ID NO 6
<211> LENGTH: 116
<212> TYPE: PRT
<213> ORGANISM: Homo sapiens
<220> FEATURE:
<221> NAME/KEY: VARIANT
<222> LOCATION: (110)
<223> OTHER INFORMATION: Wherein Xaa at position 110 designates Asn or
      Thr
<220> FEATURE:
<221> NAME/KEY: VARIANT
<222> LOCATION: (111)
<223> OTHER INFORMATION: Wherein Xaa at position 111 designates Ala or
```

Pro

<400> SEQUENCE: 6

| Ala | Ala | Arg | Ala | Gly | Gly | Pro | Gly | Asn | Arg | Ala | Arg | Ala | Ala | Gly | Ala |
|---|---|---|---|---|---|---|---|---|---|---|---|---|---|---|---|
| 1 | | | | 5 | | | | | 10 | | | | | 15 | |

| Arg | Gly | Cys | Arg | Leu | Arg | Ser | Gln | Leu | Val | Pro | Val | Arg | Ala | Leu | Gly |
|---|---|---|---|---|---|---|---|---|---|---|---|---|---|---|---|
| | | | 20 | | | | | 25 | | | | | 30 | | |

| Leu | Gly | His | Arg | Ser | Asp | Glu | Leu | Val | Arg | Phe | Arg | Phe | Cys | Ser | Gly |
|---|---|---|---|---|---|---|---|---|---|---|---|---|---|---|---|
| | | 35 | | | | | 40 | | | | | 45 | | | |

| Ser | Cys | Arg | Arg | Ala | Arg | Ser | Pro | His | Asp | Leu | Ser | Leu | Ala | Ser | Leu |
|---|---|---|---|---|---|---|---|---|---|---|---|---|---|---|---|
| | 50 | | | | | 55 | | | | | 60 | | | | |

| Leu | Gly | Ala | Gly | Ala | Leu | Arg | Pro | Pro | Pro | Gly | Ser | Arg | Pro | Val | Ser |
|---|---|---|---|---|---|---|---|---|---|---|---|---|---|---|---|
| 65 | | | | | 70 | | | | | 75 | | | | | 80 |

| Gln | Pro | Cys | Cys | Arg | Pro | Thr | Arg | Tyr | Glu | Ala | Val | Ser | Phe | Met | Asp |
|---|---|---|---|---|---|---|---|---|---|---|---|---|---|---|---|
| | | | | 85 | | | | | 90 | | | | | 95 | |

| Val | Asn | Ser | Thr | Trp | Arg | Thr | Val | Asp | Arg | Leu | Ser | Ala | Xaa | Xaa | Cys |
|---|---|---|---|---|---|---|---|---|---|---|---|---|---|---|---|
| | | | 100 | | | | | 105 | | | | | 110 | | |

| Gly | Cys | Leu | Gly |
|---|---|---|---|
| | | | 115 |

<210> SEQ ID NO 7
<211> LENGTH: 113
<212> TYPE: PRT
<213> ORGANISM: Homo sapiens
<220> FEATURE:
<221> NAME/KEY: VARIANT
<222> LOCATION: (107)
<223> OTHER INFORMATION: Wherein Xaa at position 107 designates Asn or
      Thr
<220> FEATURE:
<221> NAME/KEY: VARIANT
<222> LOCATION: (108)
<223> OTHER INFORMATION: Wherein Xaa at position 108 designates Ala or
      Pro

<400> SEQUENCE: 7

| Ala | Gly | Gly | Pro | Gly | Asn | Arg | Ala | Arg | Ala | Ala | Gly | Ala | Arg | Gly | Cys |
|---|---|---|---|---|---|---|---|---|---|---|---|---|---|---|---|
| 1 | | | | 5 | | | | | 10 | | | | | 15 | |

| Arg | Leu | Arg | Ser | Gln | Leu | Val | Pro | Val | Arg | Ala | Leu | Gly | Leu | Gly | His |
|---|---|---|---|---|---|---|---|---|---|---|---|---|---|---|---|
| | | | 20 | | | | | 25 | | | | | 30 | | |

| Arg | Ser | Asp | Glu | Leu | Val | Arg | Phe | Arg | Phe | Cys | Ser | Gly | Ser | Cys | Arg |
|---|---|---|---|---|---|---|---|---|---|---|---|---|---|---|---|
| | | 35 | | | | | 40 | | | | | 45 | | | |

| Arg | Ala | Arg | Ser | Pro | His | Asp | Leu | Ser | Leu | Ala | Ser | Leu | Leu | Gly | Ala |
|---|---|---|---|---|---|---|---|---|---|---|---|---|---|---|---|
| | 50 | | | | | 55 | | | | | 60 | | | | |

| Gly | Ala | Leu | Arg | Pro | Pro | Pro | Gly | Ser | Arg | Pro | Val | Ser | Gln | Pro | Cys |
|---|---|---|---|---|---|---|---|---|---|---|---|---|---|---|---|
| 65 | | | | | 70 | | | | | 75 | | | | | 80 |

| Cys | Arg | Pro | Thr | Arg | Tyr | Glu | Ala | Val | Ser | Phe | Met | Asp | Val | Asn | Ser |
|---|---|---|---|---|---|---|---|---|---|---|---|---|---|---|---|
| | | | | 85 | | | | | 90 | | | | | 95 | |

| Thr | Trp | Arg | Thr | Val | Asp | Arg | Leu | Ser | Ala | Xaa | Xaa | Cys | Gly | Cys | Leu |
|---|---|---|---|---|---|---|---|---|---|---|---|---|---|---|---|
| | | | 100 | | | | | 105 | | | | | 110 | | |

| Gly |
|---|
| |

<210> SEQ ID NO 8
<211> LENGTH: 861
<212> TYPE: DNA
<213> ORGANISM: Homo sapiens
<220> FEATURE:
<221> NAME/KEY: CDS
<222> LOCATION: (58)..(717)
<220> FEATURE:
<221> NAME/KEY: 5'UTR

```
<222> LOCATION: (1)..(57)
<220> FEATURE:
<221> NAME/KEY: 3'UTR
<222> LOCATION: (718)..(861)
<220> FEATURE:
<221> NAME/KEY: sig_peptide
<222> LOCATION: (58)..(174)
<220> FEATURE:
<221> NAME/KEY: mat_peptide
<222> LOCATION: (298)..(717)
<220> FEATURE:
<221> NAME/KEY: mat_peptide
<222> LOCATION: (370)..(717)
<220> FEATURE:
<221> NAME/KEY: mat_peptide
<222> LOCATION: (379)..(717)
<220> FEATURE:
<221> NAME/KEY: misc_structure
<222> LOCATION: (661)..(663)
<223> OTHER INFORMATION: CARBOHYD: glycosylated asparagine at Asn122
<220> FEATURE:
<221> NAME/KEY: misc_structure
<222> LOCATION: (424)..(621)
<223> OTHER INFORMATION: DISULFID: Gly43-Gly108 disulfide bridge
<220> FEATURE:
<221> NAME/KEY: misc_structure
<222> LOCATION: (505)..(705)
<223> OTHER INFORMATION: DISULFID: Gly70-Gly136 disulfide bridge
<220> FEATURE:
<221> NAME/KEY: misc_structure
<222> LOCATION: (517)..(711)
<223> OTHER INFORMATION: DISULFID: Gly74-Gly138 disulfide bridge
<220> FEATURE:
<221> NAME/KEY: misc_structure
<222> LOCATION: (616)..(618)
<223> OTHER INFORMATION: DISULFID: Gly107-Gly107 interchain disulfide
      bridge

<400> SEQUENCE: 8
aggagggtgg gggaacagct caacaatggc tgatgggcgc tcctggtgtt gatagag          57 atg gaa ctt gga ctt gga ggc ctc tcc acg ctg tcc cac tgc ccc tgg       105
Met Glu Leu Gly Leu Gly Gly Leu Ser Thr Leu Ser His Cys Pro Trp
-80              -75                 -70                 -65 cct agg cgg cag cct gcc ctg tgg ccc acc ctg gcc gct ctg gct ctg       153
Pro Arg Arg Gln Pro Ala Leu Trp Pro Thr Leu Ala Ala Leu Ala Leu
                -60                 -55                 -50 ctg agc agc gtc gca gag gcc tcc ctg ggc tcc gcg ccc cgc agc cct       201
Leu Ser Ser Val Ala Glu Ala Ser Leu Gly Ser Ala Pro Arg Ser Pro
            -45                 -40                 -35 gcc ccc cgc gaa ggc ccc ccg cct gtc ctg gcg tcc ccc gcc ggc cac       249
Ala Pro Arg Glu Gly Pro Pro Pro Val Leu Ala Ser Pro Ala Gly His
        -30                 -25                 -20 ctg ccg ggg gga cgc acg gcc cgc tgg tgc agt gga aga gcc cgg cgg       297
Leu Pro Gly Gly Arg Thr Ala Arg Trp Cys Ser Gly Arg Ala Arg Arg
    -15                 -10                 -5                  -1 ccg ccg ccg cag cct tct cgg ccc gcg ccc ccg cct gca ccc cca           345
Pro Pro Pro Gln Pro Ser Arg Pro Ala Pro Pro Pro Ala Pro Pro
1                   5                   10                  15 tct gct ctt ccc cgc ggg ggc cgc gcg gcg cgg gct ggg ggc cgg ggc       393
Ser Ala Leu Pro Arg Gly Gly Arg Ala Ala Arg Ala Gly Gly Pro Gly
                20                  25                  30 agc cgc gct cgg gca gcg ggg gcg cgg ggc tgc cgc ctg cgc tcg cag       441
Ser Arg Ala Arg Ala Ala Gly Ala Arg Gly Cys Arg Leu Arg Ser Gln
            35                  40                  45 ctg gtg ccg gtg cgc gcg ctc ggc ctg ggc cac cgc tcc gac gag ctg       489
Leu Val Pro Val Arg Ala Leu Gly Leu Gly His Arg Ser Asp Glu Leu
        50                  55                  60 gtg cgt ttc cgc ttc tgc agc ggc tcc tgc cgc cgc gcg cgc tct cca       537
```

-continued

```
Val Arg Phe Arg Phe Cys Ser Gly Ser Cys Arg Arg Ala Arg Ser Pro
 65                  70                  75                  80 cac gac ctc agc ctg gcc agc cta ctg ggc gcc ggg gcc ctg cga ccg    585
His Asp Leu Ser Leu Ala Ser Leu Leu Gly Ala Gly Ala Leu Arg Pro
                 85                  90                  95 ccc ccg ggc tcc cgg ccc gtc agc cag ccc tgc tgc cga ccc acg cgc    633
Pro Pro Gly Ser Arg Pro Val Ser Gln Pro Cys Cys Arg Pro Thr Arg
            100                 105                 110 tac gaa gcg gtc tcc ttc atg gac gtc aac agc acc tgg aga acc gtg    681
Tyr Glu Ala Val Ser Phe Met Asp Val Asn Ser Thr Trp Arg Thr Val
        115                 120                 125 gac cgc ctc tcc gcc acc gcc tgc ggc tgc ctg ggc tgagggctcg          727
Asp Arg Leu Ser Ala Thr Ala Cys Gly Cys Leu Gly
    130                 135                 140 ctccagggct tgcagactg gaccttacc ggtggctctt cctgcctggg accctcccgc     787
agagtcccac tagccagcgg cctcagccag ggacgaaggc ctcaaagctg agaggcccct   847
accggtgggt gatg                                                    861
```

<210> SEQ ID NO 9
<211> LENGTH: 220
<212> TYPE: PRT
<213> ORGANISM: Homo sapiens

<400> SEQUENCE: 9

```
Met Glu Leu Gly Leu Gly Gly Leu Ser Thr Leu Ser His Cys Pro Trp
-80                 -75                 -70                 -65

Pro Arg Arg Gln Pro Ala Leu Trp Pro Thr Leu Ala Ala Leu Ala Leu
                -60                 -55                 -50

Leu Ser Ser Val Ala Glu Ala Ser Leu Gly Ser Ala Pro Arg Ser Pro
            -45                 -40                 -35

Ala Pro Arg Glu Gly Pro Pro Val Leu Ala Ser Pro Ala Gly His
        -30                 -25                 -20

Leu Pro Gly Gly Arg Thr Ala Arg Trp Cys Ser Gly Arg Ala Arg Arg
    -15                 -10                  -5                  -1

Pro Pro Pro Gln Pro Ser Arg Pro Ala Pro Pro Pro Ala Pro Pro
  1                   5                  10                  15

Ser Ala Leu Pro Arg Gly Gly Arg Ala Ala Arg Ala Gly Gly Pro Gly
                 20                  25                  30

Ser Arg Ala Arg Ala Ala Gly Ala Arg Gly Cys Arg Leu Arg Ser Gln
             35                  40                  45

Leu Val Pro Val Arg Ala Leu Gly Leu Gly His Arg Ser Asp Glu Leu
 50                  55                  60

Val Arg Phe Arg Phe Cys Ser Gly Ser Cys Arg Arg Ala Arg Ser Pro
 65                  70                  75                  80

His Asp Leu Ser Leu Ala Ser Leu Leu Gly Ala Gly Ala Leu Arg Pro
                 85                  90                  95

Pro Pro Gly Ser Arg Pro Val Ser Gln Pro Cys Cys Arg Pro Thr Arg
            100                 105                 110

Tyr Glu Ala Val Ser Phe Met Asp Val Asn Ser Thr Trp Arg Thr Val
        115                 120                 125

Asp Arg Leu Ser Ala Thr Ala Cys Gly Cys Leu Gly
    130                 135                 140
```

<210> SEQ ID NO 10
<211> LENGTH: 140
<212> TYPE: PRT

```
<213> ORGANISM: Homo sapiens
<220> FEATURE:
<221> NAME/KEY: CARBOHYD
<222> LOCATION: (122)
<223> OTHER INFORMATION: glycosylated asparagine

<400> SEQUENCE: 10

Pro Pro Pro Gln Pro Ser Arg Pro Ala Pro Pro Pro Ala Pro Pro
 1               5                  10                  15

Ser Ala Leu Pro Arg Gly Gly Arg Ala Ala Arg Ala Gly Pro Gly
                20                  25                  30

Ser Arg Ala Arg Ala Ala Gly Ala Arg Gly Cys Arg Leu Arg Ser Gln
             35                  40                  45

Leu Val Pro Val Arg Ala Leu Gly Leu Gly His Arg Ser Asp Glu Leu
     50                  55                  60

Val Arg Phe Arg Phe Cys Ser Gly Ser Cys Arg Arg Ala Arg Ser Pro
 65                  70                  75                  80

His Asp Leu Ser Leu Ala Ser Leu Leu Gly Ala Gly Ala Leu Arg Pro
                 85                  90                  95

Pro Pro Gly Ser Arg Pro Val Ser Gln Pro Cys Cys Arg Pro Thr Arg
                100                 105                 110

Tyr Glu Ala Val Ser Phe Met Asp Val Asn Ser Thr Trp Arg Thr Val
            115                 120                 125

Asp Arg Leu Ser Ala Thr Ala Cys Gly Cys Leu Gly
130                 135                 140

<210> SEQ ID NO 11
<211> LENGTH: 116
<212> TYPE: PRT
<213> ORGANISM: Homo sapiens
<220> FEATURE:
<221> NAME/KEY: CARBOHYD
<222> LOCATION: (98)
<223> OTHER INFORMATION: glycosylated asparagine

<400> SEQUENCE: 11

Ala Ala Arg Ala Gly Gly Pro Gly Ser Arg Ala Arg Ala Gly Ala
 1               5                  10                  15

Arg Gly Cys Arg Leu Arg Ser Gln Leu Val Pro Val Arg Ala Leu Gly
                20                  25                  30

Leu Gly His Arg Ser Asp Glu Leu Val Arg Phe Arg Phe Cys Ser Gly
             35                  40                  45

Ser Cys Arg Arg Ala Arg Ser Pro His Asp Leu Ser Leu Ala Ser Leu
 50                  55                  60

Leu Gly Ala Gly Ala Leu Arg Pro Pro Pro Gly Ser Arg Pro Val Ser
 65                  70                  75                  80

Gln Pro Cys Cys Arg Pro Thr Arg Tyr Glu Ala Val Ser Phe Met Asp
                 85                  90                  95

Val Asn Ser Thr Trp Arg Thr Val Asp Arg Leu Ser Ala Thr Ala Cys
                100                 105                 110

Gly Cys Leu Gly
        115

<210> SEQ ID NO 12
<211> LENGTH: 113
<212> TYPE: PRT
<213> ORGANISM: Homo sapiens
<220> FEATURE:
<221> NAME/KEY: CARBOHYD
<222> LOCATION: (95)
```

-continued

```
<223> OTHER INFORMATION: glycosylated asparagine

<400> SEQUENCE: 12

Ala Gly Gly Pro Gly Ser Arg Ala Arg Ala Gly Ala Arg Gly Cys
  1               5                  10                  15

Arg Leu Arg Ser Gln Leu Val Pro Val Arg Ala Leu Gly Leu Gly His
                 20                  25                  30

Arg Ser Asp Glu Leu Val Arg Phe Arg Phe Cys Ser Gly Ser Cys Arg
             35                  40                  45

Arg Ala Arg Ser Pro His Asp Leu Ser Leu Ala Ser Leu Leu Gly Ala
         50                  55                  60

Gly Ala Leu Arg Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
                 85                  90                  95

Thr Trp Arg Thr Val Asp Arg Leu Ser Ala Thr Ala Cys Gly Cys Leu
                100                 105                 110

Gly

<210> SEQ ID NO 13
<211> LENGTH: 102
<212> TYPE: DNA
<213> ORGANISM: Homo sapiens

<400> SEQUENCE: 13
cctggccagc tactgggcg ccggggccct gcgaccgccc ccgggctccc ggcccgtcag     60
ccagccctgc tgccgaccca cgcgctacga agcggtctcc tt                     102

<210> SEQ ID NO 14
<211> LENGTH: 220
<212> TYPE: DNA
<213> ORGANISM: Murinae gen. sp.

<400> SEQUENCE: 14
ggccaccgct ccgacgagct gatacgtttc gcttctgca gcggctcgtg ccgccgagca     60
cgctcccagc acgatctcag tctggccagc tactgggcg ctggggccct acggtcgcct   120
cccgggtccc ggccgatcag ccagccctgc tgccggccca ctcgctatga ggccgtctcc   180
ttcatggacg tgaacagcac ctggagaacc gtggaccgcc                        220

<210> SEQ ID NO 15
<211> LENGTH: 2136
<212> TYPE: DNA
<213> ORGANISM: Murinae gen. sp.
<220> FEATURE:
<221> NAME/KEY: CDS
<222> LOCATION: (975)..(1646)

<400> SEQUENCE: 15
gcggccgcga attcggcacg agggcgtctc gctgcagccc gcgatctcta ctctgcctcc     60
tggggtcttc tccaaatgtc tagcccccac ctagagggac ctagcctagc cagcggggac   120
cggatccgga gggtggagcg gccaggtgag ccctgaaagg tggggcgggg cggggcgct    180 ctgggcccca ccccgggatc tggtgacgcc ggggctgaa tttgacaccg acggcggcg    240 ggcaggaggc tgctgaggga tggagttggg ctcggccccc agatgcggcc gcgggctct   300 gccagcaaca agtccctcgg gccccagccc tcgctgcgac tggggcttgg agccctgcac   360
ccaagggcac agaccggctg ccaaggcccc acttttaact aaaagaggcg ctgccaggtg   420
```

-continued

```
cacaactctg gcatgatcc acttgagctt cggggggaaag cccagcactg gtcccaggag      480
aggcgcctag aaggacacgg accaggaccc ctttggtatg gagtgaacgc tgagcatgga      540
gtggaaggaa ctcaagttac tactttctcc aaccaccctg gtaccttcag ccctgaagta      600
cagagcagaa gggtcttaga agacaggacc acagctgtgt gagtctcccc cctgaggcct      660
tagacgatct ctgagctcag ctgagctttg tttgcccatc tggagaagtg agccattgat      720
tgaccttgtg gcatcgcgaa ggaacaggtc ctgccaagca cctaacacag agagcaaggt      780
tctccatcgc agctaccgct gctgagttga ctctagctac tccaacctcc tgggtcgctt      840
cgagagactg gagtggaagg aggaatacccc caaaggataa ctaactcatc tttcagtttg      900
caagctgccg caggaagagg gtggggaaac gggtccacga aggcttctga tgggagcttc      960
```

| | | | | | | | | | | | | | | | |
|---|---|---|---|---|---|---|---|---|---|---|---|---|---|---|---|
| tggagccgaa agct | atg | gaa | ctg | gga | ctt | gca | gag | cct | act | gca | ttg | tcc | | | 1010 |
| | Met | Glu | Leu | Gly | Leu | Ala | Glu | Pro | Thr | Ala | Leu | Ser | | | |
| | 1 | | | 5 | | | | | 10 | | | | | | |

| cac | tgc | ctc | cgg | cct | agg | tgg | cag | tca | gcc | tgg | tgg | cca | acc | cta | gct | 1058 |
|---|---|---|---|---|---|---|---|---|---|---|---|---|---|---|---|---|
| His | Cys | Leu | Arg | Pro | Arg | Trp | Gln | Ser | Ala | Trp | Trp | Pro | Thr | Leu | Ala | |
| | 15 | | | | 20 | | | | | 25 | | | | | | |

| gtt | cta | gcc | ctg | ctg | agc | tgc | gtc | aca | gaa | gct | tcc | ctg | gac | cca | atg | 1106 |
|---|---|---|---|---|---|---|---|---|---|---|---|---|---|---|---|---|
| Val | Leu | Ala | Leu | Leu | Ser | Cys | Val | Thr | Glu | Ala | Ser | Leu | Asp | Pro | Met | |
| 30 | | | | | 35 | | | | | 40 | | | | | | |

| tcc | cgc | agc | ccc | gcc | gct | cgc | gac | ggt | ccc | tca | ccg | gtc | ttg | gcg | ccc | 1154 |
|---|---|---|---|---|---|---|---|---|---|---|---|---|---|---|---|---|
| Ser | Arg | Ser | Pro | Ala | Ala | Arg | Asp | Gly | Pro | Ser | Pro | Val | Leu | Ala | Pro | |
| 45 | | | | 50 | | | | | 55 | | | | | | 60 | |

| ccc | acg | gac | cac | ctg | cct | ggg | gga | cac | act | gcg | cat | ttg | tgc | agc | gaa | 1202 |
|---|---|---|---|---|---|---|---|---|---|---|---|---|---|---|---|---|
| Pro | Thr | Asp | His | Leu | Pro | Gly | Gly | His | Thr | Ala | His | Leu | Cys | Ser | Glu | |
| | | | 65 | | | | | 70 | | | | | 75 | | | |

| aga | acc | ctg | cga | ccc | ccg | cct | cag | tct | cct | cag | ccc | gca | ccc | ccg | ccg | 1250 |
|---|---|---|---|---|---|---|---|---|---|---|---|---|---|---|---|---|
| Arg | Thr | Leu | Arg | Pro | Pro | Pro | Gln | Ser | Pro | Gln | Pro | Ala | Pro | Pro | Pro | |
| | | 80 | | | | | 85 | | | | | 90 | | | | |

| cct | ggt | ccc | gcg | ctc | cag | tct | cct | ccc | gct | gcg | ctc | cgc | ggg | gca | cgc | 1298 |
|---|---|---|---|---|---|---|---|---|---|---|---|---|---|---|---|---|
| Pro | Gly | Pro | Ala | Leu | Gln | Ser | Pro | Pro | Ala | Ala | Leu | Arg | Gly | Ala | Arg | |
| | 95 | | | | | 100 | | | | | 105 | | | | | |

| gcg | gcg | cgt | gca | gga | acc | cgg | agc | agc | cgc | gca | cgg | acc | aca | gat | gcg | 1346 |
|---|---|---|---|---|---|---|---|---|---|---|---|---|---|---|---|---|
| Ala | Ala | Arg | Ala | Gly | Thr | Arg | Ser | Ser | Arg | Ala | Arg | Thr | Thr | Asp | Ala | |
| | 110 | | | | | 115 | | | | | 120 | | | | | |

| cgc | ggc | tgc | cgc | ctg | cgc | tcg | cag | ctg | gtg | ccg | gtg | agc | gcg | ctc | ggc | 1394 |
|---|---|---|---|---|---|---|---|---|---|---|---|---|---|---|---|---|
| Arg | Gly | Cys | Arg | Leu | Arg | Ser | Gln | Leu | Val | Pro | Val | Ser | Ala | Leu | Gly | |
| 125 | | | | | 130 | | | | | 135 | | | | | 140 | |

| cta | ggc | cac | agc | tcc | gac | gag | ctg | ata | cgt | ttc | cgc | ttc | tgc | agc | ggc | 1442 |
|---|---|---|---|---|---|---|---|---|---|---|---|---|---|---|---|---|
| Leu | Gly | His | Ser | Ser | Asp | Glu | Leu | Ile | Arg | Phe | Arg | Phe | Cys | Ser | Gly | |
| | | | 145 | | | | | 150 | | | | | 155 | | | |

| tcg | tgc | cgc | cga | gca | cgc | tcc | cag | cac | gat | ctc | agt | ctg | gcc | agc | cta | 1490 |
|---|---|---|---|---|---|---|---|---|---|---|---|---|---|---|---|---|
| Ser | Cys | Arg | Arg | Ala | Arg | Ser | Gln | His | Asp | Leu | Ser | Leu | Ala | Ser | Leu | |
| | | 160 | | | | | 165 | | | | | 170 | | | | |

| ctg | ggc | gct | ggg | gcc | cta | cgg | tcg | cct | ccc | ggg | tcc | cgg | ccg | atc | agc | 1538 |
|---|---|---|---|---|---|---|---|---|---|---|---|---|---|---|---|---|
| Leu | Gly | Ala | Gly | Ala | Leu | Arg | Ser | Pro | Pro | Gly | Ser | Arg | Pro | Ile | Ser | |
| | 175 | | | | | 180 | | | | | 185 | | | | | |

| cag | ccc | tgc | tgc | cgg | ccc | act | cgc | tat | gag | gcc | gtc | tcc | ttc | atg | gac | 1586 |
|---|---|---|---|---|---|---|---|---|---|---|---|---|---|---|---|---|
| Gln | Pro | Cys | Cys | Arg | Pro | Thr | Arg | Tyr | Glu | Ala | Val | Ser | Phe | Met | Asp | |
| | 190 | | | | | 195 | | | | | 200 | | | | | |

| gtg | aac | agc | acc | tgg | agg | acc | gtg | gac | cac | ctc | tcc | gcc | act | gcc | tgc | 1634 |
|---|---|---|---|---|---|---|---|---|---|---|---|---|---|---|---|---|
| Val | Asn | Ser | Thr | Trp | Arg | Thr | Val | Asp | His | Leu | Ser | Ala | Thr | Ala | Cys | |
| 205 | | | | | 210 | | | | | 215 | | | | | 220 | |

| ggc | tgt | ctg | ggc | tgaggatgat | ctatctccaa | gcctttgcac | actagaccca | | | | | | | | | 1686 |
|---|---|---|---|---|---|---|---|---|---|---|---|---|---|---|---|---|
| Gly | Cys | Leu | Gly | | | | | | | | | | | | | |

```
tgtgttgccc tacctggaac agctccaccg ggcctcacta accaggagcc tcaactcagc      1746
```

```
aggatatgga ggctgcagag ctcaggcccc aggccggtga gtgacagacg tcgtcggcat    1806
gacagacaga gtgaaagatg tcggaaccac tgaccaacag tcccaagttg ttcatggatc    1866
ccagctctac agacaggaga aacctcagct aaagagaact cctctgggag aatccagaaa    1926
tggccctctg tcctggggaa tgaattttga agagatatat atacatatat acattgtagt    1986
cgcgttgctg gaccagcctg tgctgaaacc agtcccgtgt tcacttgtgg aagccgaagc    2046
cctatttatt atttctaaat tatttattta ctttgaaaaa aaacggccaa gtcggcctcc    2106
ctttagtgag ggttaatttg tgatcccggg                                     2136
```

<210> SEQ ID NO 16
<211> LENGTH: 224
<212> TYPE: PRT
<213> ORGANISM: Murinae gen. sp.

<400> SEQUENCE: 16

```
Met Glu Leu Gly Leu Ala Glu Pro Thr Ala Leu Ser His Cys Leu Arg
 1               5                  10                  15

Pro Arg Trp Gln Ser Ala Trp Trp Pro Thr Leu Ala Val Leu Ala Leu
            20                  25                  30

Leu Ser Cys Val Thr Glu Ala Ser Leu Asp Pro Met Ser Arg Ser Pro
        35                  40                  45

Ala Ala Arg Asp Gly Pro Ser Pro Val Leu Ala Pro Thr Asp His
    50                  55                  60

Leu Pro Gly Gly His Thr Ala His Leu Cys Ser Glu Arg Thr Leu Arg
65                  70                  75                  80

Pro Pro Pro Gln Ser Pro Gln Pro Ala Pro Pro Pro Gly Pro Ala
                85                  90                  95

Leu Gln Ser Pro Pro Ala Ala Leu Arg Gly Ala Arg Ala Ala Arg Ala
               100                 105                 110

Gly Thr Arg Ser Ser Arg Ala Arg Thr Thr Asp Ala Arg Gly Cys Arg
           115                 120                 125

Leu Arg Ser Gln Leu Val Pro Val Ser Ala Leu Gly Leu Gly His Ser
       130                 135                 140

Ser Asp Glu Leu Ile Arg Phe Arg Phe Cys Ser Gly Ser Cys Arg Arg
145                 150                 155                 160

Ala Arg Ser Gln His Asp Leu Ser Leu Ala Ser Leu Leu Gly Ala Gly
                165                 170                 175

Ala Leu Arg Ser Pro Pro Gly Ser Arg Pro Ile Ser Gln Pro Cys Cys
            180                 185                 190

Arg Pro Thr Arg Tyr Glu Ala Val Ser Phe Met Asp Val Asn Ser Thr
        195                 200                 205

Trp Arg Thr Val Asp His Leu Ser Ala Thr Ala Cys Gly Cys Leu Gly
    210                 215                 220
```

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 17

```
cctggccagc ctactggg                                                    18
```

<210> SEQ ID NO 18

```
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 18
aaggagaccg cttcgtagcg                                              20

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: PCR Primer

<400> SEQUENCE: 19
atggaacttg gacttgg                                                 17

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: PCR Primer

<400> SEQUENCE: 20
tccatcaccc accggc                                                  16

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 21
ggccaccgct ccgacgag                                                18

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 22
ggcggtccac ggttctccag                                              20

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 23
ccaagcccac ctgggtgccc tctttctcc                                    29

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: PCR Primer

<400> SEQUENCE: 24
```

```
catcacccac cggcagggge ctctcag                                        27
```

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: PCR Primer

<400> SEQUENCE: 25

```
gagcccatgc ccggcctgat ctcagcccga ggaca                               35
```

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: PCR Primer

<400> SEQUENCE: 26

```
ccctggctga ggccgctggc tagtgggact ctgc                                34
```

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence:
      Hybridization Probe
<220> FEATURE:
<221> NAME/KEY: misc_feature
<222> LOCATION: (1)
<223> OTHER INFORMATION: Wherein n is designated as a, c, t or g

<400> SEQUENCE: 27

```
ncaggtggtc cgtgggggge gccaagaccg g                                   31
```

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: PCR primer

<400> SEQUENCE: 28

```
ctaggagccc atgccc                                                    16
```

<210> SEQ ID NO 29
<211> LENGTH: 351
<212> TYPE: DNA
<213> ORGANISM: Homo sapiens

<400> SEQUENCE: 29

```
atggctggag gaccgggatc tcgtgctcgt gcagcaggag cacgtggctg tcgtctgcgt    60
tctcaactag tgccggtgcg tgcactcgga ctgggacacc gttccgacga actagtacgt   120
tttcgttttt gttcaggatc ttgtcgtcgt gcacgttctc cgcatgatct atctctagca   180
tctctactag gagccggagc actaagaccg ccgcgggat ctagacctgt atctcaacct    240
tgttgtagac ctactagata cgaagcagta tctttcatgg acgtaaactc tacatggaga   300
accgtagata gactatctgc aaccgcatgt ggctgtctag gatgataata g             351
```

<210> SEQ ID NO 30
<211> LENGTH: 414

```
<212> TYPE: DNA
<213> ORGANISM: Homo sapiens

<400> SEQUENCE: 30
atgggccatc atcatcatca tcatcatcat catcactcga gcggccatat cgacgacgac      60
gacaaggctg gaggaccggg atctcgtgct cgtgcagcag gagcacgtgg ctgtcgtctg     120
cgttctcaac tagtgccggt gcgtgcactc ggactgggac accgttccga cgaactagta     180
cgttttcgtt tttgttcagg atcttgtcgt cgtgcacgtt ctccgcatga tctatctcta     240
gcatctctac taggagccgg agcactaaga ccgccgccgg gatctagacc tgtatctcaa     300
ccttgttgta gacctactag atacgaagca gtatctttca tggacgtaaa ctctacatgg     360
agaaccgtag atagactatc tgcaaccgca tgtggctgtc taggatgata atag           414

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: PCR primer

<400> SEQUENCE: 31
aaggaaaaaa gcggccgcca tggaacttgg acttggagg                              39

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: PCR primer

<400> SEQUENCE: 32 tttttttcctt ggcggccgct cagcccaggc agccgcagg                             39

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 33
gagcgagccc tcagcc                                                       16

<210> SEQ ID NO 34
<211> LENGTH: 197
<212> TYPE: PRT
<213> ORGANISM: Homo sapiens

<400> SEQUENCE: 34

Met Gln Arg Trp Lys Ala Ala Ala Leu Ala Ser Val Leu Cys Ser Ser
  1               5                  10                  15

Val Leu Ser Ile Trp Met Cys Arg Glu Gly Leu Leu Leu Ser His Arg
             20                  25                  30

Leu Gly Pro Ala Leu Val Pro Leu His Arg Leu Pro Arg Thr Leu Asp
         35                  40                  45

Ala Arg Ile Ala Arg Leu Ala Gln Tyr Arg Ala Leu Leu Gln Gly Ala
     50                  55                  60

Pro Asp Ala Met Glu Leu Arg Glu Leu Thr Pro Trp Ala Gly Arg Pro
 65                  70                  75                  80

Pro Gly Pro Arg Arg Arg Ala Gly Pro Arg Arg Arg Arg Ala Arg Ala
```

```
                    85                  90                  95
Arg Leu Gly Ala Arg Pro Cys Gly Leu Arg Glu Leu Glu Val Arg Val
                100                 105                 110

Ser Glu Leu Gly Leu Gly Tyr Ala Ser Asp Glu Thr Val Leu Phe Arg
            115                 120                 125

Tyr Cys Ala Gly Ala Cys Glu Ala Ala Arg Val Tyr Asp Leu Gly
130                 135                 140

Leu Arg Arg Leu Arg Gln Arg Arg Leu Arg Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Ala His Ser Arg Tyr His Thr Val His Glu Leu Ser Ala Arg
                180                 185                 190

Glu Cys Ala Cys Val
            195

<210> SEQ ID NO 35
<211> LENGTH: 220
<212> TYPE: PRT
<213> ORGANISM: Homo sapiens

<400> SEQUENCE: 35

Met Glu Leu Gly Leu Gly Gly Leu Ser Thr Leu Ser His Cys Pro Trp
1               5                   10                  15

Pro Arg Arg Gln Pro Ala Leu Trp Pro Thr Leu Ala Ala Leu Ala Leu
            20                  25                  30

Leu Ser Ser Val Ala Glu Ala Ser Leu Gly Ser Ala Pro Arg Ser Pro
        35                  40                  45

Ala Pro Arg Glu Gly Pro Pro Pro Val Leu Ala Ser Pro Ala Gly His
    50                  55                  60

Leu Pro Gly Gly Arg Thr Ala Arg Trp Cys Ser Gly Arg Ala Arg Arg
65                  70                  75                  80

Pro Pro Pro Gln Pro Ser Arg Pro Ala Pro Pro Pro Ala Pro Pro
                85                  90                  95

Ser Ala Leu Pro Arg Gly Gly Arg Ala Ala Arg Ala Gly Gly Pro Gly
                100                 105                 110

Ser Arg Ala Arg Ala Ala Gly Ala Arg Gly Cys Arg Leu Arg Ser Gln
            115                 120                 125

Leu Val Pro Val Arg Ala Leu Gly Leu Gly His Arg Ser Asp Glu Leu
        130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
                165                 170                 175

Pro Pro Gly Ser Arg Pro Val Ser Gln Pro Cys Cys Arg Pro Thr Arg
                180                 185                 190

Tyr Glu Ala Val Ser Phe Met Asp Val Asn Ser Thr Trp Arg Thr Val
            195                 200                 205

Asp Arg Leu Ser Ala Thr Ala Cys Gly Cys Leu Gly
    210                 215                 220

<210> SEQ ID NO 36
<211> LENGTH: 156
<212> TYPE: PRT
<213> ORGANISM: Homo sapiens
```

```
<400> SEQUENCE: 36

Met Ala Val Gly Lys Phe Leu Leu Gly Ser Leu Leu Leu Leu Ser Leu
 1               5                  10                  15

Gln Leu Gly Gln Gly Trp Gly Pro Asp Ala Arg Gly Val Pro Val Ala
             20                  25                  30

Asp Gly Glu Phe Ser Ser Glu Gln Val Ala Lys Ala Gly Gly Thr Trp
         35                  40                  45

Leu Gly Thr His Arg Pro Leu Ala Arg Leu Arg Ala Leu Ser Gly
     50                  55                  60

Pro Cys Gln Leu Trp Ser Leu Thr Leu Ser Val Ala Glu Leu Gly Leu
 65                  70                  75                  80

Gly Tyr Ala Ser Glu Glu Lys Val Ile Phe Arg Tyr Cys Ala Gly Ser
                 85                  90                  95

Cys Pro Arg Gly Ala Arg Thr Gln His Gly Leu Ala Leu Ala Arg Leu
            100                 105                 110

Gln Gly Gln Gly Arg Ala His Gly Gly Pro Cys Cys Arg Pro Thr Arg
        115                 120                 125

Tyr Thr Asp Val Ala Phe Leu Asp Asp Arg His Arg Trp Gln Arg Leu
130                 135                 140

Pro Gln Leu Ser Ala Ala Ala Cys Gly Cys Gly Gly
145                 150                 155

<210> SEQ ID NO 37
<211> LENGTH: 211
<212> TYPE: PRT
<213> ORGANISM: Homo sapiens

<400> SEQUENCE: 37

Met Lys Leu Trp Asp Val Val Ala Val Cys Leu Val Leu Leu His Thr
 1               5                  10                  15

Ala Ser Ala Phe Pro Leu Pro Ala Gly Lys Arg Pro Pro Glu Ala Pro
             20                  25                  30

Ala Glu Asp Arg Ser Leu Gly Arg Arg Arg Ala Pro Phe Ala Leu Ser
         35                  40                  45

Ser Asp Ser Asn Met Pro Glu Asp Tyr Pro Asp Gln Phe Asp Asp Val
     50                  55                  60

Met Asp Phe Ile Gln Ala Thr Ile Lys Arg Leu Lys Arg Ser Pro Asp
 65                  70                  75                  80

Lys Gln Met Ala Val Leu Pro Arg Arg Glu Arg Asn Arg Gln Ala Ala
                 85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Leu Ser Phe Leu Asp
            180                 185                 190

Asp Asn Leu Val Tyr His Ile Leu Arg Lys His Ser Ala Lys Arg Cys
        195                 200                 205
```

Gly Cys Ile
    210

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 38
gctggcccgg ctgcaggg                                          18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 39
gctgcgacga ctgcgcca                                          18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 40
attgaaaaac ttatccag                                          18

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 41
taggccacgt cggtgtagcg                                        20

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 42
aaggacacct cgtcctcgta ggc                                    23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 43
aacgacaggt catcatcaaa ggc                                    23